(12) United States Patent
Barna et al.

(10) Patent No.: US 11,492,611 B2
(45) Date of Patent: Nov. 8, 2022

(54) SYSTEMS AND METHODS FOR PRODUCING RNA CONSTRUCTS WITH INCREASED TRANSLATION AND STABILITY

(71) Applicant: The Board of Trustees of the Leland Stanford Junior University, Stanford, CA (US)

(72) Inventors: Maria Barna, Stanford, CA (US); Kathrin Leppek, Stanford, CA (US); Gun Woo Byeon, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/463,466

(22) Filed: Aug. 31, 2021

(65) Prior Publication Data
US 2022/0064631 A1    Mar. 3, 2022

Related U.S. Application Data

(60) Provisional application No. 63/072,669, filed on Aug. 31, 2020.

(51) Int. Cl.
*C12N 15/10*    (2006.01)

(52) U.S. Cl.
CPC ................................ *C12N 15/1065* (2013.01)

(58) Field of Classification Search
None
See application file for complete search history.

(56) References Cited

U.S. PATENT DOCUMENTS

| | | | |
|---|---|---|---|
| 5,846,772 A | 12/1998 | Hodgson et al. | |
| 8,278,036 B2 | 10/2012 | Kariko et al. | |
| 9,885,034 B2 | 2/2018 | Saxonov | |
| 10,022,435 B2 | 7/2018 | Ciaramella et al. | |
| 10,460,220 B2 | 10/2019 | Church | |
| 2004/0248140 A1 | 12/2004 | Endo et al. | |
| 2010/0047261 A1 | 2/2010 | Hoerr et al. | |
| 2014/0206753 A1 | 7/2014 | Guild et al. | |
| 2019/0345513 A1 | 11/2019 | Qureshi et al. | |
| 2020/0017858 A1* | 1/2020 | Volles et al. | C12N 15/85 |
| 2020/0032274 A1 | 1/2020 | Mauger et al. | |
| 2020/0063190 A1 | 2/2020 | Chenchik et al. | |
| 2022/0010299 A1 | 1/2022 | Das et al. | |
| 2022/0135964 A1 | 5/2022 | Barna et al. | |
| 2022/0162588 A1 | 5/2022 | Barna et al. | |

FOREIGN PATENT DOCUMENTS

| | | |
|---|---|---|
| CN | 103725773 B | 11/2015 |
| WO | 2012041802 A1 | 4/2012 |
| WO | 2017070626 A2 | 4/2017 |
| WO | 2019209079 A1 | 10/2019 |
| WO | 2021011433 A1 | 1/2021 |
| WO | 2022015513 A2 | 1/2022 |
| WO | 2022015513 A3 | 1/2022 |
| WO | 2022047427 A2 | 3/2022 |
| WO | 2022015513 A4 | 4/2022 |
| WO | 2022047427 A3 | 4/2022 |

OTHER PUBLICATIONS

Cottrell et al., "PTRE-seq reveals mechanism and interactions of RNA binding proteins and miRNAs," Nat. Commun. 2018, 9:301. (Year: 2018).*
International Search Report and Written Opinion for International Application No. PCT/US2021/040027, Search completed Oct. 5, 2021, dated Jan. 6, 2022, 31 Pgs.
International Search Report and Written Opinion for International Application No. PCT/US2021/048561, Search completed Jan. 21, 2022, dated Feb. 16, 2022, 22 Pgs.
Brogna et al., "Nonsense-mediated mRNA decay (NMD) mechanisms", Nature Structural & Molecular Biology, vol. 16, Feb. 2009, pp. 107-113, doi: https://doi.org/10.1038/nsmb.1550.
Bunnik et al., "Polysome profiling reveals translational control of gene expression in the human malaria parasite Plasmodium falciparum", Genome Biology, vol. 14, No. R128, Nov. 22, 2013, 18 pgs.
Chan et al., "Non-Invasive Measurement of mRNA Decay Reveals Translation Initiation as the Major Determinant of mRNA Stability", eLife Sep. 7, 2018, vol. 7:e32536, pp. 1-32. DOI: https://doi.org/10.7554/eLife.32536.
Chasse et al., "Analysis of translation using polysome profiling", Nucleic Acids Research, vol. 45, No. 3, Feb. 2017, e15, 9 pgs., https://doi.org/10.1093/nar/gkw907.
Cottrell et al., "PTRE-Seq Reveals Mechanism and Interactions of RNA Binding Proteins and miRNAs", Nature Communications (2018), vol. 9, No. 301, 13 pgs., DOI: 10.1038/s41467-017-02745-0.
Davis, "Stabilization of RNA stacking by pseudouridine", Nucleic Acids Research, vol. 23, No. 24, Dec. 25, 1995, pp. 5020-5026, doi: https://doi.org/10.1093/nar/23.24.5020.
Erasmus et al., "An Alphavirus-derived replicon RNA vaccine induces SARS-CoV-2 neutralizing antibody and T cell responses in mice and nonhuman primates", Science Translational Medicine, vol. 12, No. 555, Aug. 5, 2020, eabc9396, 11 pgs, doi: 10.1126/scitranslmed.abc9396.
Fischer et al., "Structure-Mediated RNA Decay by UPF1 and G3BP1", Molecular Cell, vol. 78, No. 1, Apr. 2, 2020, pp. 70-84.e6, doi: https://doi.org/10.1016/j.molcel.2020.01.021.

(Continued)

*Primary Examiner* — Kaijiang Zhang
(74) *Attorney, Agent, or Firm* — KPPB LLP

(57) ABSTRACT

Systems and methods for enhancing RNA translatability and stability are disclosed. Some embodiments describe RNA molecules exhibiting increased translatability and/or stability. Additional embodiments describe methods for screening RNA molecules for increased translatability and/or stability. Various embodiments utilize screening methods, including degenerative sequences to identify sequences or regions that increase the translatability and/or stability of RNA molecules.

6 Claims, 14 Drawing Sheets
(7 of 14 Drawing Sheet(s) Filed in Color)
Specification includes a Sequence Listing.

(56) References Cited

OTHER PUBLICATIONS

Kariko et al., "Incorporation of Pseudouridine Into mRNA Yields Superior Nonimmunogenic Vector With Increased Translational Capacity and Biological Stability", Molecular Therapy, vol. 16, No. 11, Nov. 1, 2008, pp. 1833-1840, doi: https://doi.org/10.1038/mt.2008.200.

Koh et al., "Tuning of mRNA stability through altering 3'-UTR sequences generates distinct output expression in a synthetic circuit driven by p53 oscillations", Scientific Reports, vol. 9, No. 5976, Apr. 12, 2019, 8 pgs.

Li et al., "Kinetics of RNA Degradation by Specific Base Catalysis of Transesterification Involving the 2'-Hydroxyl Group", Journal of the American Chemical Society, vol. 121, No. 23, May 25, 1999, pp. 5364-5372, doi: 10.1021/ja990592p.

Liang et al., "Polysome-profiling in small tissue samples", Nucleic Acids Research, vol. 46, No. 1, Jan. 9, 2018, e3, 13 pgs., https://doi.org/10.1093/nar/gkx940.

Mauger et al., "mRNA structure regulates protein expression through changes in functional half-life", PNAS, vol. 116, No. 48, Nov. 26, 2019, pp. 24075-24083, doi: https://doi.org/10.1073/pnas.1908052116.

Mercier et al., "Translation-dependent and independent mRNA decay occur through mutually exclusive pathways that are defined by ribosome density during T Cell activation", bioRxiv, Oct. 17, 2020, 45 pgs, doi: https://doi.org/10.1101/2020.10.16.341222.

Park et al., "Staufen-mediated mRNA decay", Wiley Interdisciplinary Reviews RNA, vol. 4, No. 4, Jul. 2013, pp. 423-435, doi: 10.1002/wrna.1168.

Pringle et al., "Polysome Profiling Analysis of mRNA and Associated Proteins Engaged in Translation", Current Protocols in Molecular Biology, vol. 125, No. 1, Jan. 2019, Electronic Publication: Oct. 29, 2018, e79, doi: 10.1002/cpmb.79.

Wayment-Steele et al., "Theoretical basis for Stabilizing Messenger RNA through Secondary Structure Design", bioRxiv, Preprint, Version 2, Aug. 24, 2020, Retrieved on Sep. 27, 2021 from: URL:https://www.ncbi.nlm.nih.gov/pmc/articles/PMC7457604/, 25 pgs.

Zhang et al., "A Thermostable mRNA Vaccine against COVID-19", Cell, vol. 182, No. 5, Sep. 3, 2020, pp. 1271-1283.e16, doi: 10.1016/j.cell.2020.07.024.

Bae et al., "High-throughput methods for measuring DNA thermodynamics", Nucleic Acids Research, vol. 48, No. 15, Sep. 4, 2020, e89, 9 pgs., https://doi.org/10.1093/nar/gkaa521.

Becker et al., "Quantitative high-throughput tests of ubiquitous RNA secondary structure prediction algorithms via RNA/protein binding", bioRxiv preprint, Mar. 8, 2019, 22 pgs., doi: https://doi.org/10.1101/571588.

Buenrostro et al., "Quantitative analysis of RNA-protein interactions on a massively parallel array reveals biophysical and evolutionary landscapes", Nature Biotechnology, vol. 32, Apr. 13, 2014, pp. 562-568, doi:10.1038/nbt.2880.

Denny et al., "High-Throughput Investigation of Diverse Junction Elements in RNA Tertiary Folding", Cell, vol. 174, No. 2, Jul. 12, 2018, pp. 377-390.e20, doi: 10.1016/j.cell.2018.05.038.

Lorenz et al., "ViennaRNA Package 2.0", Algorithms for Molecular Biology, vol. 6, No. 26, Nov. 24, 2011, 14 pgs.

Reuter et al., "RNAstructure: software for RNA secondary structure prediction and analysis", BMC Bioinformatics, vol. 11, No. 129, Mar. 15, 2010, 9 pgs.

Santalucia, Jr., "A unified view of polymer, dumbbell, and oligonucleotide DNA nearest-neighbor thermodynamics", Proc. Natl. Acad. Sci., USA, Feb. 1998, vol. 95, pp. 1460-1465.

She et al., "Comprehensive and quantitative mapping of RNA-protein interactions across a transcribed eukaryotic genome", PNAS, vol. 114, No. 14, Apr. 4, 2017, pp. 3619-3624.

Spasic et al., "Improving RNA nearest neighbor parameters for helices by going beyond the two-state model", Nucleic Acids Research, vol. 46, No. 10, Jun. 1, 2018, Online Publication: May 1, 2018, pp. 4883-4892, doi: 10.1093/nar/gky270.

Wayment-Steele et al., "RNA secondary structure packages ranked and improved by high-throughput experiments", bioRxiv preprint, May 31, 2020, 31 pgs, doi: https://doi.org/10.1101/2020.05.29.124511.

Wreschner et al., "Differential mRNA stability to reticulocyte ribonucleases correlates with 3' non-coding (U),,A sequences", Eur. J. Biochem. 1988, vol. 172, pp. 333-340.

Xia et al., "Thermodynamic Parameters for an Expanded Nearest-Neighbor Model for Formation of RNA Duplexes with Watson-Crick Base Pairs", Biochemistry, vol. 37, No. 42, Oct. 1, 1998, pp. 14719-14735.

Zadeh et al., "NUPACK: Analysis and Design of Nucleic Acid Systems", Journal of Computational Chemistry, Software News and Update, vol. 32, Jan. 15, 2011, pp. 170-173, doi: 10.1002/jcc.21596.

\* cited by examiner

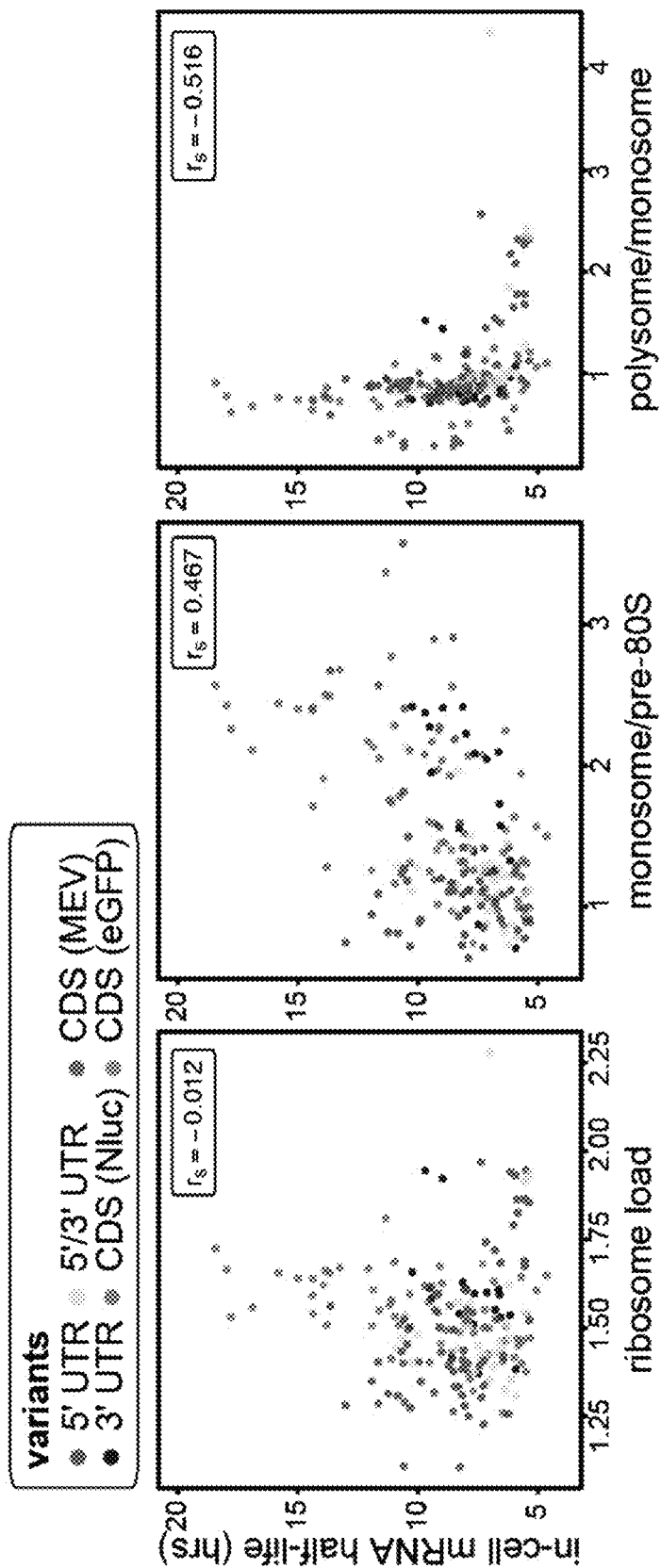

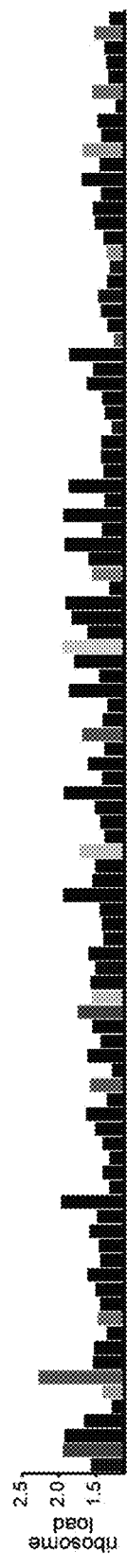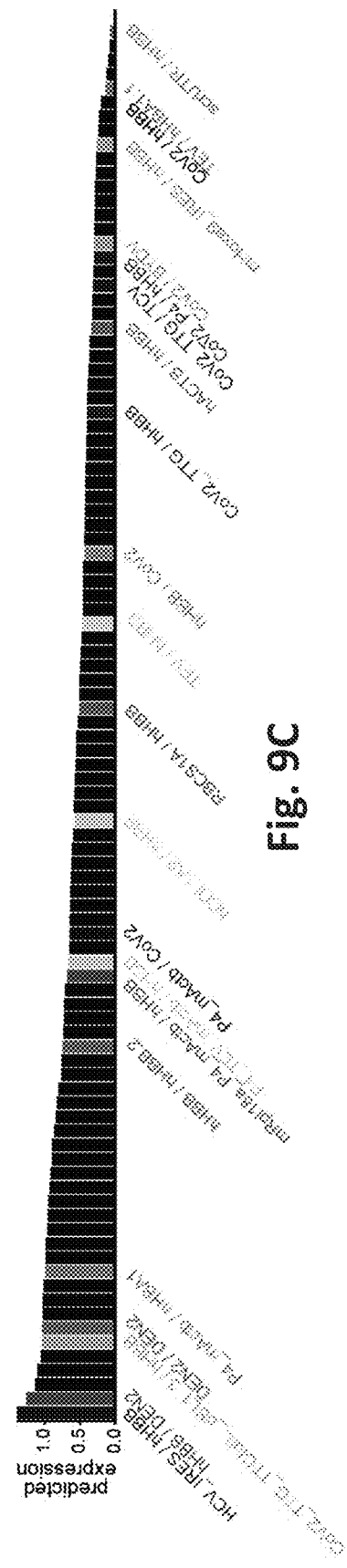
Fig. 9A
Fig. 9B
Fig. 9C

SYSTEMS AND METHODS FOR PRODUCING RNA CONSTRUCTS WITH INCREASED TRANSLATION AND STABILITY

CROSS-REFERENCE TO RELATED APPLICATIONS

The current application claims priority to U.S. Provisional Patent Application No. 63/072,669, filed Aug. 31, 2020; the disclosures of which is hereby incorporated by reference in its entirety.

FIELD OF THE DISCLOSURE

The present invention relates to ribonucleic acid (RNA). More specifically, the present invention relates to systems and methods to enhance RNA translatability and assessment thereof.

INCORPORATION OF SEQUENCE LISTING

This application hereby incorporates by reference the material of the electronic Sequence Listing filed concurrently herewith. The material in the electronic Sequence Listing is submitted as a text (.txt) file entitled "06753_Seq_List_ST25.txt" created on Aug. 31, 2021, which has a file size of approximately 282 KB, and is herein incorporated by reference in its entirety.

BACKGROUND OF THE DISCLOSURE

There are multiple problems with prior methodologies of effecting protein expression. For example, introduced DNA can integrate into host cell genomic DNA at some frequency, resulting in alterations and/or damage to the host cell genomic DNA. Alternatively, the heterologous deoxyribonucleic acid (DNA) introduced into a cell can be inherited by daughter cells (whether or not the heterologous DNA has integrated into the chromosome) or by offspring.

In addition, assuming proper delivery and no damage or integration into the host genome, there are multiple steps which must occur before the encoded protein is made. Once inside the cell, DNA must be transported into the nucleus where it is transcribed into RNA. The RNA transcribed from DNA must then enter the cytoplasm where it is translated into protein. Not only do the multiple processing steps from administered DNA to protein create lag times before the generation of the functional protein, each step represents an opportunity for error and damage to the cell. Further, it is known to be difficult to obtain DNA expression in cells as DNA frequently enters a cell but is not expressed or not expressed at reasonable rates or concentrations. This can be a particular problem when DNA is introduced into primary cells or modified cell lines.

SUMMARY OF THE DISCLOSURE

This summary is meant to provide examples and is not intended to be limiting of the scope of the invention in any way. For example, any feature included in an example of this summary is not required by the claims, unless the claims explicitly recite the feature. Also, the features described can be combined in a variety of ways. Various features and steps as described elsewhere in this disclosure can be included in the examples summarized here.

In one embodiment, a method to determine RNA translatability includes obtaining a pool of RNA molecules, where each RNA molecule is uniquely encoded with a barcoding sequence and each barcoding sequence is flanked by at least one profiling sequence, transfecting a cell or cell lysate with the pool of RNA molecules, performing polysome profiling on the pool of RNA molecules to segregate RNA molecules based on the number of ribosomes bound to the RNA molecule, and isolating a first fraction from the polysome profile to generate a first set of RNA molecules showing a first level of ribosomes bound to the RNA molecules in the set of RNA molecules.

In a further embodiment, the method further includes sequencing the barcode sequence of each RNA molecule in the first set of RNA molecules to identify the presence of each RNA molecule in the first set of RNA molecules.

In another embodiment, the method further includes determining translatability of the RNA molecules associated with each barcode sequence in the fraction by identifying the prevalence of each barcode in the fraction.

In a still further embodiment, the RNA molecules are transfected into a collection of cells.

In still another embodiment, the collection of cells is selected from mammalian cells, yeast cells, bacteria cells, and plant cells.

In a yet further embodiment, the RNA molecules are added to a cell lysate.

In yet another embodiment, polysome profiling comprises adding a cell lysate to a sucrose gradient and centrifuging the sucrose gradient to segregate the RNA molecules.

In a further embodiment again, the barcoding sequence is selected from SEQ ID NOs: 115-1380.

In another embodiment again, the profiling sequence is selected from SEQ ID NOs: 1381-1382.

In a further additional embodiment, the method further includes isolating a second fraction from the polysome profile to generate a second set of RNA molecules showing a second level of ribosomes bound to the RNA molecules in the set of RNA molecules, where the first level and second level represent different amounts of bound ribosomes.

In another additional embodiment, the method further includes sequencing the barcode sequence of each RNA molecule in the first set of RNA molecules and the second set of RNA molecules to identify the presence of each RNA molecule in the first set of RNA molecules and the second set of RNA molecules.

In a still yet further embodiment, isolating a first fraction from the polysome profile includes isolating a plurality of fractions of the polysome profile, where each fraction in the plurality of fractions generates a set of RNA molecules showing a different level of ribosomes bound to the RNA molecules in that set of RNA molecules.

In still yet another embodiment, the method further includes sequencing the barcode sequence of each RNA molecule in each set of RNA molecules to identify the presence of each RNA molecule in each set of RNA molecules.

In a still further embodiment again, the method further includes generating a distribution for each RNA molecule based on the prevalence of each RNA molecule in each fraction.

In still another embodiment again, isolating a first fraction further comprises introducing a known amount of spike-in RNA molecule, wherein the spike-in RNA molecule serves as an internal reference to allow for quantification of the first set of RNA molecules.

In a still further additional embodiment, an RNA molecule for increased translation includes a 5' untranslated region, a 3' untranslated region, and a coding sequence, where the 5' untranslated region is located 5' of the coding sequence and the 3' untranslated region is located 3' of the coding sequence.

In still another additional embodiment, wherein the coding sequence codes for a peptide of interest.

In a yet further embodiment again, the 5' untranslated region is selected from SEQ ID NOs: 1-55 and SEQ ID NOs: 81-111.

In yet another embodiment again, the 3' untranslated region is selected from SEQ ID NOs: 56-80.

In a yet further additional embodiment, the RNA molecule further includes a barcode sequence located 3' of the coding sequence and at least one profiling sequence adjacent to the barcode sequence.

In yet another additional embodiment, the barcode sequence is selected from SEQ ID NOs: 115-1380 and the profiling sequence is selected from SEQ ID NOs: 1381-1382.

In a further additional embodiment again, a method to determine RNA stability includes obtaining a pool of RNA molecules, where each RNA molecule is uniquely encoded with a barcoding sequence and each barcoding sequence is flanked by at least one profiling sequence, treating the pool of RNA molecules under an experimental condition, and isolating the pool of RNA molecules at a specified timepoint to generate a fraction of RNA molecules showing stability under the experimental condition for the specified timepoint.

In another additional embodiment again, the method further includes sequencing the barcode sequence of each RNA molecule in the fraction to identify the presence of each RNA molecule in the fraction of RNA molecules.

In a still yet further embodiment again, the method further includes determining stability of the RNA molecules associated with each barcode sequence in the fraction by identifying the prevalence of each barcode in the fraction.

In still yet another embodiment again, the treating step includes transfecting the pool of RNA molecules into a collection of cells.

In a still yet further additional embodiment, the collection of cells is selected from mammalian cells, yeast cells, bacteria cells, and plant cells.

In still yet another additional embodiment, the treating step includes adding the pool of RNA molecules to a cell lysate.

In a yet further additional embodiment again, the treatment condition is selected from temperature, pH, presence of certain molecules, presence of certain ions, concentration of certain molecules, concentration of certain ions, irradiation, buffer type, and buffer concentration.

In yet another additional embodiment again, the method further includes size selecting for full-length RNA molecules.

In a still yet further additional embodiment again, size selecting includes performing reverse transcription PCR to transcribe a region from each into cDNA, wherein the region is selected from a full-length mRNA, a full-length CDS, a 5'UTR-CDS, a 3'UTR-CDS, and the barcode.

In still yet another additional embodiment, the isolating step further includes isolating the pool of RNA molecules at a second specified timepoint to generate a second fraction of RNA molecules showing stability under the experimental condition for the specified timepoint.

In another further embodiment, isolating the pool of RNA molecules further includes introducing a known amount of spike-in RNA molecule, where the spike-in RNA molecule serves as an internal reference to allow for quantification of the fraction of RNA molecules.

In still another further embodiment, a method for identifying RNA molecules possessing increased translatability and stability includes obtaining a pool of RNA molecules, where each RNA molecule is uniquely encoded with a barcoding sequence and each barcoding sequence is flanked by at least one profiling sequence, assessing translatability of the pool of RNA molecules by transfecting a cell or cell lysate with a first subset of the pool of RNA molecules, performing polysome profiling on the first subset of the pool of RNA molecules to segregate RNA molecules based on the number of ribosomes bound to the RNA molecule, and isolating a fraction from the polysome profile to generate a first set of RNA molecules showing a first level of ribosomes bound to the RNA molecules in the set of RNA molecules, and assessing stability of the pool of RNA molecules by treating a second subset of the pool of RNA molecules under an experimental condition, and isolating a fraction from the second subset the pool of RNA molecules at a specified timepoint to generate a second set of RNA molecules showing stability under the experimental condition for the specified timepoint.

In yet another further embodiment, the method further includes sequencing the barcode sequence of the first set of RNA molecules and the second set of RNA molecules to identify the presence of each RNA molecule in each fraction of RNA molecules.

In another further embodiment again, the method further includes determining translatability and stability of the RNA molecules associated with each barcode sequence in the first set of RNA molecules and the second set of RNA molecules by identifying the prevalence of each barcode in each fraction of RNA molecules.

In another further additional embodiment, the barcoding sequence is selected from SEQ ID NOs: 115-1380.

In yet another further additional embodiment, the profiling sequence is selected from SEQ ID NOs: 1381-1382.

In yet again another further additional embodiment, a method to select for RNA elements includes obtaining a library of RNA molecules, where each RNA molecule comprises a coding sequence, a 5' untranslated region (5'UTR), and a 3' untranslated region (3'UTR), where one of the coding sequence, the 5'UTR, or the 3'UTR comprises a degenerate region, assessing a property of the library of RNA molecules, where the property is selected from translatability, in vivo stability, and in vitro stability, and selecting an RNA molecule from the library of RNA molecules showing increase in the property over other RNA molecules in the library of RNA molecules.

In yet another further additional embodiment again, the method further includes sequencing the selected RNA molecule.

In a yet further additional embodiment, the selected RNA molecule is a pool of RNA molecules.

In yet again another further embodiment, the method further includes reassessing the property of the pool of RNA molecules, and selecting an RNA molecule from the pool of RNA molecules showing increase in the property over other RNA molecules in the pool of RNA molecules.

In again another yet further additional embodiment, the method further includes sequencing the selected RNA molecule from the pool of RNA molecules.

In yet again another yet further additional embodiment, the property is translatability.

In yet another yet further additional embodiment again, the degenerate region is selected from a deletion, a random sequence, an ambiguous sequence, and a truncation.

The foregoing and other objects, features, and advantages of the disclosed technology will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

FIG. 6A illustrates a full view of the heatmap; while FIGS. 6B-6C illustrate enlarged views of the heatmap of FIG. 6A.

FIGS. 8A-8C illustrate exemplary data of correlations between in cell half-life and ribosome load (FIG. 8A), monosome-to-free-subunit ratio (FIG. 8B), and polysome-to-monosome ratio (FIG. 8C).

FIGS. 9A-9B illustrate exemplary data of in cell half-life (FIG. 9A) and ribosome load (FIG. 9B).

FIG. 9C illustrates an exemplary demonstration of how to determine or predict protein expression based on in cell half-life and ribosome load.

DETAILED DESCRIPTION OF THE DISCLOSURE

Turning now to the drawings, systems and methods to enhance RNA translatability and uses thereof, and systems and methods to quantify RNA stability and translatability and uses thereof are provided. Many embodiments provide nucleic acid molecules (e.g., RNA molecules (including messenger RNA (mRNA)), DNA molecules, DNA/RNA hybrid molecules) that allow for an assessment of in vitro, in vivo, in cell, in solution, in storage, and/or any other form of molecular stability. Some embodiments are directed to RNA molecules, including mRNA, with increased translatability and/or stability. Certain embodiments provide RNA molecules used for RNA therapeutics, including vaccines, where one or more of 1) high and sustained expression of RNA (e.g., mRNA), 2) high stability of RNA inside of cells (e.g., in vivo), and 3) high stability of RNA in solution (e.g., in vitro) is desired.

Further embodiments provide methods that provide RNA molecules with increased translatability and/or stability, while additional embodiments provide methods to test translatability and/or stability of RNA molecules. Certain embodiments provide a multiplexed workflow to generate RNA molecules, including mRNA, having increased translatability and/or stability in a single assay. In many embodiments, the RNA molecules of various embodiments are generated via rational design, while certain embodiments generate RNA molecules via iterative selection.

RNA Molecules and Design

As noted above, some embodiments generate RNA molecules via rational design, while others utilize iterative selection. Rational design is a methodology that combines sequence components, such as a 5' UTR, a 3' UTR, and/or a coding region that exist in nature or are synthetically engineered for specific objective (e.g., increased stability or translatability). However, certain embodiments utilize iterative selection to generate RNA molecules, where various sequence components, such as a 5' UTR, a 3' UTR, and/or a coding region, comprise random sequences. Certain embodiments utilizing iterative selection optimize RNA molecules for translatability and/or stability over several rounds of sequence selection (e.g., selecting for sequences showing increased translation or stability).

Figure 1A:
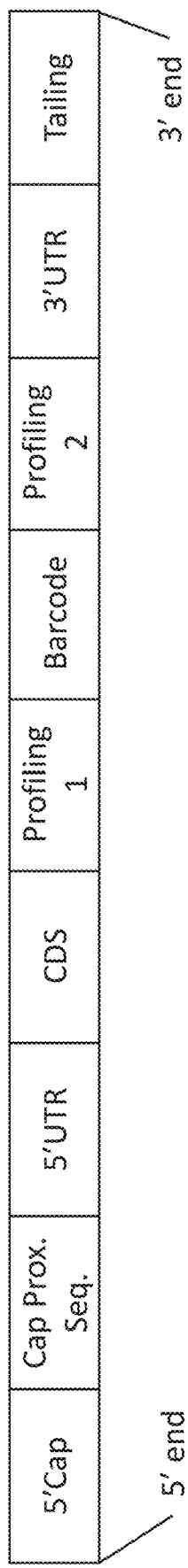
FIG. 1A illustrates a generalized structure of RNA molecules in accordance with various embodiments of the invention.

Turning to FIG. 1A, an exemplary structure for an embodiment of an RNA molecule in accordance with various embodiments is illustrated. Certain embodiments of an RNA molecule possess a 5' cap moiety. Some embodiments utilize a 7-methyl guanosine triphosphate as the cap moiety, but various additional cap sequences are known in the art for a 5' cap moiety. Additional embodiments possess a cap-proximal sequence for an mRNA region located at the 5' end of the mRNA at the 3'end of the 5' cap moiety. Various cap sequences are known in the art for a 5' cap-proximal sequence. Certain embodiments use a small triplet, such GGG as the cap-proximal sequence.

Additional embodiments of an RNA molecule possess a 5' untranslated region (5'UTR) sequence and/or a 3'UTR sequence. Certain embodiments place the 5'UTR near the 5' end of the RNA molecule, while the 3'UTR is located near the 3' end of the molecule. In some embodiments, the 5'UTR is located at the 3' end of a 5' cap moiety, while additional embodiments place the 5'UTR directly at the 5' end without a 5' cap moiety or cap sequence. Similarly, a 3'UTR can be placed at the 3' end of a molecule, while additional embodiments may have a tailing sequence placed 3' of the 3'UTR. Certain embodiments select a 5'UTR and/or a 3'UTR for a variety of factors to increase RNA translatability, stability, and/or other property based on an innate sequence, while others select a 5'UTR and/or a 3'UTR for that may pose improved translatability, stability, and/or other property based on a particular coding sequence of interest. Many possible 5'UTRs and 3'UTRs are known in the art, which are used in various embodiments. Some specific embodiments of rationally designed RNAs select the 5'UTR from natural or modified 5'UTR elements, including SEQ ID NOs: 1-55. And, certain specific embodiments select the 3'UTR from SEQ ID NOs: 56-80. Tables 1 and 2 list various 5'UTRs and 3'UTRs, respectively, with their respective SEQ ID NOs.

TABLE 1

5'UTR Sequences

| Name: | SEQ ID NO: |
|---|---|
| SynJ | 1 |
| hHBB30 | 2 |
| CYP2E1 | 3 |
| CYBA | 4 |
| mRpl18a | 5 |
| RpS25 | 6 |
| scrUTR | 7 |
| TEV | 8 |
| hHBB | 9 |
| APOA2 | 10 |
| TOP_hHBB | 11 |
| C3 | 12 |
| hHBB_pA | 13 |
| TCV | 14 |
| PoV_pA_scrUTR | 15 |
| TMV | 16 |
| PoV_pA_hHBB | 17 |
| RpL38 | 18 |
| CoV-2-TTG-dSL4-5 | 19 |
| hACTB | 20 |
| RpL31 | 21 |
| mRpl18a_hHBB | 22 |
| DEN2 | 23 |
| RBCS3B | 24 |
| mActb | 25 |
| mActb_inv | 26 |
| TEV_CERT_hHBB | 27 |
| Tubb2b | 28 |
| P4_hACTB | 29 |
| hCOL1A2 | 30 |
| BYDV | 31 |
| CoV-2-TTG-dSL5 | 32 |
| P4_mActb | 33 |
| P4_mActb_inv | 34 |
| CoV-2-TTG-dSL5A-C | 35 |
| CoV-2-TTG-dSL1-3 | 36 |
| mRpl18a_P4_mActb | 37 |
| TEV_P4_mActb | 38 |
| P4_TEV_mActb | 39 |
| CoV-2-TTG-dSL4-full | 40 |
| CoV-2-TTG-dSL4-1 | 41 |
| CoV-2-TTG-dSL5A | 42 |
| CoV-2-TTG-TTGfull-dSL1-3 | 43 |
| CoV-2-TTG-dSL5B,C | 44 |
| CoV-2-TTG-dSL1 | 45 |
| CoV-2-TTG-dSL4-2 | 46 |
| CoV-2-TTG-dSL2 | 47 |
| CoV-2-TTG-dSL3 | 48 |
| CoV2 | 49 |
| CoV2_TTG | 50 |
| CoV2_P4 | 51 |
| CoV-2-TTG-TTGfull | 52 |
| mHoxa9_IRES | 53 |
| HCV_IRES | 54 |
| RBCS1A | 55 |

TABLE 2

3'UTR Sequences

| Name: | SEQ ID NO: |
|---|---|
| SINV_URE | 56 |
| CYBA | 57 |
| PV | 58 |
| hHBA1 | 59 |
| CYBA_1.5x | 60 |

TABLE 2-continued

3'UTR Sequences

| Name: | SEQ ID NO: |
|---|---|
| BMV | 61 |
| hHBB | 62 |
| AMV | 63 |
| ENE_Wilusz | 64 |
| ENE_Weissman | 65 |
| BYDV | 66 |
| TSV | 67 |
| hHBB_F30Pepper | 68 |
| P4P6 | 69 |
| TCV | 70 |
| hHBBx2 | 71 |
| CrPV | 72 |
| SINV | 73 |
| CoV2 | 74 |
| DV | 75 |
| RV | 76 |
| WPRE | 77 |
| hActb | 78 |
| mActb | 79 |
| hCOL1A2 | 80 |

Figure 1B:
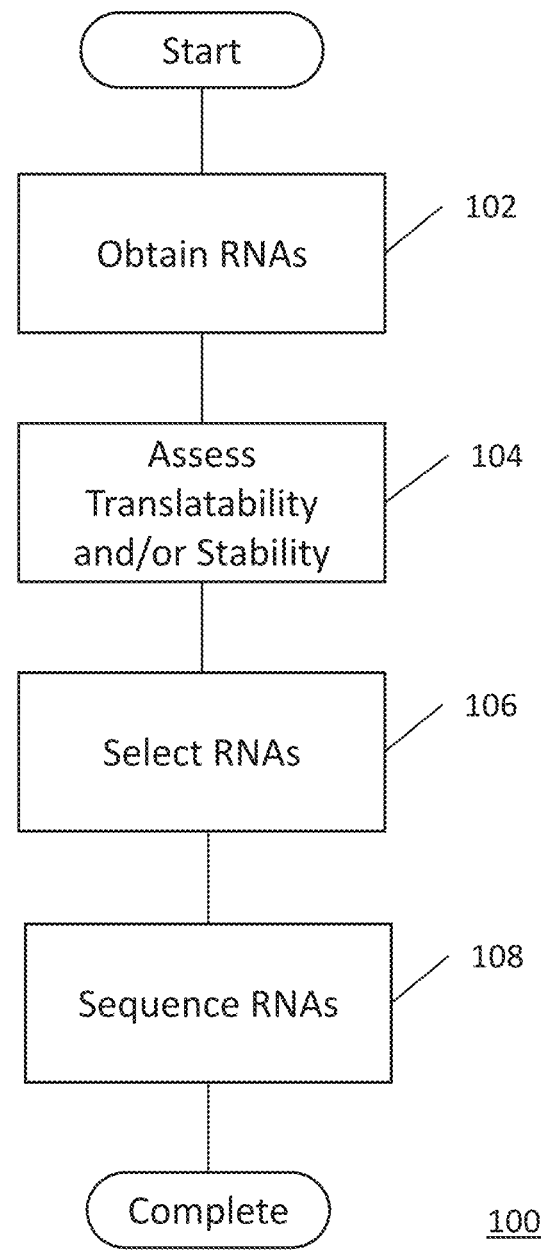
FIG. 1B illustrates a method for performing iterative selection of RNA elements to enhance translatability and/or stability in accordance with various embodiments of the invention.

FIG. 1B illustrates a method 100 for iteratively selecting elements to increase RNA translatability and/or stability. Such embodiments identify sequences or segments of an expression-affecting region (e.g., 5'UTR, 3'UTR, and/or coding region) that increase translatability, stability, and/or other property of the RNA molecule.

At 102, various embodiments obtain a library of RNA molecules. In certain embodiments, the library comprises RNA molecules with degenerate sequences in regions that affect RNA expression. In certain embodiments, the degenerate expression-affecting region are truncated at its 5'- and/or 3'-end. In some embodiments, the degenerate expression-affecting region contains internal deletions, such that the 5'- and/or 3'-end remain intact, but the overall region is smaller. In certain embodiments, the degenerate sequences are random, ambiguous, and/or mutated sequences to identify specific bases that may allow for an outsized role in translatability and/or stability.

At 104, many embodiments assess stability and/or translatability of the molecules. Various methods to assess translatability and/or stability are described herein. At 106, certain embodiments select for molecules having a minimum level of translatability and/or stability, such as through selection of a specific fraction of stability and/or translatability. For example, many embodiments select for fractions having high levels of stability (e.g., at longer time points) and/or translatability (e.g., higher polysome fractions).

Upon assessing stability and/or translatability, certain embodiments sequence the selected for molecules at 108. Sequencing the selected molecules identifies the specific sequences that correlate to the tested characteristic (e.g., translatability and/or stability).

It should be noted that many embodiments may perform several features multiple times, such as the assessing 104 and selecting 106 features, in order to identify the sequences having the highest rates of translatability and/or stability. For example, numerous embodiments take the selected for molecules (e.g., ones having high levels of translatability and/or stability) and reassess the translatability and/or stability of these molecules, selecting for high levels of high levels of translatability and/or stability. Various embodiments repeat the assessing 104 and selecting 106 features 2 times, 3 times, 4 times 5 times, 6 times, 7 times, 8 times, 9 times, 10 times, or more times to identify molecules having the highest levels of translatability and/or stability. Additionally, various embodiments repeat sequencing 108, such as after each selection 106, or just after every second selection 106.

Methods, such as method 100, allow for iterative selection of expression-affecting regions to further increase translatability, stability, and/or other property. Some exemplary embodiments utilize a pool 5'-UTR selected from SEQ ID NOs: 81-111. Table 3 identifies specific pools of 5'UTR sequences for iterative selection.

TABLE 3

5'UTR Sequence Pools

| Pool 1 | SEQ ID NOs: 81-90 |
|---|---|
| Pool 2 | SEQ ID NOs: 91-101 |
| Pool 3 | SEQ ID NOs: 102-106 |
| Pool 4 | SEQ ID NOs: 107-111 |

Returning to FIG. 1A, many embodiments of an RNA molecule possess a coding sequence, or CDS, located 3' from the 5'UTR, and 5' of the 3'UTR. In many embodiments, the CDS begins (e.g., at its 5'-end) with a start codon (e.g., the canonical AUG and/or any other codon known to begin translation). In many embodiments, the CDS terminates (e.g., at its 3'-end) with a stop codon. In various embodiments the stop codon is a canonical stop codon (e.g., UAG, UAA, UGA), while further embodiments comprise a non-canonical stop codon or another sequence shown to terminate translation. Certain embodiments comprise more than one stop codon in the CDS.

The coding sequence is a designed sequence of interest to encode a protein or peptide of interest. In certain embodiments, the coding sequence encodes an epitope or other antigen to induce an immune response, thus allowing creation of a vaccine. In various embodiments, the protein or peptide of interest is used as a therapeutic directly, such that the protein or peptide of interest replaces or supplements a dysfunctional protein or peptide. In some embodiments, the protein or peptide of interest corrects for dysfunction of another protein or peptide. While protein coding sequences are described in the context of this exemplary embodiment, additional embodiments possess sequences for non-coding RNAs, such as RNAs that guide genome editing and/or coat chromatin. Various embodiments possess a CDS encoding a reporter gene; for example, nanoluciferase ("Nluc", SEQ ID NO: 112), green fluorescence protein ("GFP", SEQ ID NO: 113), and/or any other reporter gene of interest. Various embodiments encode a therapeutic, such as a multi-epitope vaccine ("MEV", SEQ ID NO: 114).

Additional embodiments of an RNA molecule include a barcode to identify particular molecules based on unique sequences. Many barcode schemes are known in the art and range from 2 to 12 or more nucleotides. In many embodiments, the barcodes are 6-9 nucleotides in length. Certain embodiments select one or more barcodes from SEQ ID NOs: 115-1380.

To read barcodes, an RNA molecule can include one or more profiling sequences that can be used by PCR primers or sequencing primers to amplify and/or sequence the barcode region. In some embodiments profiling sequences are located at the 5' and/or 3' end of a barcode. In many embodiments, profiling sequences flank the barcode. In various embodiments profiling sequences are selected from profiling sequence 1 (SEQ ID NO: 1381) and profiling sequence 2 (SEQ ID NO: 1382).

As noted above, some embodiments of an RNA molecule possess a tailing sequence located at the 3' end of a molecule. In various embodiments the tailing sequence is used to add a poly-A tail or other structural sequence to an RNA molecule. In some embodiments, the tailing sequence is selected as SEQ ID NO: 1383.

Structures, such as those described above in regard to FIG. 1 allow for modular and combinatorial testing of various 5'UTRs, CDSs, and 3'UTRs.

Methods of Assessing RNA Translatability

Figure 2:
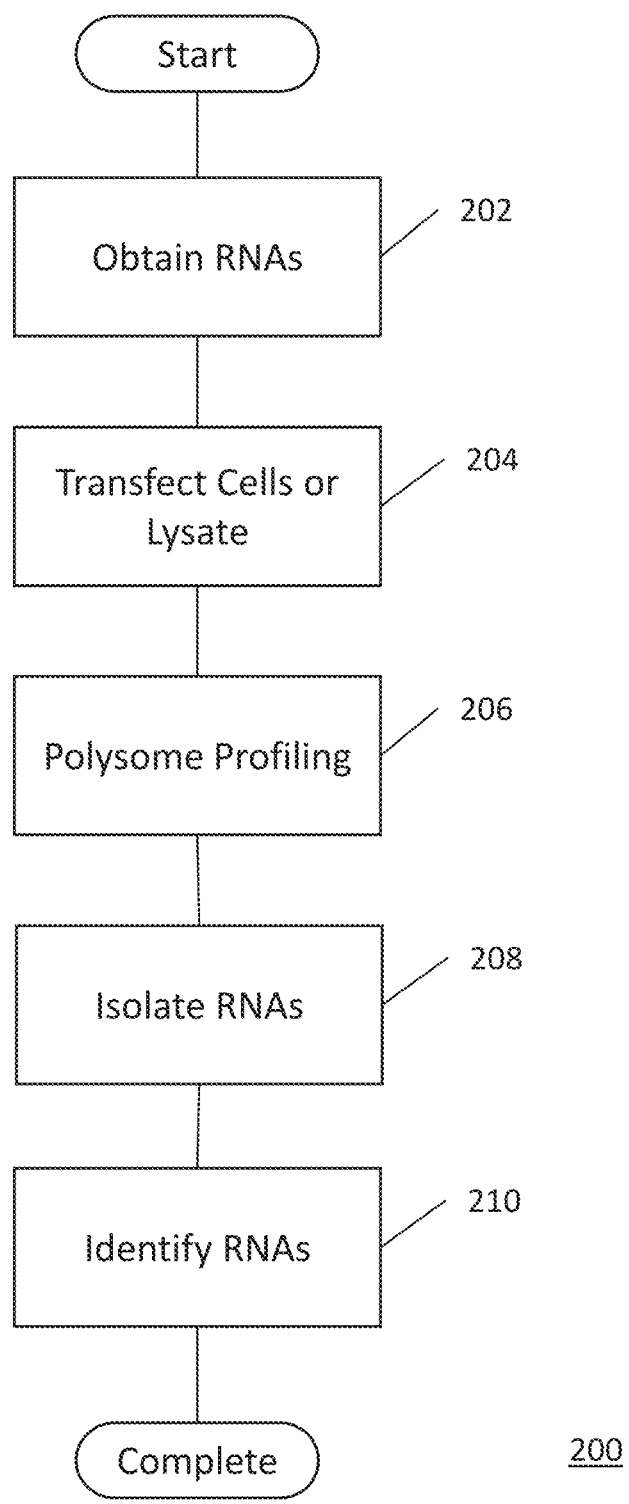
FIG. 2 illustrates a method to screen RNAs for increased translatability in accordance with various embodiments of the invention.

Certain embodiments assess translatability of RNA molecules, such as those described elsewhere herein. An exemplary embodiment of a method 200 to assess translatability is illustrated in FIG. 2. In method 200, an RNA molecule is obtained at 202 of many embodiments. In certain embodiments, the RNA molecule is generated via in vitro transcription. Additionally, certain embodiments generate an RNA transcript and/or further modify RNA transcripts to be used for translation (e.g., including a 5' cap and/or a 3' polyA tail). Some embodiments obtain DNA templates from a commercial vendor. In various embodiments, polymerase chain reaction (PCR) is used to amplify a full-length DNA template for the RNA molecule. Additional embodiments assess amplicon quality via electrophoresis, including gel (agarose and/or polyacrylamide) and/or capillary electrophoresis (e.g., ABI 3700 and/or Agilent Bioanalyzer). Further embodiments transcribe DNA amplicons to RNA using a DNA-dependent RNA polymerase. Certain embodiments perform the in vitro transcription using commercial kits, including Thermo's T7 MEGAScript kit. Various embodiments modify the RNA transcripts with a 5' cap and/or polyA tail. These modifications can be accomplished using kits, such as the Cellscript kit and/or any other applicable and commercially available kit. Additional cleanups can be accomplished at various stages (e.g., after PCR, after transcription, and/or after modification), using columns or reagents, such as Thermo's MEGAClear columns. And, quality of the transcribed and/or modified RNAs can be accomplished via electrophoresis, including gel and capillary electrophoresis. Further embodiments quantify the RNA pool via various known means, such as spectrophotometry, fluorometry, or and/or any other known method for quantifying nucleic acids.

In various embodiments, the RNA molecule is obtained as a pool of RNA molecules, where each unique RNA sequence in the pool comprises a unique barcode, such as described herein. In certain embodiments, the RNA molecules within the pool are approximately the same length. In certain embodiments, the RNA molecules within the pool vary in length.

Various embodiments transfect RNA transcripts into cells or add the transcripts to a cellular lysate at 204. In certain embodiments, transfection occurs on cultured cells or tissue, including mammalian cells, while other embodiments use yeast, bacteria, or plant cells. Some specific embodiments transfect HEK293T cells. Various embodiments incubate the transfected cells to allow for translation of the RNAs. Incubation can last between 1 hour and several days (e.g., 7-10 days) at temperatures and/or conditions to encourage cellular growth and translation. Culture media can include antibiotics or other selective reagents to prevent growth of non-transfected cells and/or contamination. Certain embodiments utilize a cellular lysate as a proxy of in vivo stress on RNA. In such embodiments, cultured cells are lysed via a known method, such as sonication, hydrodynamic stress, or any other method to generate cellular lysate. In various embodiments, the RNA molecule(s) are added to the lysate and allowed to react for a period of time, such as between 1 hour and several days (e.g., 7-10 days) and at temperatures commensurate with the operating temperature for the RNA (e.g., average body temperature, 37° C.).

At 206, certain embodiments perform polysome profiling. In various embodiments, the polysome profiling separates RNA molecules or transcripts based on the number of ribosomes located on, or bound to, a transcript or RNA molecule. As ribosomes are the machinery for translation, the number of ribosomes located on a transcript is indicative of the translatability of a particular transcript.

In certain embodiments, polysome profiling uses a sucrose gradient (e.g., a continuous sucrose gradient) to fractionate RNA molecules based on the number of ribosomes (e.g., polysomes) located on the transcript. Various embodiments perform polysome profiling by lysing transfected cells and applying the lysate to a column containing a sucrose gradient. In embodiments, where RNA transcripts are applied to a cellular lysate, the lysate is directly added to a sucrose gradient column. Centrifugation is applied to the column to separate transcripts based on the number of ribosomes attached to a transcript.

At 208, many embodiments isolate or extract one or more fractions of RNA molecules from the polysome profile. In certain embodiments, the fractions or isolated from the sucrose gradient. In various embodiments, the fractions are isolated as slices, drops, and/or other method of obtaining a fraction from a sucrose gradient. Actively translating RNA molecules have a higher number of ribosomes associated with them and are found in polysomal fractions (e.g., more ribosomes bound to the RNA molecule) whereas non-translating/poorly-translating RNA molecules are present in a free RNA fraction or associated with ribosomal subunits (e.g., 40S ribosomal subunit). In certain embodiments, fractions representing higher amounts of ribosomes bound to RNA are isolated, while some embodiments isolate fractions representing a range of ribosomes bound to RNA in order to identify a distribution of ribosomes present for a particular transcript sequence. RNA molecules from an isolated fraction can be cleaned up via known procedures or kits, including columns.

Certain embodiments introduce a known amount of one or more RNA molecules as a spike-in. Spike-ins serve as an internal reference to allow for quantification of molecules within the assessed RNA library. Such spike-ins are unique RNA molecules that are not present in the analyzed RNA library. The spike-ins can be similar in length to the molecules in the library, and/or possess unique sequences or barcodes.

Various embodiments identify the RNA molecules located in the one or more fractions based on their barcodes at 210. As noted above in relation to FIG. 1, many embodiments of RNA molecules contain a barcode sequence (e.g., SEQ ID NOs: 115-1360). The profiling sequences flanking the barcodes (e.g., SEQ ID NOs: 1381-1382) can be used to amplify the barcode or can be used as sequencing primers for barcoding reads of the RNA molecules of certain embodiments. Further embodiments utilize hybridization probes, quantitative PCR (qPCR), or any other known method with or without pooling strategies to identify which RNAs are present in each fraction.

Methods of Assessing In Vivo or In-Cell RNA Stability

Figure 3:
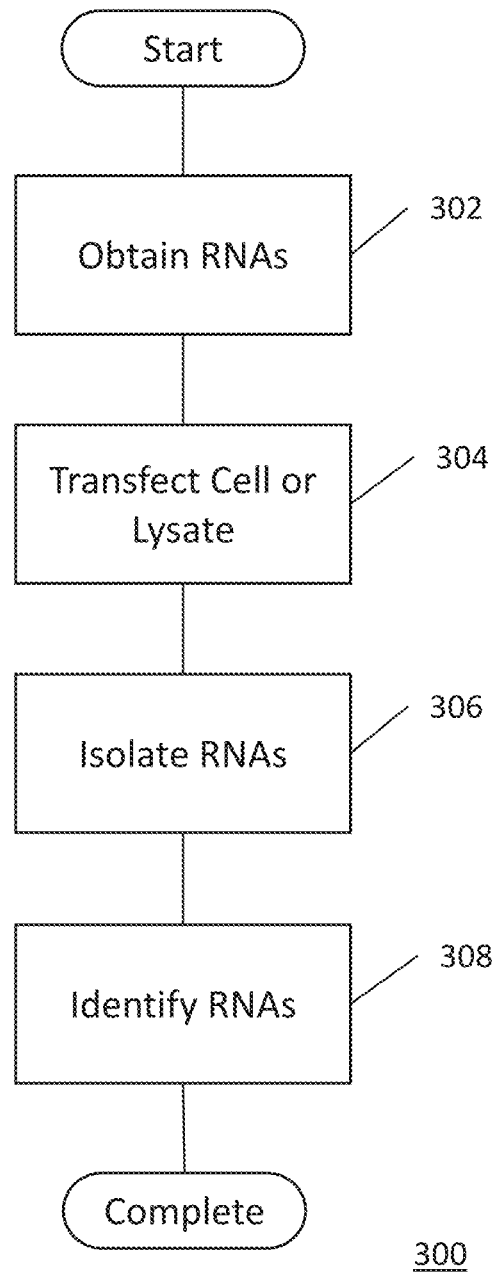
FIG. 3 illustrates a method to screen RNAs for increased in vivo stability in accordance with various embodiments of the invention.

Certain embodiments assess the stability of RNA molecules, including stability within in vivo and in vitro environments. An exemplary embodiment of a method 300 to assess stability is illustrated in FIG. 3. In method 300, RNA is obtained at 302. Obtaining RNA at 302 can be accomplished via many methods, including such steps as described in regard to method 200 (FIG. 2), including the obtention of a pool of RNA molecules, where each unique RNA sequence is identifiable by a unique barcode.

Various embodiments transfect RNA transcripts into cells or add the transcripts to a cellular lysate at 304. In certain embodiments, transfection occurs on cultured cells or tissue, including mammalian cells, while other embodiments use yeast, bacteria, or plant cells. Some specific embodiments transfect HEK293T cells. Various embodiments incubate the transfected cells. Incubation can last between 1 hour and several days (e.g., 7-10 days) at temperatures and/or conditions to encourage cellular growth. Culture media can include antibiotics or other selective reagents to prevent growth of non-transfected cells and/or contamination. Certain embodiments utilize a cellular lysate as a proxy of in vivo stress on RNA. In such embodiments, cultured cells are lysed via a known method, such as sonication, hydrodynamic stress, or any other method to generate cellular lysate. Then, the RNAs are added to the lysate and allowed to react for a period of time, such as between 1 hour and several days (e.g., 7-10 days) and at temperatures commensurate with the operating temperature for the RNA (e.g., average body temperature, 37° C.).

At 306, certain embodiments isolate RNAs based on in-cell stability. In various embodiments, RNAs are isolated from transfected cells, while some embodiments isolate the RNAs from a cellular lysate. Certain embodiments isolate RNA from transfected cells at various time points (e.g., after 1 hour, 2 hours, 3 hours, 6 hours, 12 hours, 24 hours, etc.) to create time-based fractions of RNAs. Based on the relative amounts of an RNA at the different timepoints, assessment of RNA stability can be derived, and a RNA half-life can be calculated. Additionally, isolated RNA molecules can be cleaned up via known procedures or kits, including isolation protocols, kits, columns, or any other known method for isolating RNA from cells or a lysate.

Some embodiments select for stable RNAs by performing reverse transcription PCR (RT-PCR) to amplify long, full length RNA regions, for example the full-length mRNA, full-length CDS, 5' UTR-CDS, 3' UTR-CDS, or any other length covering functional region, or only the barcode region, into complimentary DNA (cDNA). By creating cDNAs, downstream amplifications can utilize DNA-dependent polymerases to create sequencing libraries or other molecules for analysis. Such embodiments select for full length or any longer functional length of RNAs rather than RNAs that may have been hydrolyzed but may still be of sufficient length that electrophoresis or other methods do not remove them.

Certain embodiments introduce a known amount of one or more RNA molecules as a spike-in. Spike-ins serve as an internal reference to allow for quantification of molecules within the assessed RNA library. Such spike-ins are unique RNA molecules that are not present in the analyzed RNA library. The spike-ins can be similar in length to the molecules in the library, and/or possess unique sequences or barcodes.

Various embodiments identify the RNAs based on their barcodes at 308. As noted above in relation to FIG. 2, many embodiments of RNA molecules contain a barcode sequence (e.g., SEQ ID NOs: 115-1380). The profiling sequences flanking the barcodes (e.g., SEQ ID NOs: 1381-1382) can be used to amplify the barcode or can be used as sequencing primers for barcoding reads of the RNA molecules of certain embodiments. Further embodiments utilize hybridization probes, quantitative PCR (qPCR), or any other known method with or without pooling strategies to identify which RNAs are present in timepoint based fractions.

Determination of In Vitro or in Solution RNA Stability

Figure 4:
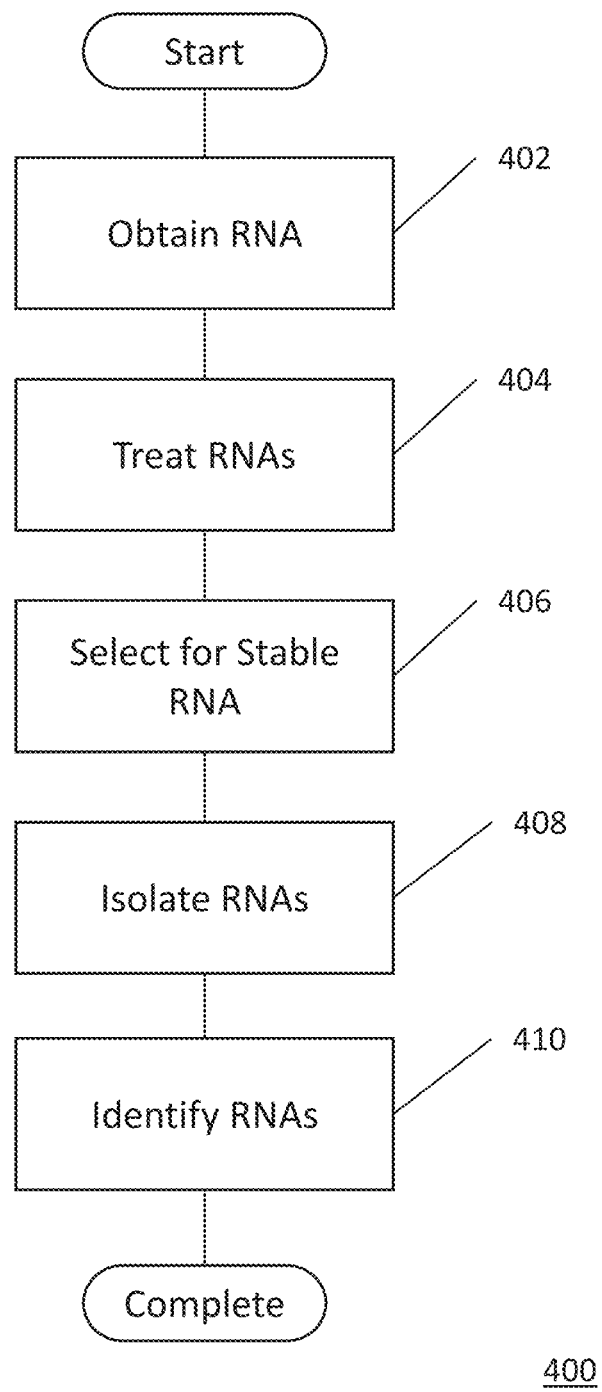
FIG. 4 illustrates a method to screen RNAs for increased in vitro stability in accordance with various embodiments of the invention.

An additional challenge for RNA therapeutics, including vaccines, include the stability in storage, such as between manufacture and actual treatment or delivery to an individual. Such stability is referred to as in vitro stability, as it emphasizes stability in non-biological environments, such as in vials, syringes, or other method of storage. Various embodiments provide a method to measure in vitro stability of RNAs. Turning to FIG. 4, a method 400 to determine in vitro RNA stability in accordance with various embodiments is illustrated. Within method 400, RNA is obtained at 402. Obtaining RNA at 402 can be accomplished via many methods, including such steps as described in regard to method 200 (FIG. 2), including the obtention of a pool of RNA molecules, where each unique RNA sequence is identifiable by a unique barcode.

At 404 of many embodiments, the RNA pool is treated or subjected to an experimental condition. The experimental conditions include any condition that may cause degradation of an RNA molecule in a storage situation, including (but not limited to) temperature, pH, presence of certain molecules and/or ions, concentration of certain molecules and/or ions, irradiation, time, buffer type, buffer concentration, and/or any other condition that can affect RNA stability. Such conditions are meant to reproduce actual conditions that can induce one or more hydrolytic events within the RNA molecules. A hydrolytic event, in accordance with various embodiments, causes a break within the RNA molecule, resulting in a broken or incomplete RNA molecule. Incomplete or broken RNA molecules may be insufficient for use as a therapeutic, as they may be prone to degradation or ineffective in protein production, thus incomplete or broken RNA molecules may limit the efficacy of the molecule as a therapeutic.

Further embodiments further select for stable RNAs in the pool at 406. In some embodiments, the selection occurs by size selecting for full length RNAs, such as through electrophoresis, including (but not limited to) agarose gel electrophoresis, polyacrylamide electrophoresis, and capillary electrophoresis.

Some embodiments select for stable RNAs by performing reverse transcription PCR (RT-PCR) to amplify long RNA regions, for example the full-length mRNA, full-length CDS, 5' UTR-CDS, 3' UTR-CDS, or any other length covering functional region, or only the barcode region, into complimentary DNA (cDNA). By creating cDNAs, downstream amplifications can utilize DNA-dependent polymerases to create sequencing libraries or other molecules for analysis. Such embodiments select for full length or any longer functional length of RNAs rather than RNAs that may have been hydrolyzed but may still be of sufficient length that electrophoresis or other methods do not remove them.

Certain embodiments introduce a known amount of one or more RNA molecules as a spike-in. Spike-ins serve as an internal reference to allow for quantification of molecules within the assessed RNA library. Such spike-ins are unique RNA molecules that are not present in the analyzed RNA library. The spike-ins can be similar in length to the molecules in the library, and/or possess unique sequences or barcodes.

Many embodiments isolate RNAs based on in vitro or in solution stability at 408. Certain embodiments isolate RNA from a solution at various time points (e.g., after 1 hour, 2 hours, 3 hours, 6 hours, 12 hours, 24 hours, etc.) to create time-based fractions of RNAs from a solution. Based on the amount of an RNA at the timepoint 0, relative assessment of RNA stability can be derived, and a RNA half-life can be calculated. Additionally, isolated RNA molecules can be cleaned up via known procedures or kits, including isolation protocols, kits, columns, or any other know method for isolating RNA from cells or a lysate.

At 410, stable RNAs are identified. In various embodiments, the undigested or gel-extracted RNAs are sequenced using the barcode to identify the particular molecules that are stable. In many embodiments, cDNAs created in 406 are utilized as templates to create a sequencing library to avoid the amplification of RNAs that may be near full length.

Figure 5A:
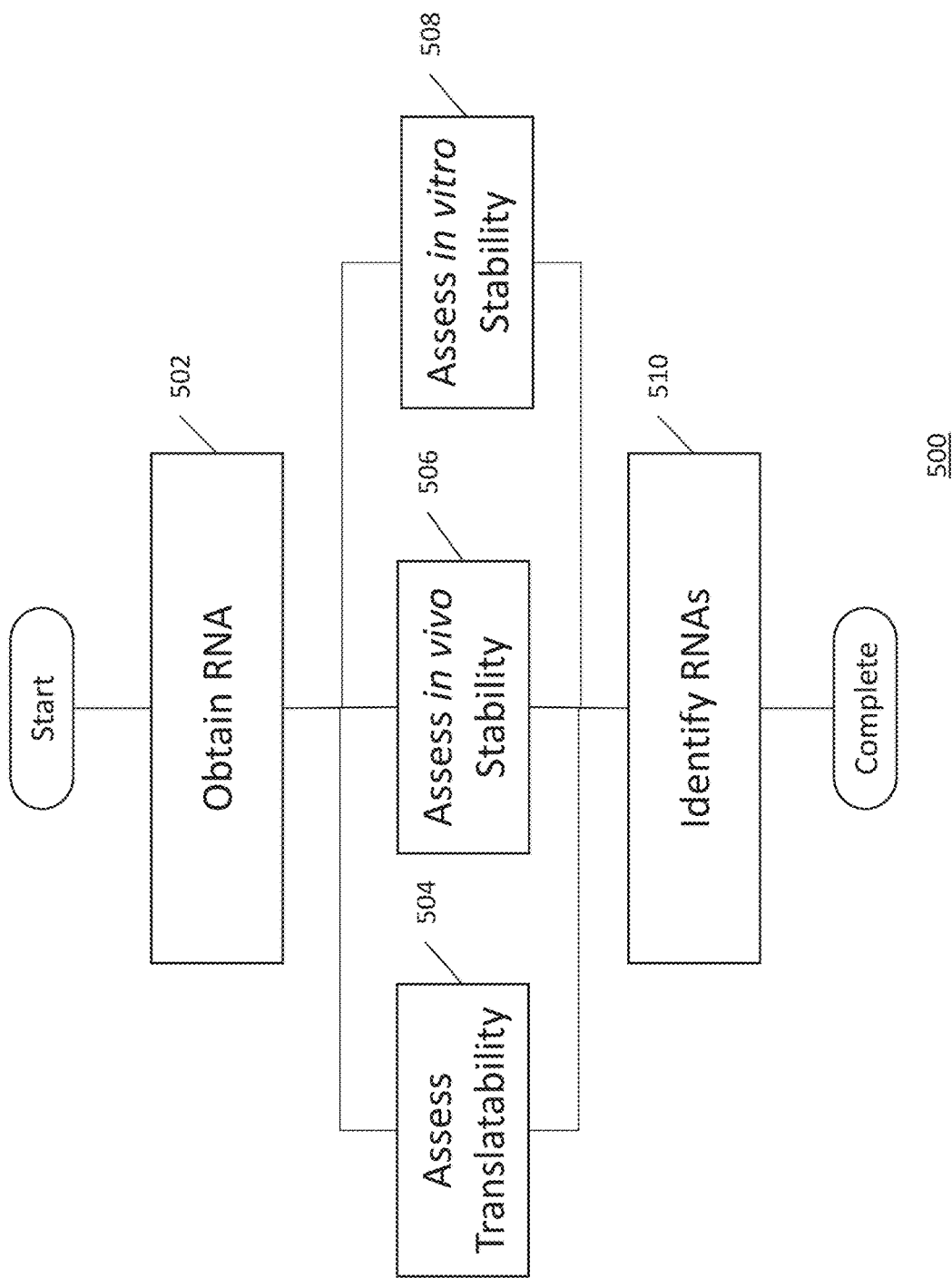
FIG. 5A illustrates a method to screen a pool of RNAs for stability and/or translatability in accordance with various embodiments of the invention.

Identifying RNAs Having Enhanced Translatability, Stability, and/or Other Property Turning to FIG. 5A, certain embodiments are capable of simultaneously assessing one or more of translatability, stability, and/or any other property. Such embodiments assess one or more of translatability, in vivo (or in cell) stability, in vitro (or in solution) stability, and/or any other property. Within method 500, RNA is obtained at 502. Obtaining RNA at 502 can be accomplished via many methods, including such steps as described in regard to method 200 (FIG. 2), including the obtention of a pool of RNA molecules, where each unique RNA sequence is identifiable by a unique barcode. Many embodiments perform one or more of assessing translatability 504, assessing in vivo (or in cell) stability 506, and/or assessing in vitro (or in solution) stability 508. Assessing translatability 504 can be performed via methods, such as method 200 (FIG. 2), while in vivo stability 506 can be performed via method 300 (FIG. 3), and assessing in vitro stability can be performed via method 400 (FIG. 4). Upon obtaining fractions from the one or more of assessing translatability 504, assessing in vivo stability 506, and/or assessing in vitro stability 508, various embodiments can identify RNAs at 510.

Figure 5B:
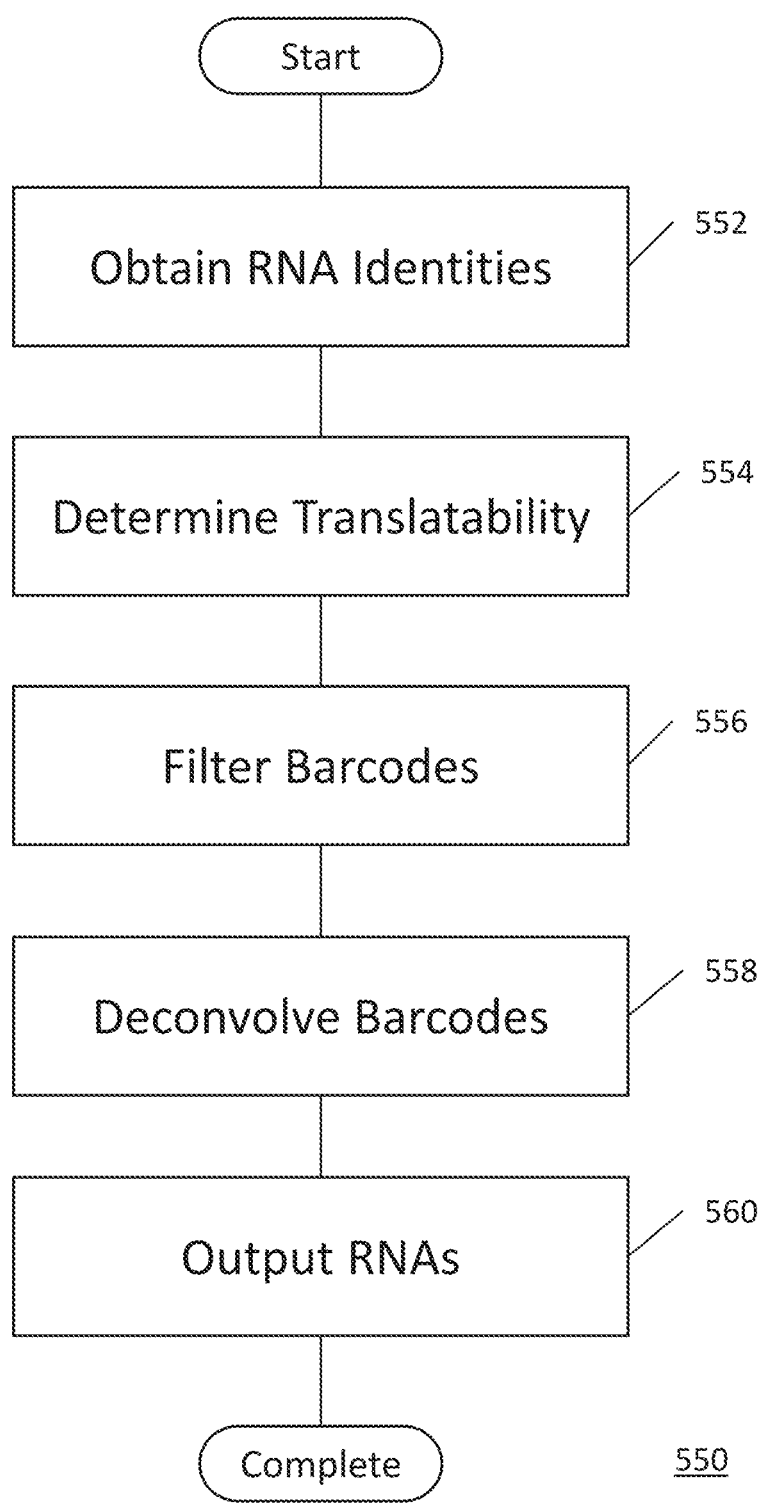
FIG. 5B illustrates a method to identify RNAs possessing increased translatability and/or stability in accordance with various embodiments of the invention.

Turning to FIG. 5B, various embodiments identify RNA molecules possessing increased translatability in method 550. At 552, many embodiments obtain identities of RNA molecules present in various fractions of translatability (e.g., RNAs assessed via methods 200, 300, 400, and/or 500). In various embodiments, these identities include the barcode or barcodes that identify each of the RNA molecules in a fraction and a read count of each barcode in each fraction.

At 554, various embodiments determine the translatability of each RNA molecule by identifying prevalence of each barcode in each fraction. Certain embodiments perform statistical analyses to relative prevalence of the barcode in each fraction. The presence of RNAs in fractions correlating to more ribosomes, indicate increased translatability of that particular RNA molecule as compared to other fractions across the whole polysome profile gradient.

Some embodiments filter RNA molecules based on particular characteristics at 556. Particular characteristics may be specific cutoffs, minimum levels of translatability, or a statistical distribution of a particular barcode. For example, certain embodiments may select barcodes that have a narrower distribution with a lower average ribosomal load (e.g., fewer ribosomes on RNA molecules), while other embodiments may select for a higher average with a broader overall distribution.

Various embodiments deconvolve the barcodes at 558, where deconvolution involves matching the specific RNA sequence or sequence name with the barcode sequence comprised within that RNA molecule.

Additional embodiments output results of translatability, stability, and/or other property at 560. Certain embodiments provide lists of each of the sequences providing a specific cutoff or parameter for minimum translatability, stability, and/or other property. Various embodiments produce a graphical display or visualization, such as a dot plot, heat map, or other graph or chart to visualize stability (e.g., in vivo, in vitro, in cell, in solution, etc.), translatability, and/or any other property of a particular RNA molecule.

Additional embodiments output results of predicted protein expression at a given time or total protein expression over time, from experimentally determined stability and translatability. For this, additional embodiments can use modelling of the empirical data to estimate the predicted protein expression in a pool of hundreds of different RNA molecules based on measurements of a selected number of RNA designs.

Enhanced Translatability of RNA Molecules

Figure 6A:
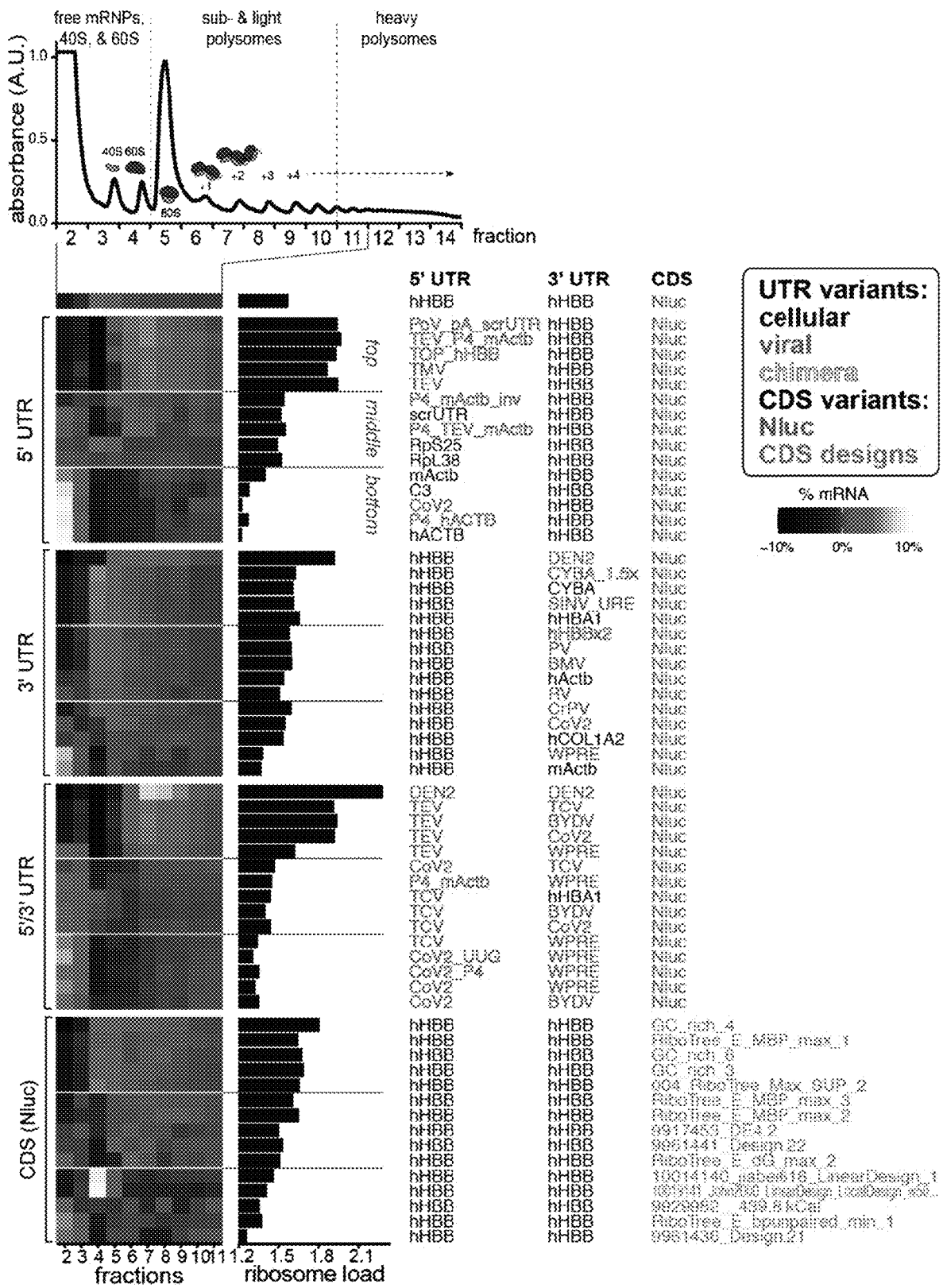
FIGS. 6A-6C illustrate exemplary data of a heatmap showing RNA presence in various fractions after polysome profiling.
Figure 6B:
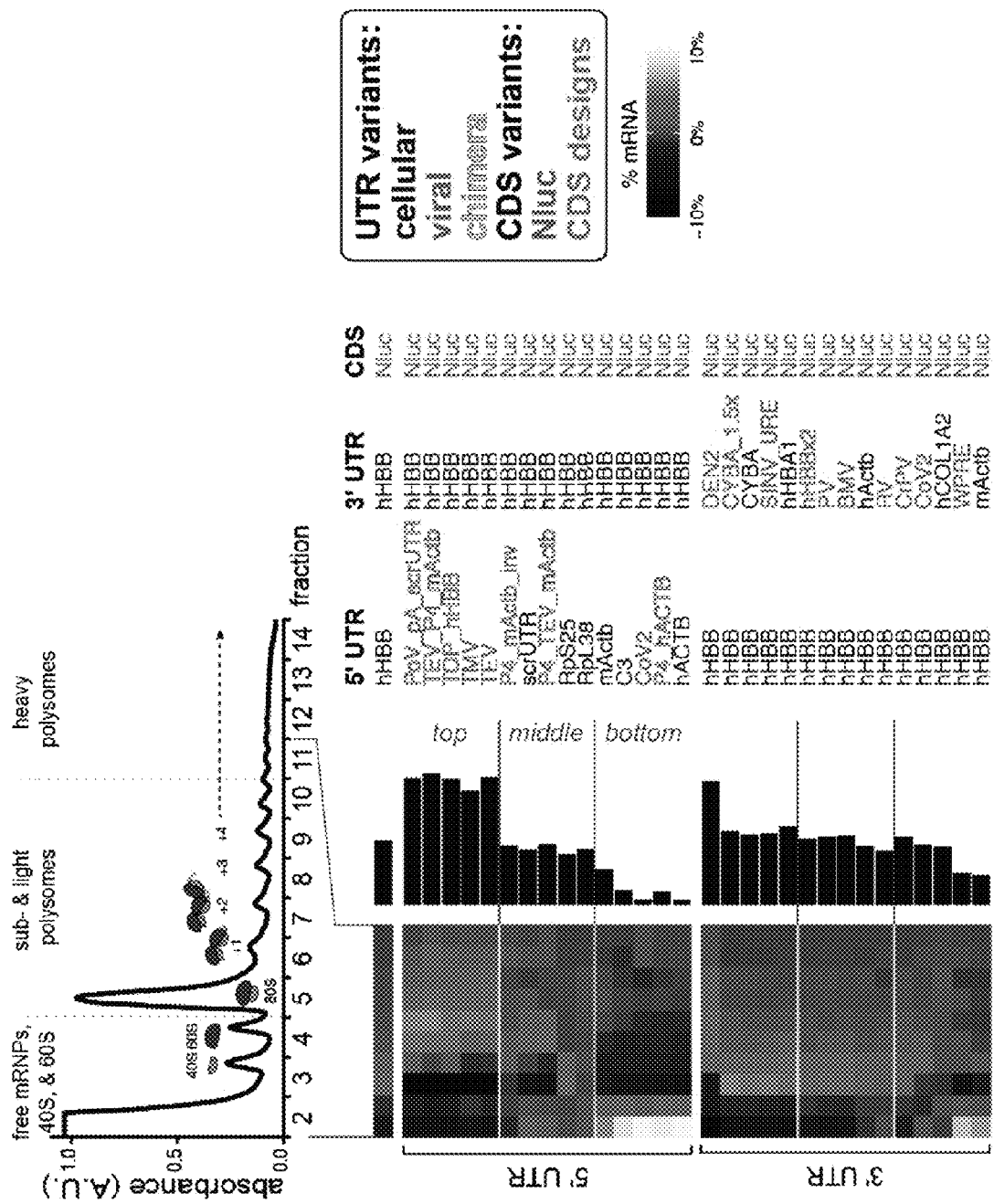
Figure 6C:
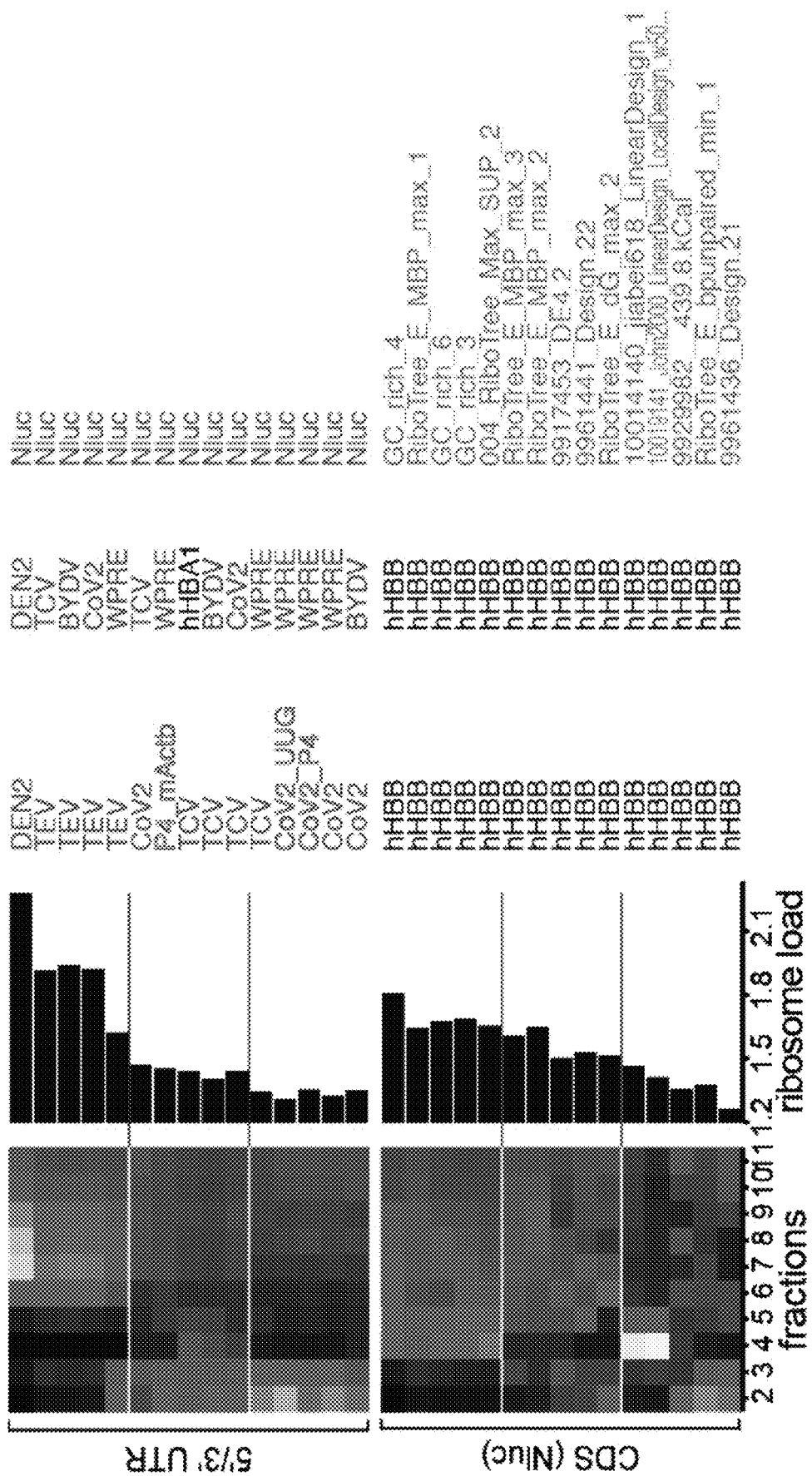

Turning to FIGS. 6A-6C, exemplary results of embodiments showing translation efficiency are illustrated, where FIG. 6A illustrates a heatmap and FIGS. 6B-6C show enlarged portions of FIG. 6A. FIGS. 6A-6C illustrate the relative prevalence of 64 unique RNA molecules in accordance with various embodiments based on polysome fraction. Darker cells indicate a lower relative prevalence of the molecule in a particular fraction, while lighter colors indicate a higher relative prevalence of the molecule in a particular fraction.

Figure 7A:
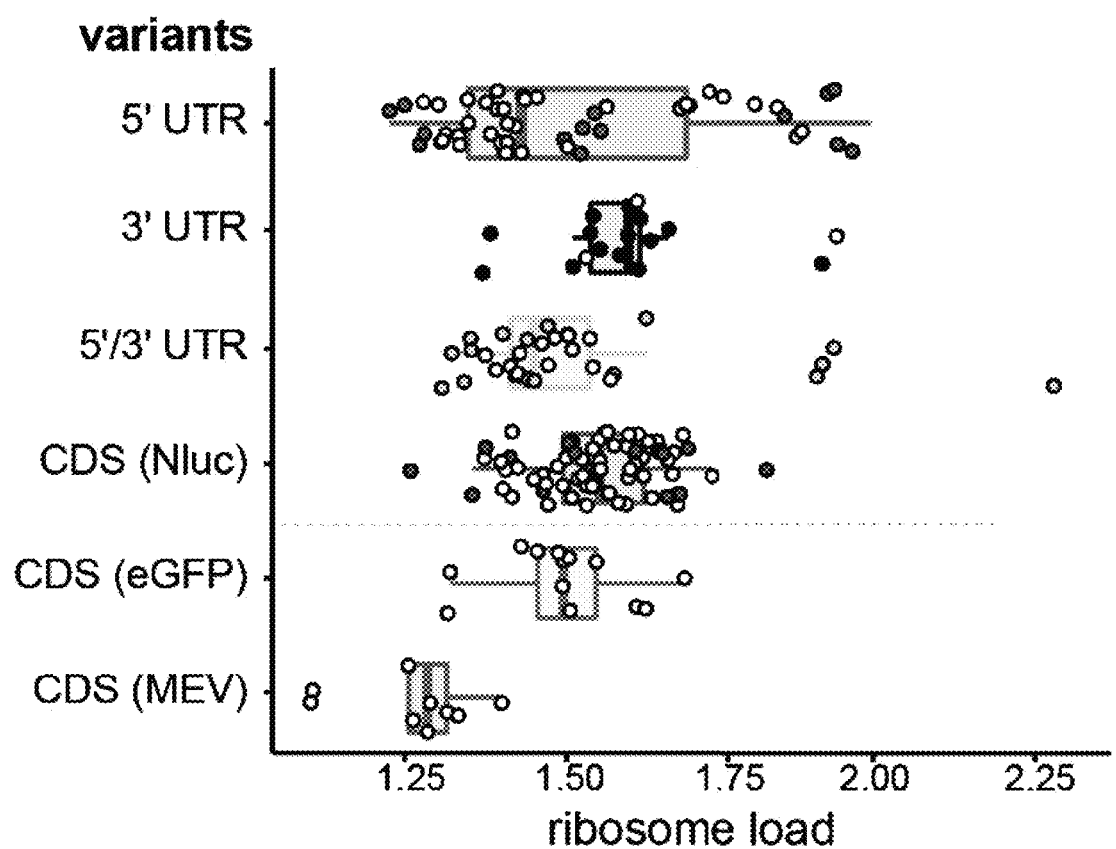
FIGS. 7A-7C illustrate exemplary data in the form of box and whisker plots showing ribosome load (FIG. 7A), in cell half-life (FIG. 7B), and in solution half-life (FIG. 7C).
Figure 7B:
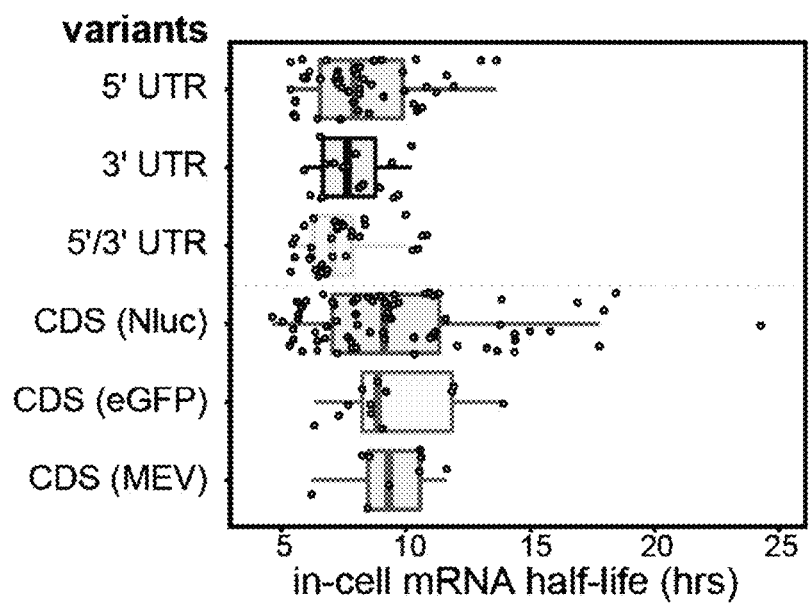
Figure 7C:
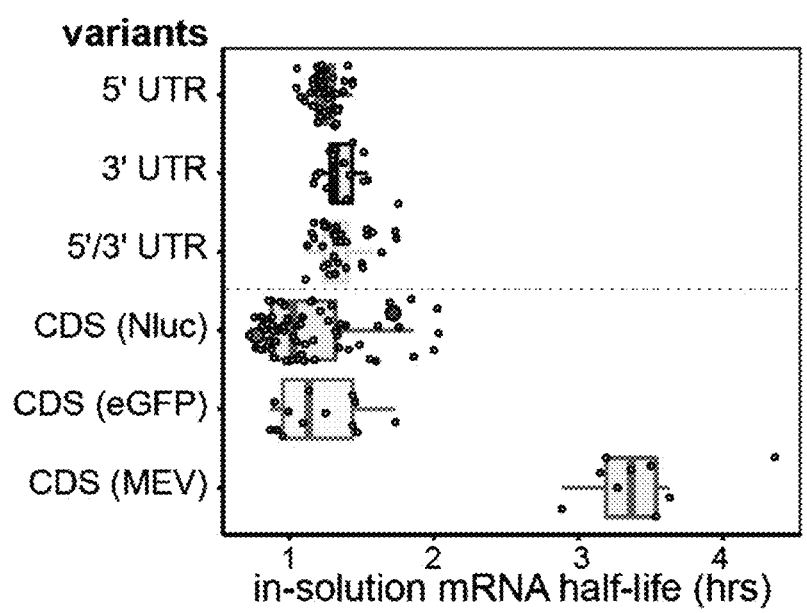

Additionally, FIGS. 7A-7C illustrate exemplary data plotting ribosomal load (FIG. 7A), half-lives for in-cell (or in vivo) stability (FIG. 7B) and in solution (or in vitro) stability (FIG. 7C) of various mRNA molecules, including mRNA molecules having 5'UTR variants, 3'UTR variants, both 5'UTR and 3'UTR variants, and various CDS sequences, including from Nluc, eGFP, and MEV. For ribosomal load in FIG. 7A, ribosomal load is determined by the equation listed in FIG. 7A.

FIGS. 8A-8C illustrate exemplary data showing correlations of in cell mRNA half-life to ribosomal load (FIG. 8A), in cell mRNA half-life to monosome-to-free-subunit ratio (FIG. 8B), and in cell mRNA half-life to polysome-to-monosome ratio (FIG. 8C).

Given the assessment of in cell stability and translatability in accordance with various embodiments, further embodiments determine protein expression levels of proteins encoded in a CDS of the molecule. Certain embodiments determine protein expression via the equation:

$$P(t) \sim k_t \frac{e^{-k_p t} - e^{-k_m t}}{k_m - k_p}$$

Where P(t) is protein quantity at time t; $k_t$ is translation rate; and $k_m$ and $k_p$ are rates of mRNA and protein decay, respectively.

An exemplary demonstration of predicted expression is illustrated in FIGS. 9A-9C, where FIG. 9A illustrates in cell half-life of various mRNA constructs, FIG. 9B illustrates ribosomal load of various constructs, and FIG. 9C illustrates the predicted expression.

EXEMPLARY EMBODIMENTS

Although the following embodiments provide details on certain embodiments of the inventions, it should be understood that these are only exemplary in nature, and are not intended to limit the scope of the invention.

Example 1: In Vitro Transcription of Reporter mRNAs

Method:

Preparation of mRNAs were based on in vitro transcription from DNA templates. DNA templates were amplified by PCR using AccuPrime Pfx (Life Technologies, 12344024) and purified using the Monarch PCR & DNA Cleanup Kit (NEB, T1030L). The source of the 3×HA-Nluc starting CDS ("Nluc start") is derived from the pcDNA3.1-5'UTR-3×HA-Nluc plasm id encoding the HA-tagged Nanoluc CDS. Individual template DNA or the 233-mRNA library was amplified from linear DNA synthesized on a BioXP 3200 system (Codex DNA) or by Twist Bioscience, using the fixed forward (T7_F_28 nt) and reverse (const3_R) primer. The forward primer binds to the T7 RNA polymerase promoter common in DNA template for all mRNA designs; the reverse primer is complementary to a common "const3" region at the end of all tested mRNA 3' UTRs. For the IVT template pool, individual DNA templates were pooled for a template pool of hundreds of constructs at an equimolar concentration and are amplified with outer primers in a pooled format. For the pooled template, 1 μL of each construct (~20 ng/μL stock concentration) was pooled to be used as the PCR template. The Pfx PCR contained the following: 2.5 μL 10×Pfx buffer, 0.25 μL forward primer (100 uM), 0.25 μL reverse primer (100 uM), 0.75 μL DMSO (NEB), 0.25 μL Pfx Polymerase (Thermo), 20.5 water, and 0.5 μL template DNA (~20-50 ng/ul), in a total 25 μL reaction with the following program: 2 min at 95° C.; 10 sec at 95° C.; 30 sec at 58° C.; 30 s or 1 min at 68° C.; cycled 9×; final extension of 5 min at 68° C. PCR reactions were purified with Monarch PCR & DNA Cleanup Kit (NEB, T1030L). For the hHBB-Fluc control mRNA, the DNA template was amplified from the pGL3-HBB plasmid using the primers KL588/KL589 which yielded a PCR product of 1,750 kb in length. For cloning the MALAT1 ENE 3' UTR stem-loop, we first amplified the ENE region using primers ENE-1/ENE-2 with flanking constant regions. The resulting amplicon was assembled with a hHBB-Nluc sequence that lacked a 3' UTR but maintained a unique barcode using a NEBuilder HiFi Assembly Kit (NEB, ES2621).

In vitro transcription was performed with the MEGAscript T7 kit (Ambion, AM1333) according to the manufacturer's instructions. A 20 μL transcription reaction contained max. 5 μg linear DNA template, 4 mM of each NTP (Ambion), 2 μL/200 U MEGAscript T7 RNA polymerase (Ambion) and 1×T7 MEGAscript Transcription Buffer (Ambion). After a total incubation for 3 hours at 37° C., the DNA was digested by addition of 1 μL/2 U Turbo DNase (Ambion, AM2238) for 15 min at 37° C. For pseudouridylated mRNAs, pseudouridine triphosphate (Trilink Biotechnologies, N1019-5) was substituted for uridine triphosphate at an equivalent concentration. mRNA was purified using MegaClear columns (Thermo Scientific, Ambion, AM1908). A 20 μL reaction usually yielded 100-150 μg of RNA.

For mRNA transfection of HEK293T cells, m$^7$G-capped and polyadenylated mRNAs were generated as follows. In vitro transcribed mRNA was then m$^7$G-capped and polyadenylated using the ScriptCap m7G Capping System (CellScript, C-SCCE0625) and A-Plus Poly(A) Polymerase Tailing Kit (CellScript, C-PAP5104H), respectively, according to the manufacturer's instruction with the following modifications. Aliquots of 30 μg of each RNA were processed in parallel, diluted to 34.25 μL in water and heated for 5 min at 65° C. to denature and placed on ice. The 50 μL capping reaction contained 5 μL 10× ScriptCap buffer (Cellscript), 5 μL 10 mM GTP (Cellscript), 2.5 μL 2 mM S-adenosyl-methionine (SAM, 20 mM stock, Cellscript), 1.25 μL ScriptGuard RNase Inhibitor (Cellscript), and 2 μL Capping enzyme (20 U, Cellscript, 10 U/μL). For the capping step, the 37° C. incubation was performed for 1 hour and the capped RNA was placed on ice. Polyadenylation was performed from the resulting RNAs without purification in between. The polyA reaction contained 30 µg of capped mRNA in 50 µL, 6.6 µL 10×A-Plus polyA tailing buffer (Cellscript), 6.6 µL 10 mM ATP (Cellscript), 0.3 µL Script-Guard RNase Inhibitor (Cellscript), and 2.5 µL A-Plus PolyA Polymerase (10 U, 4 U/µL, Cellscript) in a total reaction volume of 66 µL. We aimed to add a 150 nt-long polyA-tail for which we incubated the capped mRNA for 30 min at 37° C. with 10 U of polyA enzyme, after which the reaction was placed on ice. The mRNA was again purified using MegaClear columns. mRNA concentration was determined on a Nanodrop 2000 (Thermo Fisher). This usually yields 30-40 µg of capped and polyadenylated mRNA. mRNA quality was determined by 4% urea-PAGE, 1% formaldehyde agarose gel or capillary electrophoresis with an Agilent 2100 Bioanalyzer (Agilent Technologies).

Example 2: Cell Culture and Transfections

Method:

HEK293T (ATCC: CRL-3216) cells were cultured in Dulbecco's Modified Eagle's Medium (DMEM, Gibco, 11965-118) containing 2 mM L-glutamine, supplemented with 10% fetal bovine serum (EMD Millipore, TMS-013-B), 100 U/ml penicillin and 0.1 mg/ml streptomycin (Embryo-Max ES Cell Qualified Penicillin-Streptomycin Solution 100×; EMD Millipore, TMS-AB2-C or Gibco, 15140-122) at 37° C. in 5% $CO_2$-buffered incubators. For transfection of pooled 5' $m^7G$-capped and poly(A)-tailed RNAs, $5.0 \times 10^6$ HEK293T cells were seeded in a 10 cm plate 24 h before transfection. 10 µg of pooled RNAs were transfected using Lipofectamine MessengerMax as per manufacturer's instructions (Life Technologies). Media was changed 3 h after transfection and replaced with complete DMEM supplemented with 10% FBS and Pen/Strep. For transfections of individual $m^7G$-capped RNAs, $3.0 \times 10^4$ HEK293T cells were seeded per well 24 h before transfection in a 96-well plate. Subsequently, 10 ng of Nluc RNA was co-transfected with 20 ng of $m^7G$-capped HBB-Fluc control RNA using Lipofectamine MessengerMax as per manufacturer's instructions (Life Technologies).

Example 3: Sucrose Gradient Fractionation Analysis

Method:

Cell culture media was replaced with cycloheximide (MilliporeSigma, C7698-1G) containing media at 100 ug/mL. After 2 minutes, cells were washed, trypsinized and harvested using PBS, trypsin, and culture media containing 100 g/mL cycloheximide. ~$10 \times 10^6$ cells were resuspended in 400 µL of following lysis buffer on ice for 30 min, vortexing every 10 min: 25 mM Tris-HCl pH 7.5, 150 mM NaCl, 15 mM $MgCl_2$, 1 mM DTT, 8% glycerol, 1% Triton X-100, 100 µg/mL cycloheximide, 0.2 U/µL Superase-In RNase inhibitor (ThermoFisher Scientific, AM2694), 1× Halt protease inhibitor cocktail (ThermoFisher Scientific, 78430), 0.02 U/µL TURBO DNase (ThermoFisher Scientific, AM2238). After lysis, nuclei were removed by two step centrifuging, first at 1300 g for 5 min and second at 10000 g for 5 min, taking the supernatants from each. 25%-50% sucrose gradient was prepared in 13.2 mL ultracentrifuge tubes (Beckman Coulter, 331372) using Biocomp Gradient Master with the following recipe: 25 or 50% sucrose (w/v), 25 mM Tris-HCl pH 7.5, 150 mM NaCl, 15 mM $MgCl_2$, 1 mM DTT, 100 µg/mL cycloheximide. The lysate was layered onto the sucrose gradient and ultracentrifuged on Beckman Coulter SW-41Ti rotor at 40000 rpm for 150 min at 4° C. The gradient was density fractionated using Brandel BR-188 into 16×750 µL fractions, and in vitro transcribed spike-in RNA mix (12000261, 120010E31, 220023B1, 310333T3; 1000, 100, 10, 1-fold dilutions respectively) were added to each fraction. 700 µL of each fraction was mixed with 100 µL 10% SDS, 200 µL 1.5 M sodium acetate, and 900 µL acid phenol-chloroform, pH 4.5 (ThermoFisher Scientific, AM9720), heated at 65° C. for 5 min, and centrifuged at 20.000 g for 15 min at 4° C. for phase separation. 600 µL aqueous phase was mixed with 600 µL 100% ethanol and RNA was purified on silica columns (Zymo, R1013).

Example 4: Polysome Selection and Library Preparation

Method:

The variant 5' UTR is composed of: fixed first 29 nt of hHBB, variable 35 nt (initially degenerate) and 6 nt Kozak consensus. To generate the reporter mRNA pool containing the variant 5' UTR library, IVT template was first assembled by PCR under the following conditions: 4 µL 10× AccuPrime Pfx Reaction Mix, 0.4 pmol HBB29_N35 amplicon, 0.4 pmol Nluc_HBB_3 UTR, 0.4 µL AccuPrime Pfx Polymerase in 40 µL of total reaction volume. Cycling conditions are: 95° C. for 120 sec, and 19 cycles of 95° C. for 15 sec, 66° C. for 30 sec, 68° C. for 75 sec. PCR product was purified on silica columns (NEB T1034) and amplified with under the following conditions: 4 uL 10× AccuPrime Pfx Reaction Mix, 4 µL 10 µM T7_28_HBB_30_F, 4 µL 10 µM Nanoluc_ORF_R, 0.4 µL AccuPrime Pfx Polymerase in 40 µL total reaction volume. Cycling conditions are: 95° C. for 120 sec, and 4 cycles of 95° C. for 15 sec, 66° C. for 30 sec, 68° C. for 75 sec. The mRNA was in vitro transcribed, capped and polyadenylated as described above. This yields an estimated initial starting degenerate pool complexity of $\sim 2.4 \times 10^{11}$.

Transfection of HEK-293 cells and sucrose gradient fractionation were performed as described above. Equal volumes of fractions 10-16 were pooled and RNA was by acidic phenol chloroform extraction followed by column purification (Zymo Research, R1013) as described above. ⅓ lysate volume was kept as input before layering onto the sucrose gradient and RNA was extracted from the input lysate by Trizol extraction followed by column purification. 1.5 µg RNA in 5.5 µL was mixed with 0.5 µL 2 uM RT_Nluc26_UMI12_Read1Partial and 0.5 µL 10 mM dNTPs each. The RNA samples were then denatured at 65° C. for 5 min and chilled to 4° C. 3.5 µL reverse transcription mix was added to 10 µL total reaction volume: 2 µL 5× Superscript IV buffer, 0.5 µL 10 mM DTT, 0.5 µL Superase-In (ThermoFisher Scientific, AM2694), 0.5 µL Superscript IV (Thermo 18091050). The reaction was incubated at 55° C. for 45 min and inactivated at 80° C. for 10 min. Variant 5' UTR amplicon was amplified from the reverse transcription reaction via PCR under the following reaction conditions: 4 µL RT reaction, 40 µL 2×Q5 Hot Start Master Mix (NEB M0494S), 0.8 µL 100×SYBR (Thermo S7563), 4 µL 10 µM T7_28_HBB_29_F, 4 µL 10 µM Nanoluc_ORF_R, in 80 µL total reaction volume. Cycling conditions were as follows: 98° C. for 60 sec, and 15 cycles of 98° C. for 10 sec, 68° C. for 10 sec, 72° C. for 10 sec. PCR product was purified on silica columns (NEB T1034) and assembly with Nluc_HBB_3 UTR fragment was performed as described above for initial preparation of IVT template using HBB29_N35 amplicon. The mRNA was in vitro transcribed, capped and polyadenylated as described above. The same process of transfection, fractionation, reverse transcription, PCR amplification, assembly and in vitro transcription was repeated.

For sequencing library preparation, the RT reaction was PCR amplified under the following conditions: 1 μL RT reaction, 10 μL 2×Q5 Hot Start Master Mix (NEB M0494S), 0.2 μL 100×SYBR (Thermo S7563), 1 μL 10 μM Read1, 1 μL 10 μM Read2Partial_HBB29 in 20 μL total reaction volume. Cycling conditions were as follows: 98° C. for 60 sec, and 15 cycles of 98° C. for 10 sec, 68° C. for 10 sec, 72° C. for 10 sec. Sequencing adaptors were added using the following conditions for final round PCR: 1 μL first round PCR reaction, 10 μL 2×Q5 Hot Start Master Mix, 0.2 μL 100×SYBR, 1 μL 10 uM NEBNext Index Primer (NEB E7335, NEB E7500, NEB E7710, NEB E7730, NEB E6609), 1 μL 10 uM NEBNext Universal PCR Primer in 20 μL total volume. Cycling conditions are: 98° C. for 60 sec, and 5 cycles of 98° C. for 10 sec, 72° C. for 10 sec. All barcoded samples were then pooled at equal volumes and purified with 1.1× SPRIselect beads Beckman Coulter B23317). Sequencing was performed at the Stanford Functional Genomics Facility (SFGF) at Stanford University, on the Illumina NextSeq 550 instrument, using a high output kit, 1×81 cycles.

Example 5: In Cell and In-Solution RNA Degradation Time Courses

Method:

For in-cell RNA stability, the 233-member in vitro transcribed mRNA pool ($m^7G$-capped and polyA) was transfected into HEK293T cells as described above and RNA was harvested at 1, 7, 12, and 24 h in Trizol (ThermoFisher Scientific, 15596026). RNA was extracted from the aqueous phase on silica columns (Zymo, R1013).

For in-solution RNA degradation experiments, 750 ng of the 233-mRNA pool (not $m^7G$-capped or polyA) was incubated in 30 μL of Degradation Buffer (50 mM CHES at pH 10 and 10 mM $MgCl_2$) and collected over 10 time points: 0, 0.5, 1, 2, 3, 4, 5, 6, 16 and 24 h. To each sample, 15 μL of 0.5 M Tris-HCl pH 7 and 3 μL of 0.5 M EDTA-Na was added to quench the degradation. The integrity of each sample was checked by loading 5 μL of total RNA alongside a spike-in control (P4P62HP, 50 ng) onto a PAGE-Urea-TBE gel and visualized by SYBR Gold (Thermo Fisher). Subsequently, RNA was purified using Ampure beads+40% polyethylene glycol 8000 (7:3) and checked again by PAGE-Urea-TBE gel and visualized by SYBR Gold.

Example 6: Measurement of In-Solution mRNA Stability by Capillary Electrophoresis Method:

For one-by-one measurement of in-solution mRNA stability, in vitro transcribed mRNA was incubated in a degradation buffer over ten time points (0, 0.5, 1.0, 1.5, 2, 3, 4, 5, 18, and 24 hours), then analyzed by capillary electrophoresis.

For each time point, 1.6 pmol of mRNA brought to 10 μL in a buffer containing 50 mM Na-CHES at pH 10 with 10 mM $MgCl_2$, and the reaction was incubated at 25° C. When the incubation period was reached for each time point, 5 μL of Tris-HCl at pH 7 and 1 μL of 500 mM EDTA in nuclease free water was added to quench the degradation reaction, and frozen for further analysis. After the final time point (24 hours), 4 μL of each mRNA degradation sample (out of a total stored volume of 16 μL) was taken, and mixed with 1 μL of a control RNA at a concentration of 50 ng/μL. For these experiments we opted to use the P4-P6 domain of the Tetrahymena ribozyme with two added hairpins (~239 nt) as a control. The RNA mixture was then purified using a mixture of AMPure XP beads (Beckman Coulter) with 40% polyethylene glycol (mixed in a 7:3 ratio). The resulting RNA was eluted into 4.5 μL of RNAse-free water for analysis on the 2100 Bioanalyzer (Agilent) using the RNA-Nano Eukaryote protocol.

The data from the Bioanalyzer were analyzed using a custom script that performs the following analysis. We first converted elution times to nucleotides based on a ladder control (25, 200, 500, 1000, 2000, and 4000 nts). Relative mRNA amounts were estimated based on peak areas at expected band lengths (for example, ~900 nucleotides for the mRNAs of interest and ~265 nucleotides for the control). When calculating peak areas, background subtraction was performed, where the background was defined as the area under a linear line in the range of nucleotides used for the peak area. Normalization was performed using two different methods used to cross-validate. First, the peak areas of full-length mRNA were normalized to the control P4-P6 domain RNA that was spiked into the samples after degradation was performed. Second, peak areas of full-length mRNAs were also normalized to the total amount of RNA in the lane less the peak area of the bands of interest (between ~20-1000 nucleotides in our case), assuming that the majority of the other RNA in the lane were degradation products from the mRNA of interest. These distinct approaches to normalizing the data gave the same results within estimated error (see below). After calculations of normalized peak areas, fraction intact values were then calculated for each mRNA by dividing the normalized area across the ten timepoints by the normalized area at the start (0 hours).

$$\text{Fraction Intact}_i = \frac{\text{Normalized Area}_i}{\text{Normalized Area}_{0 hours}}$$

For each sample, fraction intact values were fit across the different timepoints to an exponential function:

$$F_i = Ae^{-t/\tau}$$

Where $F_i$ is an array of fraction intact values across multiple time points, A is the amplitude of the exponential decay function, τ is the time constant, and t is an array of time points in hours. The time constant was then used to calculate the in vitro half-life of mRNA:

$$\text{Half-life} = \ln(2)\tau$$

Example 7: Library Preparation and Amplicon Sequencing

Method:

Up to 250 ng RNA in 2.75 μL was mixed with 0.25 μL 2 μM RT_Const2_N12_Read1Partial and 0.25 μL 10 mM dNTPs each. The RNA samples were then denatured at 65° C. for 5 min and chilled to 4° C. 1.75 μL reverse transcription mix was added to 5 μL total reaction volume: 1 μL 5× Superscript IV buffer, 0.25 μL 10 mM DTT, 0.25 μL Superase-In (ThermoFisher Scientific, AM2694), 0.25 μL Superscript IV (Thermo 18091050). The reaction was incubated at 55° C. for 45 min and inactivated at 80° C. for 10 min.

First round PCR was performed under following conditions: 1 µL RT reaction, 10 µL 2×Q5 Hot Start Master Mix (NEB M0494S), 0.2 µL 100×SYBR (Thermo S7563), 1 µL 10 uM Read1Partial_F, 1 µL 10 uM 50:50 Hbb_Fwd: Nluc_Fwd mix in 20 µL total volume. Cycling conditions were: 98° C. for 60 sec, and 15 cycles of 98° C. for 10 sec, 68° C. for 10 sec and 72° C. Second round PCR was performed under the following conditions: 1 µL first round PCR, 10 µL 2×Q5 Hot Start Master Mix, 0.2 µL 100×SYBR, 1 µL 10 uM Read1Partial_F, 1 µL 10 uM Read2Partial_Const1_R in 20 µL total volume. Cycling conditions were: 98° C. for 60 sec, and 5 cycles of 98° C. for 10 sec, 72° C. for 5 sec. Sequencing adaptors were added using the following conditions for final round PCR: 1 µL second round PCR, 10 µL 2×Q5 Hot Start Master Mix, 0.2 µL 100×SYBR, 1 µL 10 µM NEBNext Index Primer (NEB E7335, NEB E7500, NEB E7710, NEB E7730, NEB E6609), 1 µL 10 µM NEBNext Universal PCR Primer in 20 µL total volume. Cycling conditions were: 98° C. for 60 sec, and 5 cycles of 98° C. for 10 sec, 72° C. for 5 sec. All barcoded samples were then pooled at equal volumes and purified with 1.1× SPRIselect beads (Beckman Coulter B23317). Sequencing was performed at the Stanford Functional Genomics Facility (SFGF) at Stanford University, on an Illumina NextSeq 550 instrument, using a high output kit, 1×76 cycles. The SEQ ID NOs for the various PCR primers are listed in Table 4.

TABLE 4

Primer Sequences

| Name: | SEQ ID NO: |
|---|---|
| RT_Const2_N12_Read1Partial | 1384 |
| Const3_R | 1385 |
| Hbb_Fwd | 1386 |
| Nluc_Fwd | 1387 |
| Read1Partial_F | 1388 |
| Read2Partial_Const1_R | 1389 |
| T7_F_28nt (forward) | 1390 |

Example 8: Amplicon Sequencing Data Analysis

Method:

After bcl conversion and demultiplexing with Illumina bcl2fastq, the constant regions were trimmed using cutadapt. The trimmed reads were aligned to the indexed reference of barcode sequences using Bowtie2 with the following options: -L 11 -N 0 --nofw. The alignments were deduplicated based on UMIs using UMIcollapse with -p 0.05 and counted using samtools idxstats. This pipeline yields a matrix of barcode read counts where rows are the different constructs in the library and columns are the different samples.

The count matrix was log transformed and normalized column-wise using a linear fit on the dilution series of spike-in constructs in each sample. For the calculation of RNA degradation coefficients in cells, we carried out a linear fit to log RNA abundance from the time course data, i.e. we fit an expression of $Y=\beta_0+\beta_1 t$ where Y is the normalized log RNA abundance and t is the number of hours after transfection; $\beta_1$ is the degradation constant. For the calculation of in solution degradation coefficients, sufficient data points were available to carry out a nonlinear fit directly to an exponential model, i.e. an expression of $y=A \exp(-\tau/t)$ was fit, where y is the fraction intact (RNA abundance normalized to initial abundance), A is the amplitude, t is the time of incubation in degradation buffer in hours, and τ is the degradation time constant. Time courses in which the observed fraction intact exceeded the fitted exponential by more than 0.05 in the last time point signaled RT-PCR amplification of mispriming, non-full-length products and were filtered out of downstream analysis.

For polysome profiles, percent RNA abundances for each fraction were first calculated by scaling per-fraction values by the sum of all fractions. For the heatmap displays in the figures, column medians were also subtracted from each percent RNA value. For the calculation of ribosome load, the matrix of percent RNA abundances in fractions 4-9 (1-3 are free RNP fractions, and >9 have negligible abundance) were first multiplied by a weight vector representing the number of ribosomes in each fraction as determined by the A260 trace from the fractionator, then the weighted abundances were summed across the row. For the calculation of polysome to monosome ratio, the sum of fractions 7-9 (>3 ribosomes) abundances were divided by fraction 4 (80S) abundance. For the calculation of monosome to 40S/60S ratio, fraction 4 (80S) abundance was divided by the sum of fraction 2 (40S/60S) abundance.

To calculate the expected protein levels assuming first order kinetics of mRNA translation and mRNA/protein decay, the following differential equations were used:

$$\frac{dM}{dt} = -k_m \cdot M(t)$$

$$\frac{dP}{dt} = k_t \cdot M(t) - k_p \cdot P(t)$$

where dM/dt and dP/dt are rates of change in mRNA and protein levels, respectively; M(t) and P(t) are moles of mRNA and protein at time t, respectively; $k_t$ is the translation rate constant; and $k_m$ and $k_p$ are rate constants of mRNA and protein decay, respectively. The analytical solution for P(t) is proportional to:

$$P(t) \sim k_t \frac{e^{-k_p t} - e^{-k_m t}}{k_m - k_p}$$

where $m_0$ is the mass of mRNA present at t=0, and l is the mRNA length in nucleotides. $k_p$ is set to 0 since Nluc protein has negligible degradation as measured by luciferase activity in transiently Nluc-expressing HEK293 cells for at least 6 hours after cycloheximide treatment, which allows assessment of protein degradation in the absence of further translation[99]. $k_m$ is the degradation constant obtained from the linear fit of in-cell time course RNA data ($-\beta_1$ above). $k_t$ is the ribosome load calculated by summing weighted RNA abundances from polysome profile data Example 9: Luciferase Activity Assay after mRNA Transfection Method:

Media from transiently transfected HEK293T cells was aspirated and cells were lysed in 40 µL of 1× passive lysis buffer from the Dual-Luciferase Reporter Assay System (Promega, E1980) and either directly assayed or frozen at −20° C. After thawing, 20 µL of supernatant was transferred to a new plate and assayed for luciferase activity using the Nano-Glo Dual-Luciferase Reporter Assay System (Promega, N1610) to measure Firefly (Fluc) and NanoLuc (Nluc) luciferase activities. In particular, 50 µL of ONE-Glo Ex Reagent was added to each well of lysate and incubated for 3 minutes at room temperature before measuring Fluc activities. Subsequently, 50 µL of NanoDLR Stop & Glo reagent was added to each well, and incubated for 10 min at room temperature before measuring luciferase activities on a GloMax-Multi (Promega) plate reader. Luciferase reporter activity is expressed as a ratio between Nluc and Fluc. Each experiment was performed a minimum of three independent times. Because this assay relies on accumulation of luciferase in the cytosol, any signal peptide sequences were removed from the CDS for templates and mRNA for these transfection and luciferase activity experiments.

Example 10: Polysome Selection Library Sequencing Data Analysis

Method:

Following adapter trimming, 670440 sequences with at least 10 summed read count across all libraries combined were set as the reference. Each library was aligned to this indexed reference using Bowtie2. Only uniquely mapping reads with edit distance ≤3 were retained. Alignments were further deduplicated using UMIcollapse (-p 0.05, -k 1). This results in the matrix of read count where rows are different sequence variants and columns are the samples.

Normalized counts were obtained by dividing the matrix column-wise by total read counts per sample. For sequence variants with at least 15 reads in any one of the samples, a regression model was fitted on normalized read counts with the sequential selection rounds as ordinal predictors, penalizing differences between coefficients of adjacent groups (R package ordPens). False discovery rate was estimated by Benjamini-Hochberg procedure. For choosing the final set of candidates, the criteria of read counts in the final round polysome selection library and fold enrichment over input in the final round was also required.

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole, and that variations in the components or steps of the present invention may be made within the spirit and scope of the invention. Accordingly, the present invention is not limited to the specific embodiments described herein, but, rather, is defined by the scope of the appended claims.

The invention claimed is:

1. A method to determine RNA translatability, comprising:

obtaining a pool of RNA molecules, wherein each RNA molecule is uniquely encoded with a barcoding sequence and each barcoding sequence is flanked by at least one profiling sequence;

transfecting a cell or cell lysate with the pool of RNA molecules;

performing polysome profiling on the pool of RNA molecules to segregate RNA molecules based on the number of ribosomes bound to the RNA molecule;

isolating a first fraction from the polysome profile to generate a first set of RNA molecules showing a first level of entire ribosomes bound to the RNA molecules in the set of RNA molecules;

isolating a second fraction from the polysome profile to generate a second set of RNA molecules showing a second level of entire ribosomes bound to the RNA molecules in the set of RNA molecules, wherein the first level and second level represent different amounts of bound ribosomes;

sequencing the barcode sequence of each RNA molecule in the first set of RNA molecules and the second set of RNA molecules to identify the presence of each RNA molecule in the first fraction of RNA molecules and the second fraction of RNA molecules;

sequencing the barcode sequence of each RNA molecule in the first set of RNA molecules and the second set of RNA molecules to identify the presence of each RNA molecule in the each set of RNA molecules; and determining, quantitatively, translatability of the RNA molecules associated with each barcode sequence in the first fraction and the second fraction by identifying the prevalence of each barcode in each fraction.

2. The method of claim 1, wherein the RNA molecules are transfected into a collection of cells or a cell lysate, wherein the collection of cells is selected from mammalian cells, yeast cells, bacteria cells, and plant cells.

3. The method of claim 1, wherein polysome profiling comprises adding a cell lysate to a sucrose gradient and centrifuging the sucrose gradient to segregate the RNA molecules.

4. The method of claim 1, wherein the barcoding sequence is selected from SEQ ID NOs: 115-1380 and the profiling sequence is selected from SEQ ID NOs: 1381-1382.

5. The method of claim 1, further comprising
generating a distribution for each RNA molecule based on the prevalence of each RNA molecule in each fraction.

6. The method of claim 1, wherein isolating a first fraction further comprises introducing a known amount of spike-in RNA molecule, wherein the spike-in RNA molecule serves as an internal reference to allow for quantification of the first set of RNA molecules.

* * * * *

SEQUENCE LISTING

```
<160> NUMBER OF SEQ ID NOS: 1390

<210> SEQ ID NO 1
<211> LENGTH: 28
<212> TYPE: DNA
<213> ORGANISM: Artificial Sequence
<220> FEATURE:
<223> OTHER INFORMATION: Modified 5'UTR

<400> SEQUENCE: 1
acacgctgga attctagtat actaaacc                                            28

<210> SEQ ID NO 2
<211> LENGTH: 29
<212> TYPE: DNA
<213> ORGANISM: Artificial Sequence
<220> FEATURE:
<223> OTHER INFORMATION: Modified 5'UTR

<400> SEQUENCE: 2
acatttgctt ctgacacaac tgtgttcac                                           29

<210> SEQ ID NO 3
<211> LENGTH: 33
<212> TYPE: DNA
<213> ORGANISM: Artificial Sequence
<220> FEATURE:
<223> OTHER INFORMATION: Modified 5'UTR

<400> SEQUENCE: 3
ctcccgggct ggcagcaggg ccccagcggc acc                                      33

<210> SEQ ID NO 4
```

```
<211> LENGTH: 36
<212> TYPE: DNA
<213> ORGANISM: Artificial Sequence
<220> FEATURE:
<223> OTHER INFORMATION: Modified 5'UTR

<400> SEQUENCE: 4
cgcgcctagc agtgtcccag ccgggttcgt gtcgcc                              36

<210> SEQ ID NO 5
<211> LENGTH: 39
<212> TYPE: DNA
<213> ORGANISM: Mus musculus

<400> SEQUENCE: 5
cttccttttg tgactggcgg tgaacgagtg cgcagtgcc                           39

<210> SEQ ID NO 6
<211> LENGTH: 41
<212> TYPE: DNA
<213> ORGANISM: Homo sapiens

<400> SEQUENCE: 6
agcgaggctg ctgtggtcta cacgactctc tgagcttcgc c                        41

<210> SEQ ID NO 7
<211> LENGTH: 46
<212> TYPE: DNA
<213> ORGANISM: Artificial Sequence
<220> FEATURE:
<223> OTHER INFORMATION: Modified 5'UTR

<400> SEQUENCE: 7
agacccaagc tagctagcgt ttaaacttaa gctaggtacc gagacc                   46

<210> SEQ ID NO 8
<211> LENGTH: 47
<212> TYPE: DNA
<213> ORGANISM: Tobacco etch virus

<400> SEQUENCE: 8
gggaaataag agagaaaaga agagtaagaa gaaatataag agccacc                  47

<210> SEQ ID NO 9
<211> LENGTH: 50
<212> TYPE: DNA
<213> ORGANISM: Artificial Sequence
<220> FEATURE:
<223> OTHER INFORMATION: Modified 5'UTR

<400> SEQUENCE: 9
acatttgctt ctgacacaac tgtgttcact agcaacctca aacagacacc               50

<210> SEQ ID NO 10
<211> LENGTH: 58
<212> TYPE: DNA
<213> ORGANISM: Artificial Sequence
<220> FEATURE:
<223> OTHER INFORMATION: Modified 5'UTR

<400> SEQUENCE: 10
aggcacagac accaaggaca gagacgctgg ctaggccgcc ctccccactg ttaccaac      58

<210> SEQ ID NO 11
<211> LENGTH: 61
```

<212> TYPE: DNA
<213> ORGANISM: Artificial Sequence
<220> FEATURE:
<223> OTHER INFORMATION: Modified 5'UTR

<400> SEQUENCE: 11 cttcctttg tacatttgct tctgacacaa ctgtgttcac tagcaacctc aaacagacac    60
c                                                                   61

<210> SEQ ID NO 12
<211> LENGTH: 61
<212> TYPE: DNA
<213> ORGANISM: Artificial Sequence
<220> FEATURE:
<223> OTHER INFORMATION: Modified 5'UTR

<400> SEQUENCE: 12
actcctcccc atcctctccc tctgtccctc tgtccctctg accctgcact gtcccagcac    60
c                                                                   61

<210> SEQ ID NO 13
<211> LENGTH: 62
<212> TYPE: DNA
<213> ORGANISM: Artificial Sequence
<220> FEATURE:
<223> OTHER INFORMATION: Modified 5'UTR

<400> SEQUENCE: 13
acatttgctt ctgacacaac tgtgttcact agcaacctca aacagacacc aaaaaaaaaa    60
aa                                                                  62

<210> SEQ ID NO 14
<211> LENGTH: 63
<212> TYPE: DNA
<213> ORGANISM: Artificial Sequence
<220> FEATURE:
<223> OTHER INFORMATION: Modified 5'UTR

<400> SEQUENCE: 14
ggtaatctgc aaatccctgg cacccgccta aaattgccct catcaacctt ctctctattc    60
acg                                                                 63

<210> SEQ ID NO 15
<211> LENGTH: 65
<212> TYPE: DNA
<213> ORGANISM: Artificial Sequence
<220> FEATURE:
<223> OTHER INFORMATION: Modified 5'UTR

<400> SEQUENCE: 15
ggctctgaaa aaaaaaaaaa gacccaagct agctagcgtt taaacttaag ctaggtaccg    60
agacc                                                               65

<210> SEQ ID NO 16
<211> LENGTH: 68
<212> TYPE: DNA
<213> ORGANISM: Tobacco mosaic virus

<400> SEQUENCE: 16 gtattttac aacaattacc aacaacaaca acaacaaac aacattacaa ttactattta    60
caattaca                                                            68

<210> SEQ ID NO 17
<211> LENGTH: 72
<212> TYPE: DNA
<213> ORGANISM: Artificial Sequence
<220> FEATURE:
<223> OTHER INFORMATION: Modified 5'UTR

<400> SEQUENCE: 17

```
ggctctgaaa aaaaaaaaac cgacatttgc ttctgacaca actgtgttca ctagcaacct    60
caaacagaca cc                                                        72
```

<210> SEQ ID NO 18
<211> LENGTH: 78
<212> TYPE: DNA
<213> ORGANISM: Homo sapiens

<400> SEQUENCE: 18

```
cttccccgt tctcttcggt tctcatcgct gtgagtgtgc tgggcaggtg cggacgccag      60
agccgagccc gcgtcgcc                                                  78
```

<210> SEQ ID NO 19
<211> LENGTH: 83
<212> TYPE: DNA
<213> ORGANISM: Artificial Sequence
<220> FEATURE:
<223> OTHER INFORMATION: Modified 5'UTR

<400> SEQUENCE: 19

```
attaaaggtt tataccttcc caggtaacaa accaaccaac tttcgatctc ttgtagatct    60
gttctctaaa cgaactttaa aat                                            83
```

<210> SEQ ID NO 20
<211> LENGTH: 84
<212> TYPE: DNA
<213> ORGANISM: Homo sapiens

<400> SEQUENCE: 20

```
accgccgaga ccgcgtccgc cccgcgagca cagagcctcg cctttgccga tccgccgccc    60
gtccacaccc gccgccagct cacc                                           84
```

<210> SEQ ID NO 21
<211> LENGTH: 84
<212> TYPE: DNA
<213> ORGANISM: Homo sapiens

<400> SEQUENCE: 21

```
cccgtgaccc ggaagttgta cggctacgcg actttccctc ccacaaaccc tcgcgccctt    60
cctttcctac ttgggcccgg caga                                           84
```

<210> SEQ ID NO 22
<211> LENGTH: 89
<212> TYPE: DNA
<213> ORGANISM: Artificial Sequence
<220> FEATURE:
<223> OTHER INFORMATION: Modified 5'UTR

<400> SEQUENCE: 22

```
cttcctttg tgactggcgg tgaacgagtg cgcagtgcca catttgcttc tgacacaact     60
gtgttcacta gcaacctcaa acagacacc                                      89
```

<210> SEQ ID NO 23
<211> LENGTH: 96
<212> TYPE: DNA
<213> ORGANISM: Dengue virus

<400> SEQUENCE: 23
agttgttagt ctacgtggac cgacaaagac agattctttg agggagctaa gctcaacgta     60
gttctaacag ttttttaatt agagagcaga tctctg                              96

<210> SEQ ID NO 24
<211> LENGTH: 110
<212> TYPE: DNA
<213> ORGANISM: Arabidopsis thaliana

<400> SEQUENCE: 24
gggcttttcg cctttagggg gttctcatta tataaagatg acaacaccag taggaaaaca     60
agtcagtaag taaacgagca aaagaagaag agaaacaaca agaagtagta                110

<210> SEQ ID NO 25
<211> LENGTH: 111
<212> TYPE: DNA
<213> ORGANISM: Mus musculus

<400> SEQUENCE: 25
tataaaaccc ggcggcgcaa cgcgcagcca ctgtcgagtc gcgtccaccc gcgagcacag     60
cttctttgca gctccttcgt tgccggtcca cacccgccac cagttcgccc c              111

<210> SEQ ID NO 26
<211> LENGTH: 111
<212> TYPE: DNA
<213> ORGANISM: Artificial Sequence
<220> FEATURE:
<223> OTHER INFORMATION: Modified 5'UTR

<400> SEQUENCE: 26
ggcgaactgg tggcgggtgt ggaccggcaa cgaaggagct gcaaagaagc tgtgctcgcg     60
ggtggacgcg actcgacagt ggctgcgcgt tgcgccgccg ggttttatac c              111

<210> SEQ ID NO 27
<211> LENGTH: 112
<212> TYPE: DNA
<213> ORGANISM: Artificial Sequence
<220> FEATURE:
<223> OTHER INFORMATION: Modified 5'UTR

<400> SEQUENCE: 27
gggaaataag agagaaaaga agagtaagaa gaaatataag agccacccgc ctcgccgcct     60
ccacatttgc ttctgacaca actgtgttca ctagcaacct caaacagaca cc             112

<210> SEQ ID NO 28
<211> LENGTH: 121
<212> TYPE: DNA
<213> ORGANISM: Artificial Sequence
<220> FEATURE:
<223> OTHER INFORMATION: Modified 5'UTR

<400> SEQUENCE: 28
ctcagcccgt agcccgtcgg ttccggagta agttccaggt ggcccagcag tgggtgtgga     60
aggggaggat catcagaccc actgacacag acccaagaca gcaagaagct aaccaggcac    120
c                                                                    121

<210> SEQ ID NO 29
<211> LENGTH: 125
<212> TYPE: DNA
<213> ORGANISM: Artificial Sequence
<220> FEATURE:
<223> OTHER INFORMATION: Modified 5'UTR

<400> SEQUENCE: 29

```
cgcgttattg ttctgccggg cggacacgtg acgcgaagct taccgccgag accgcgtccg    60
ccccgcgagc acagagcctc gcctttgccg atccgccgcc cgtccacacc cgccgccagc   120
tcacc                                                              125
```

<210> SEQ ID NO 30
<211> LENGTH: 137
<212> TYPE: DNA
<213> ORGANISM: Homo sapiens

<400> SEQUENCE: 30

```
agcaccacgg cagcaggagg tttcggctaa gttggaggta ctggccacga ctgcatgccc    60
gcgcccgcca ggtgatacct ccgccggtga cccaggggct ctgcgacaca aggagtctgc   120
atgtctaagt gctagac                                                 137
```

<210> SEQ ID NO 31
<211> LENGTH: 140
<212> TYPE: DNA
<213> ORGANISM: Barley yellow dwarf virus

<400> SEQUENCE: 31

```
gtgaagattg accatctcac aaaagctgtt acgtgcttgt aacacactac gcgcccgttt    60
tgtattcggg aagtagttgc gaaaacggtc cccttattgc ctgacaagct aagggccacc   120
cttctttccc caccgccatc                                              140
```

<210> SEQ ID NO 32
<211> LENGTH: 149
<212> TYPE: DNA
<213> ORGANISM: Artificial Sequence
<220> FEATURE:
<223> OTHER INFORMATION: Modified 5'UTR

<400> SEQUENCE: 32

```
attaaaggtt tataccttcc caggtaacaa accaaccaac tttcgatctc ttgtagatct    60
gttctctaaa cgaactttaa aatctgtgtg gctgtcactc ggctgcttgc ttagtgcact   120
cacgcagtat aattaataac taattactg                                    149
```

<210> SEQ ID NO 33
<211> LENGTH: 152
<212> TYPE: DNA
<213> ORGANISM: Artificial Sequence
<220> FEATURE:
<223> OTHER INFORMATION: Modified 5'UTR

<400> SEQUENCE: 33

```
cgcgttattg ttctgccggg cggacacgtg acgcgaagct ttataaaacc cggcggcgca    60
acgcgcagcc actgtcgagt cgcgtccacc cgcgagcaca gcttctttgc agctccttcg   120
ttgccggtcc acaccgccca ccagttcgcc cc                                152
```

<210> SEQ ID NO 34
<211> LENGTH: 152

<212> TYPE: DNA
<213> ORGANISM: Artificial Sequence
<220> FEATURE:
<223> OTHER INFORMATION: Modified 5'UTR

<400> SEQUENCE: 34

```
cgcgttattg ttctgccggg cggacacgtg acgcgaagct tggcgaactg gtggcgggtg    60
tggaccggca acgaaggagc tgcaaagaag ctgtgctcgc gggtggacgc gactcgacag   120
tggctgcgcg ttgcgccgcc gggttttata cc                                 152
```

<210> SEQ ID NO 35
<211> LENGTH: 185
<212> TYPE: DNA
<213> ORGANISM: Artificial Sequence
<220> FEATURE:
<223> OTHER INFORMATION: Modified 5'UTR

<400> SEQUENCE: 35

```
attaaaggtt tataccttcc caggtaacaa accaaccaac tttcgatctc ttgtagatct    60
gttctctaaa cgaactttaa atctgtgtg gctgtcactc ggctgcttgc ttagtgcact   120
cacgcagtat aattaataac taattactgt cgttgacagg acacgagtaa ctcgtctatc   180
ttaag                                                               185
```

<210> SEQ ID NO 36
<211> LENGTH: 190
<212> TYPE: DNA
<213> ORGANISM: Artificial Sequence
<220> FEATURE:
<223> OTHER INFORMATION: Modified 5'UTR

<400> SEQUENCE: 36

```
tttaaaatct gtgtggctgt cactcggctg cttgcttagt gcactcacgc agtataatta    60
ataactaatt actgtcgttg acaggacacg agtaactcgt ctatcttctg caggctgctt   120
acggtttcgt ccgtgttgca gccgatcatc agcacatcta ggtttcgtcc gggtgtgacc   180
gaaaggtaag                                                          190
```

<210> SEQ ID NO 37
<211> LENGTH: 191
<212> TYPE: DNA
<213> ORGANISM: Artificial Sequence
<220> FEATURE:
<223> OTHER INFORMATION: Modified 5'UTR

<400> SEQUENCE: 37

```
cttccttttg tgactggcgg tgaacgagtg cgcagtgccc gcgttattgt tctgccgggc    60
ggacacgtga cgcgaagctt tataaaaccc ggcggcgcaa cgcgcagcca ctgtcgagtc   120
gcgtccaccc gcgagcacag cttctttgca gctccttcgt tgccggtcca cacccgccac   180
cagttcgccc c                                                        191
```

<210> SEQ ID NO 38
<211> LENGTH: 199
<212> TYPE: DNA
<213> ORGANISM: Artificial Sequence
<220> FEATURE:
<223> OTHER INFORMATION: Modified 5'UTR

<400> SEQUENCE: 38

```
gggaaataag agagaaaaga agagtaagaa gaaatataag agccaccgc gttattgttc    60
```

```
tgccgggcgg acacgtgacg cgaagcttta taaaacccgg cggcgcaacg cgcagccact    120
gtcgagtcgc gtccacccgc gagcacagct tctttgcagc tccttcgttg ccggtccaca    180
cccgccacca gttcgcccc                                                 199
```

<210> SEQ ID NO 39
<211> LENGTH: 199
<212> TYPE: DNA
<213> ORGANISM: Artificial Sequence
<220> FEATURE:
<223> OTHER INFORMATION: Modified 5'UTR

<400> SEQUENCE: 39

```
cgcgttattg ttctgccggg cggacacgtg acgcgaagct tgggaaataa gagagaaaag     60
aagagtaaga agaaatataa agccaccta taaaacccgg cggcgcaacg cgcagccact    120
gtcgagtcgc gtccacccgc gagcacagct tctttgcagc tccttcgttg ccggtccaca    180
cccgccacca gttcgcccc                                                 199
```

<210> SEQ ID NO 40
<211> LENGTH: 202
<212> TYPE: DNA
<213> ORGANISM: Artificial Sequence
<220> FEATURE:
<223> OTHER INFORMATION: Modified 5'UTR

<400> SEQUENCE: 40

```
attaaaggtt tataccttcc caggtaacaa accaaccaac tttcgatctc ttgtagatct     60
gttctctaaa cgaactttaa aatctgtcgt tgacaggaca cgagtaactc gtctatcttc    120
tgcaggctgc ttacggtttc gtccgtgttg cagccgatca tcagcacatc taggtttcgt    180
ccgggtgtga ccgaaaggta ag                                             202
```

<210> SEQ ID NO 41
<211> LENGTH: 221
<212> TYPE: DNA
<213> ORGANISM: Artificial Sequence
<220> FEATURE:
<223> OTHER INFORMATION: Modified 5'UTR

<400> SEQUENCE: 41

```
attaaaggtt tataccttcc caggtaacaa accaaccaac tttcgatctc ttgtagatct     60
gttctctaaa cgaactttaa aattataatt ataactaat tactgtcgtt gacaggacac    120
gagtaactcg tctatcttct gcaggctgct tacggtttcg tccgtgttgc agccgatcat    180
cagcacatct aggtttcgtc cgggtgtgac cgaaaggtaa g                        221
```

<210> SEQ ID NO 42
<211> LENGTH: 222
<212> TYPE: DNA
<213> ORGANISM: Artificial Sequence
<220> FEATURE:
<223> OTHER INFORMATION: Modified 5'UTR

<400> SEQUENCE: 42

```
attaaaggtt tataccttcc caggtaacaa accaaccaac tttcgatctc ttgtagatct     60
gttctctaaa cgaactttaa aatctgtgtg gctgtcactc ggctgcttgc ttagtgcact    120
cacgcagtat aattaataac taattactgt cgttgacagg acacgagtaa ctcgtctatc    180
ttcgcacatc taggtttcgt ccgggtgtga ccgaaaggta ag                       222
```

```
<210> SEQ ID NO 43
<211> LENGTH: 225
<212> TYPE: DNA
<213> ORGANISM: Artificial Sequence
<220> FEATURE:
<223> OTHER INFORMATION: Modified 5'UTR

<400> SEQUENCE: 43
tttaaaatct gtgtggctgt cactcggctg cttgcttagt gcactcacgc agtataatta      60
ataactaatt actgtcgttg acaggacacg agtaactcgt ctatcttctg caggctgctt    120
acggtttcgt ccgtgttgca gccgatcatc agcacatcta ggtttcgtcc gggtgtgacc    180
gaaaggtaag ttggagagcc ttgtccctgg tttcaacgag aaaac                     225

<210> SEQ ID NO 44
<211> LENGTH: 230
<212> TYPE: DNA
<213> ORGANISM: Artificial Sequence
<220> FEATURE:
<223> OTHER INFORMATION: Modified 5'UTR

<400> SEQUENCE: 44
attaaaggtt tataccttcc caggtaacaa accaaccaac tttcgatctc ttgtagatct      60
gttctctaaa cgaactttaa aatctgtgtg gctgtcactc ggctgcttgc ttagtgcact    120
cacgcagtat aattaataac taattactgt cgttgacagg acacgagtaa ctcgtctatc    180
ttctgcaggc tgcttacggt ttcgtccgtg ttgcagccga tcatcagaag                230

<210> SEQ ID NO 45
<211> LENGTH: 238
<212> TYPE: DNA
<213> ORGANISM: Artificial Sequence
<220> FEATURE:
<223> OTHER INFORMATION: Modified 5'UTR

<400> SEQUENCE: 45
attaaaaacc aactttcgat ctcttgtaga tctgttctct aaacgaactt taaaatctgt      60
gtggctgtca ctcggctgct tgcttagtgc actcacgcag tataattaat aactaattac    120
tgtcgttgac aggacacgag taactcgtct atcttctgca ggctgcttac ggtttcgtcc    180
gtgttgcagc cgatcatcag cacatctagg tttcgtccgg gtgtgaccga aaggtaag       238

<210> SEQ ID NO 46
<211> LENGTH: 246
<212> TYPE: DNA
<213> ORGANISM: Artificial Sequence
<220> FEATURE:
<223> OTHER INFORMATION: Modified 5'UTR

<400> SEQUENCE: 46
attaaaggtt tataccttcc caggtaacaa accaaccaac tttcgatctc ttgtagatct      60
gttctctaaa cgaactttaa aatctgtgtg gctgtcactc ggctgcttgc ttagtgcact    120
cacgcagctg tcgttgacag gacacgagta actcgtctat cttctgcagg ctgcttacgg    180
tttcgtccgt gttgcagccg atcatcagca catctaggtt tcgtccgggt gtgaccgaaa    240
ggtaag                                                                246

<210> SEQ ID NO 47
<211> LENGTH: 250
<212> TYPE: DNA
<213> ORGANISM: Artificial Sequence
<220> FEATURE:
```

<223> OTHER INFORMATION: Modified 5'UTR

<400> SEQUENCE: 47

```
attaaaggtt tataccttcc caggtaacaa accaaccaac tttctgttct ctaaacgaac      60
tttaaaatct gtgtggctgt cactcggctg cttgcttagt gcactcacgc agtataatta     120
ataactaatt actgtcgttg acaggacacg agtaactcgt ctatcttctg caggctgctt     180
acggtttcgt ccgtgttgca gccgatcatc agcacatcta ggtttcgtcc gggtgtgacc     240
gaaaggtaag                                                             250
```

<210> SEQ ID NO 48
<211> LENGTH: 250
<212> TYPE: DNA
<213> ORGANISM: Artificial Sequence
<220> FEATURE:
<223> OTHER INFORMATION: Modified 5'UTR

<400> SEQUENCE: 48

```
attaaaggtt tataccttcc caggtaacaa accaaccaac tttcgatctc ttgtagatct      60
tttaaaatct gtgtggctgt cactcggctg cttgcttagt gcactcacgc agtataatta     120
ataactaatt actgtcgttg acaggacacg agtaactcgt ctatcttctg caggctgctt     180
acggtttcgt ccgtgttgca gccgatcatc agcacatcta ggtttcgtcc gggtgtgacc     240
gaaaggtaag                                                             250
```

<210> SEQ ID NO 49
<211> LENGTH: 265
<212> TYPE: DNA
<213> ORGANISM: Artificial Sequence
<220> FEATURE:
<223> OTHER INFORMATION: Modified 5'UTR

<400> SEQUENCE: 49

```
attaaaggtt tataccttcc caggtaacaa accaaccaac tttcgatctc ttgtagatct      60
gttctctaaa cgaactttaa aatctgtgtg gctgtcactc ggctgcatgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaag                                            265
```

<210> SEQ ID NO 50
<211> LENGTH: 265
<212> TYPE: DNA
<213> ORGANISM: Artificial Sequence
<220> FEATURE:
<223> OTHER INFORMATION: Modified 5'UTR

<400> SEQUENCE: 50

```
attaaaggtt tataccttcc caggtaacaa accaaccaac tttcgatctc ttgtagatct      60
gttctctaaa cgaactttaa aatctgtgtg gctgtcactc ggctgcttgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaag                                            265
```

<210> SEQ ID NO 51
<211> LENGTH: 270
<212> TYPE: DNA
<213> ORGANISM: Artificial Sequence

```
<220> FEATURE:
<223> OTHER INFORMATION: Modified 5'UTR

<400> SEQUENCE: 51
attaaaggtt tataccttcc caggtaacaa accaaccaac tttcgatctc ttgtagatct      60
gttctctaaa cgaactttaa aatctgtgtg gctgtcactc ggctgccgcg ttattgttct     120
gccgggcgga cacgtgacgc gtaactaatt actgtcgttg acaggacacg agtaactcgt     180
ctatcttctg caggctgctt acggtttcgt ccgtgttgca gccgatcatc agcacatcta     240
ggtttcgtcc gggtgtgacc gaaaggtaag                                      270

<210> SEQ ID NO 52
<211> LENGTH: 300
<212> TYPE: DNA
<213> ORGANISM: Artificial Sequence
<220> FEATURE:
<223> OTHER INFORMATION: Modified 5'UTR

<400> SEQUENCE: 52
attaaaggtt tataccttcc caggtaacaa accaaccaac tttcgatctc ttgtagatct      60
gttctctaaa cgaactttaa aatctgtgtg gctgtcactc ggctgcttgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaagttgga gagccttgtc cctggtttca acgagaaaac     300

<210> SEQ ID NO 53
<211> LENGTH: 323
<212> TYPE: DNA
<213> ORGANISM: Artificial Sequence
<220> FEATURE:
<223> OTHER INFORMATION: Modified 5'UTR

<400> SEQUENCE: 53
ttgatctttt aatcttcgtt ggccacaatt aaaacaaacc agatcgtgga gctgcgcgat      60
ccctttgcat aaaaacatat ggcttttgct ataaaaatta tgactgcaaa acaccgggcc     120
attaatagcg tgcggagtga tttacgcgtt attgttctgc cgggcggaca cgtgacgcgc     180
gtggccaatg ggggcgcggg cgccggcaac ttattaggtg actgtacttc acccccccct     240
ggtgccacca agttgttaca tgaaatctgc agtttcataa tttcggcggg tcgggctggg     300
ccggccaggc gcgggctact gca                                             323

<210> SEQ ID NO 54
<211> LENGTH: 398
<212> TYPE: DNA
<213> ORGANISM: Artificial Sequence
<220> FEATURE:
<223> OTHER INFORMATION: Modified 5'UTR

<400> SEQUENCE: 54
ttgggggcga cactccacca tagatcactc ccctgtgagg aactactgtc ttcacgcaga      60
aagcgtctag ccatggcgtt agtatgagtg tcgtgcagcc tccaggaccc ccctcccgg     120 gagagccata gtggtctgcg gaaccggtga gtacaccgga attgccagga cgaccgggtc     180
ctttcttgga ttaacccgct caatgcctgg agatttgggc gtgccccgc gagactgcta     240 gccgagtagt gttgggtcgc gaaaggcctt gtggtactgc ctgatagggt gcttgcgagt     300
gccccgggag gtctcgtaga ccgtgcatca tgagcacaaa tcctaaacct caaagaaaaa     360
```

```
ccaaacgtaa caagggcgaa ttcgttggta aagccacc                              398

<210> SEQ ID NO 55
<211> LENGTH: 418
<212> TYPE: DNA
<213> ORGANISM: Arabidopsis thaliana

<400> SEQUENCE: 55
ccaaggtaaa aaaaaggtat gaaagctcta tagtaagtaa aatataaatt ccccataagg       60
aaagggccaa gtccaccagg caagtaaaat gagcaagcac cactccacca tcacacaatt      120
tcactcatag ataacgataa gattcatgga attatcttcc acgtggcatt attccagcgg      180
ttcaagccga taagggtctc aacacctctc cttaggcctt tgtggccgtt accaagtaaa      240
attaacctca cacatatcca cactcaaaat ccaacggtgt agatcctagt ccacttgaat      300
ctcatgtatc ctagaccctc cgatcactcc aaagcttgtt ctcattgttg ttatcattat      360
atatagatga ccaaagcact agaccaaacc tcagtcacac aaagagtaaa gaagaaca       418

<210> SEQ ID NO 56
<211> LENGTH: 60
<212> TYPE: DNA
<213> ORGANISM: Sindbis virus

<400> SEQUENCE: 56
cgtctgcata actttattta tttcttttat taatcaacaa aattttgttt ttaacatttc       60

<210> SEQ ID NO 57
<211> LENGTH: 64
<212> TYPE: DNA
<213> ORGANISM: Artificial Sequence
<220> FEATURE:
<223> OTHER INFORMATION: Modified 3'UTR

<400> SEQUENCE: 57
cctcgccccg gacctgccct cccgccaggt gcacccacct gcaataaatg cagcgaagcc       60
ggga                                                                   64

<210> SEQ ID NO 58
<211> LENGTH: 68
<212> TYPE: DNA
<213> ORGANISM: Artificial Sequence
<220> FEATURE:
<223> OTHER INFORMATION: Modified 3'UTR

<400> SEQUENCE: 58
taaccctacc tcagtcgaat tggattgggt catactgttg tagggtaaa tttttctta        60 attcggag                                                               68

<210> SEQ ID NO 59
<211> LENGTH: 111
<212> TYPE: DNA
<213> ORGANISM: Homo sapiens

<400> SEQUENCE: 59
gctggagcct cggtggccat gcttcttgcc ccttgggcct ccccccagcc cctcctcccc       60
ttcctgcacc cgtaccccccg tggtctttga ataaagtctg agtgggcggc a              111

<210> SEQ ID NO 60
<211> LENGTH: 115
<212> TYPE: DNA
<213> ORGANISM: Artificial Sequence
```

-continued

```
<220> FEATURE:
<223> OTHER INFORMATION: Modified 3'UTR

<400> SEQUENCE: 60
cctcgccccg acctgccct cccgccaggt gcacccacct gcaataaatg cagcgaagcc    60
gggacctcgc cccggacctg ccctcccgcc aggtgcaccc acctgcaata aatgc        115

<210> SEQ ID NO 61
<211> LENGTH: 131
<212> TYPE: DNA
<213> ORGANISM: Artificial Sequence
<220> FEATURE:
<223> OTHER INFORMATION: Modified 3'UTR

<400> SEQUENCE: 61
ggtgcctttg agagtctact tttgctctct tcggaagaac ccttaggggt tcgtgcatgg    60
gcttgcatag caagtctaga tgcgggtacc gtacagtgtt gaaaaacact gtaaatctct   120
aaaagagacc a                                                        131

<210> SEQ ID NO 62
<211> LENGTH: 134
<212> TYPE: DNA
<213> ORGANISM: Homo sapiens

<400> SEQUENCE: 62
gctcgctttc ttgctgtcca atttctatta aaggttcctt tgttccctaa gtccaactac    60
taaactgggg gatattatga agggccttga gcatctggat tctgcctaat aaaaaacatt   120
tattttcatt gcaa                                                     134

<210> SEQ ID NO 63
<211> LENGTH: 163
<212> TYPE: DNA
<213> ORGANISM: Alfalfa mosaic virus

<400> SEQUENCE: 63
attagtcatt ggtaattcaa tgccaacctc cactgggtgg gttaaggttg aggtatagaa    60
tcctattcgc tcctgatagg agaaattcta tattgcttat atacgtgctt atgcacgtat   120
ataaatgctc atgctaaatt gcatgaatgc cctaaggga tgc                      163

<210> SEQ ID NO 64
<211> LENGTH: 174
<212> TYPE: DNA
<213> ORGANISM: Artificial Sequence
<220> FEATURE:
<223> OTHER INFORMATION: Modified 3'UTR

<400> SEQUENCE: 64
gattcgtcag tagggttgta aaggttttc ttttcctgag aaaacaacct tttgttttct     60
caggttttgc tttttggcct ttccctagct ttaaaaaaaa aaaagcaaaa gacgctggtg   120
gctggcactc ctggtttcca ggacggggtt caagtccctg cggtgtcttt gctt         174

<210> SEQ ID NO 65
<211> LENGTH: 175
<212> TYPE: DNA
<213> ORGANISM: Artificial Sequence
<220> FEATURE:
<223> OTHER INFORMATION: Modified 3'UTR

<400> SEQUENCE: 65
```

```
ggcagcagcg gaggtcatga aggttttcct tttcctgaga aaacaacacg tattgttttc     60
tcaggttttg cttttggcc tttttctagc ttaaaaaaaa aaaaagcaaa agatgctggt    120
ggttggcact cctggtttcc aggacggggt tcaaatccct gcggcgtctt tgctt         175
```

```
<210> SEQ ID NO 66
<211> LENGTH: 201
<212> TYPE: DNA
<213> ORGANISM: Barley yellow dwarf virus

<400> SEQUENCE: 66
gtcttagcaa gctctgagcc aggagatgga cataaaccat agcaatccaa cgtgtaaccg     60
caatggggca acaacaggt gaaccgtgtc cacgggcctg gttaccgaaa ggaaagccag    120
tatccaacac agcaatgtgt tggggggtcac accttcgggg tactcttaac gctgacactc    180
gaaagagcag ttcggcaacc c                                               201
```

```
<210> SEQ ID NO 67
<211> LENGTH: 223
<212> TYPE: DNA
<213> ORGANISM: Artificial Sequence
<220> FEATURE:
<223> OTHER INFORMATION: Modified 3'UTR

<400> SEQUENCE: 67
tttaacaccc ttcaggtgta gacccgtcat tgtgacgcgt gggttgaggt gccatgaatt     60
tgtcattcat ggtgcattta tctcaacagt tttccctaac cgcgcgttgc gcggcagggt    120
ttttactctg agagataaat gcctgctcac taaggtctat tagagacatt agtacgatcc    180
ggctaatagt cgctttggat gacctccaaa gcggcggatt cct                       223
```

```
<210> SEQ ID NO 68
<211> LENGTH: 235
<212> TYPE: DNA
<213> ORGANISM: Artificial Sequence
<220> FEATURE:
<223> OTHER INFORMATION: Modified 3'UTR

<400> SEQUENCE: 68
gctcgctttc ttgctgtcca atttctatta aaggttcctt tgttccctaa gtccaactac     60
taaactgggg gatattatga agggccttga gcatctggat tctgcctaat aaaaaacatt    120
tattttcatt gcaattgcca tgtgtatgtg ggttcgccca catactctga tgatccccaa    180
tcgtggcgtg tcggcctgct tcggcaggca ctggcgccgg gatcattcat ggcaa          235
```

```
<210> SEQ ID NO 69
<211> LENGTH: 239
<212> TYPE: DNA
<213> ORGANISM: Artificial Sequence
<220> FEATURE:
<223> OTHER INFORMATION: Modified 3'UTR

<400> SEQUENCE: 69
ggccaaaggc gtcgagtaga cgccaacaac ggaattgcgg gaaaggggtc aacagccgtt     60
cagtaccaag tctcagggga aactttgaga tggccttgca aagggtatgg taataagctg    120
acggacatgg tcctaaccac gcagccaagt cctaagtcaa cagatcttct gttgatatgg    180
atgcagttca aaaccaaacc gtcagcgagt agctgacaaa agaaacaac aacaacaac      239
```

```
<210> SEQ ID NO 70
<211> LENGTH: 255
```

<212> TYPE: DNA
<213> ORGANISM: Artificial Sequence
<220> FEATURE:
<223> OTHER INFORMATION: Modified 3'UTR

<400> SEQUENCE: 70

```
tacggtaata gtgtagtctt ctcatcttag tagttagctc tctcttatat taagaaaaga    60
aaacaaaaac ccccaggtcg ctttattttg acctgtgtta gggaccaaaa acggtggcag   120
cactgtctag ctgcgggcat tagactggaa aactagtgct ctttgggtaa ccactaaaat   180
cccgaaaggg tgggctgtgg tgaccttccg aactaaaaga tagcctccct cctcgcgcgg   240
gggggggggcc tgccc                                                   255
```

<210> SEQ ID NO 71
<211> LENGTH: 268
<212> TYPE: DNA
<213> ORGANISM: Homo sapiens

<400> SEQUENCE: 71

```
gctcgctttc ttgctgtcca atttctatta aaggttcctt tgttccctaa gtccaactac    60
taaactgggg gatattatga agggccttga gcatctggat tctgcctaat aaaaaacatt   120
tattttcatt gcaagctcgc tttcttgctg tccaatttct attaaaggtt cctttgttcc   180
ctaagtccaa ctactaaact gggggatatt atgaagggcc ttgagcatct ggattctgcc   240
taataaaaaa catttatttt cattgcaa                                      268
```

<210> SEQ ID NO 72
<211> LENGTH: 281
<212> TYPE: DNA
<213> ORGANISM: Artificial Sequence
<220> FEATURE:
<223> OTHER INFORMATION: Modified 3'UTR

<400> SEQUENCE: 72

```
ctaactattt gctttgtatt ttaagatttt gtaaatagaa aaatatataa ccccactcgt    60
aggtaaggat ttattgtata ttttatttag ttagttattc agtacttacg gccctattac   120
caacgggtat taatcacaaa cactttatcc ccataggatt cttttaaatt taaaattta   180
aataattaac gtcagagtcc catcggggct aacaggtttt tcgcactttt cctgctaact   240
gacagaagtg caatttggtt tttgattaat agttgttttc t                       281
```

<210> SEQ ID NO 73
<211> LENGTH: 319
<212> TYPE: DNA
<213> ORGANISM: Sindbis virus

<400> SEQUENCE: 73

```
ccgctacgcc ccaatgatcc gaccagcaaa actcgatgta cttccgagga actgatgtgc    60
ataatgcatc aggctggtac attagatccc cgcttaccgc gggcaatata gcaacactaa   120
aaactcgatg tacttccgag gaagcgcagt gcataatgct gcgcagtgtt gccacataac   180
cactatatta accatttatc tagcggacgc caaaaactca atgtatttct gaggaagcgt   240
ggtgcataat gccacgcagc gtctgcataa cttttattat ttcttttatt aatcaacaaa   300
attttgtttt taacatttc                                                319
```

<210> SEQ ID NO 74
<211> LENGTH: 328
<212> TYPE: DNA

<210> SEQ ID NO 74
<211> LENGTH: 328 (implied)
<212> TYPE: DNA
<213> ORGANISM: Artificial Sequence
<220> FEATURE:
<223> OTHER INFORMATION: Modified 3'UTR

<400> SEQUENCE: 74

```
gaccacacaa ggcagatggg ctatataaac gttttcgctt ttccgtttac gatatatagt      60
ctactcttgt gcagaatgaa ttctcgtaac tacatagcac aagtagatgt agttaacttt     120
aatctcacat agcaatcttt aatcagtgtg taacattagg gaggacttga aagagccacc     180
acatttcac cgaggccacg cggagtacga tcgagtgtac agtgaacaat gctagggaga      240
gctgcctata tggaagagcc ctaatgtgta aaattaattt tagtagtgct atccccatgt     300
gattttaata gcttcttagg agaatgac                                        328
```

<210> SEQ ID NO 75
<211> LENGTH: 451
<212> TYPE: DNA
<213> ORGANISM: Artificial Sequence
<220> FEATURE:
<223> OTHER INFORMATION: Modified 3'UTR

<400> SEQUENCE: 75

```
aaagcaaaac taacatgaaa caaggctaga agtcaggtcg gattaagcca tagtacggaa      60
aaaactatgc tacctgtgag ccccgtccaa ggacgttaaa agaagtcagg ccatcataaa     120
tgccatagct tgagtaaact atgcagcctg tagctccacc tgagaaggtg taaaaaatcc     180
gggaggccac aaaccatgga agctgtacgc atggcgtagt ggactagcgg ttagaggaga     240
cccctccctt acaaatcgca gcaacaatgg gggcccaagg cgagatgaag ctgtagtctc     300
gctggaagga ctagaggtta gaggagaccc cccgaaaca aaaacagca tattgacgct       360
gggaaagacc agagatcctg ctgtctcctc agcatcattc caggcacaga acgccagaaa     420
atggaatggt gctgttgaat caacaggttc t                                    451
```

<210> SEQ ID NO 76
<211> LENGTH: 457
<212> TYPE: DNA
<213> ORGANISM: Artificial Sequence
<220> FEATURE:
<223> OTHER INFORMATION: Modified 3'UTR

<400> SEQUENCE: 76

```
aggccggtca tccttttgac acttcaagtc ccgaggataa cctcctctcg ggggttggggg      60
gaatcttggg atccagtagt cctccttgaa ctccatccaa cagggtagat ttaagagtca     120
tgagactttc attaatcatc tcagttgatc agacatggtc gtgtagattc tcataacacg     180
ggagatcttc tagcagtttc agtgaccaac ggtgctttcc ttctccagga actgataccg     240
aagttgttgg acaagccaag gggtgcttcg gattactctg tgcttgggca cagaaagagg     300
tcgtagtttg ccccttgata gcagattcaa catgaattaa ctaagaaagg cgatctgcct     360
cccatgaagg acataagcaa tagttcacaa tcatcttgca tctcagtgaa gtgtacataa     420
ctataaaggg ctgggtcatc taagcatttc agtcgag                              457
```

<210> SEQ ID NO 77
<211> LENGTH: 597
<212> TYPE: DNA
<213> ORGANISM: Woodchuck hepatitis virus

<400> SEQUENCE: 77

```
tcgacaatca acctctggat tacaaaattt gtgaaagatt gactggtatt cttaactatg      60
```

| | |
|---|---|
| ttgctcctttt tacgctatgt ggatacgctg ctttaatgcc tttgtatcat gctattgctt | 120 |
| cccgtatggc tttcattttc tcctccttgt ataaatcctg gttgctgtct ctttatgagg | 180 |
| agttgtggcc cgttgtcagg caacgtggcg tggtgtgcac tgtgtttgct gacgcaaccc | 240 |
| ccactggttg gggcattgcc accacctgtc agctcctttc cgggactttc gctttccccc | 300 |
| tccctattgc cacggcggaa ctcatcgccg cctgccttgc ccgctgctgg acaggggctc | 360 |
| ggctgttggg cactgacaat tccgtggtgt tgtcggggaa gctgacgtcc tttccatggc | 420 |
| tgctcgcctg tgttgccacc tggattctgc gcgggacgtc cttctgctac gtcccttcgg | 480 |
| ccctcaatcc agcggacctt ccttcccgcg gcctgctgcc ggctctgcgg cctcttccgc | 540 |
| gtcttcgcct tcgccctcag acgagtcgga tctccctttg ggccgcctcc ccgcctg | 597 |

<210> SEQ ID NO 78
<211> LENGTH: 600
<212> TYPE: DNA
<213> ORGANISM: Homo sapiens

<400> SEQUENCE: 78

| | |
|---|---|
| gcggactatg acttagttgc gttacaccct ttcttgacaa aacctaactt gcgcagaaaa | 60 |
| caagatgaga ttggcatggc tttatttgtt tttttttgttt tgttttggtt tttttttttt | 120 |
| ttttggcttg actcaggatt taaaaactgg aacggtgaag gtgacagcag tcggttggag | 180 |
| cgagcatccc ccaaagttca caatgtggcc gaggactttg attgcacatt gttgtttttt | 240 |
| taatagtcat tccaaatatg agatgcgttg ttacaggaag tcccttgcca tcctaaaagc | 300 |
| caccccactt ctctctaagg agaatggccc agtcctctcc caagtccaca caggggaggt | 360 |
| gatagcattg cttccgtgta aattatgtaa tgcaaaattt ttttaatctt cgccttaata | 420 |
| cttttttatt ttgttttatt ttgaatgatg agccttcgtg ccccccttc cccttttttt | 480 |
| gtccccccaac ttgagatgta tgaaggcttt tggtctccct gggagtgggt ggaggcagcc | 540 |
| agggcttacc tgtacactga cttgagacca gttgaataaa agtgcacacc ttaaaaatga | 600 |

<210> SEQ ID NO 79
<211> LENGTH: 682
<212> TYPE: DNA
<213> ORGANISM: Mus musculus

<400> SEQUENCE: 79

| | |
|---|---|
| gcggactgtt actgagctgc gttttacacc ctttctttga caaaacctaa cttgcgcaga | 60 |
| aaaaaaaaaa ataagagaca acattggcat ggctttgttt tttaaattt tttttaaagt | 120 |
| tttttttttt tttttttttt tttttttaa gttttttgt tttgttttgg cgcttttgac | 180 |
| tcaggattta aaaactggaa cggtgaaggc gacagcagtt ggttggagca acatccccc | 240 |
| aaagttctac aaatgtggct gaggactttg tacattgttt tgtttttttt tttttttggt | 300 |
| tttgtctttt tttaatagtc attccaagta tccatgaaat aagtggttac aggaagtccc | 360 |
| tcaccctccc aaaagccacc cccactccta agaggaggat ggtcgcgtcc atgccctgag | 420 |
| tccaccccgg ggaaggtgac agcattgctt ctgtgtaaat tatgtactgc aaaaattttt | 480 |
| ttaaatcttc cgccttaata cttcattttt gtttttaatt tctgaatggc ccaggtctga | 540 |
| ggcctccctt ttttttgtcc cccaacttg atgtatgaag ctttggtct ccctgggagg | 600 |
| gggttgaggt gttgaggcag ccagggctgg cctgtacact gacttgagac caataaaagt | 660 |
| gcacacctta ccttacacaa ac | 682 |

<210> SEQ ID NO 80
<211> LENGTH: 839
<212> TYPE: DNA
<213> ORGANISM: Homo sapiens

<400> SEQUENCE: 80

| | |
|---|---|
| atgaactcaa tctaaattaa aaagaaaga aatttgaaaa aactttctct ttgccatttc | 60 |
| ttcttcttct tttttaactg aaagctgaat ccttccattt cttctgcaca tctacttgct | 120 |
| taaattgtgg gcaaaagaga aaaagaagga ttgatcagag cattgtgcaa tacagtttca | 180 |
| ttaactcctt cccccgctcc cccaaaaatt tgaatttttt tttcaacact cttacacctg | 240 |
| ttatggaaaa tgtcaacctt gtaagaaaa ccaaaataaa aattgaaaaa taaaaaccat | 300 |
| aaacatttgc accacttgtg cttttgaat atcttccaca gagggaagtt taaaacccaa | 360 |
| acttccaaag gtttaaacta cctcaaaaca ctttcccatg agtgtgatcc acattgttag | 420 |
| gtgctgacct agacagagat gaactgaggt ccttgttttg ttttgttcat aatacaaagg | 480 |
| tgctaattaa tagtatttca gatacttgaa gaatgttgat ggtgctagaa gaatttgaga | 540 |
| agaaatactc ctgtattgag ttgtatcgtg tggtgtattt tttaaaaaat ttgatttagc | 600 |
| attcatattt tccatcttat tcccaattaa agtatgcag attatttgcc caaatcttct | 660 |
| tcagattcag catttgttct ttgccagtct catttttcatc ttcttccatg gttccacaga | 720 |
| agctttgttt cttgggcaag cagaaaaatt aaattgtacc tattttgtat atgtgagatg | 780 |
| tttaaataaa ttgtgaaaaa aatgaaataa agcatgtttg gttttccaaa agaacatat | 839 |

<210> SEQ ID NO 81
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 81

| | |
|---|---|
| acatttgctt ctgacacaac tgtgttcaca gttggaacaa tcgtgaaggt ggttgttaat | 60 |
| cagtgccacc | 70 |

<210> SEQ ID NO 82
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 82

| | |
|---|---|
| acatttgctt ctgacacaac tgtgttcact ttgctaaccg gggaatctac gtctatagcg | 60 |
| atcagccacc | 70 |

<210> SEQ ID NO 83
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 83

| | |
|---|---|
| acatttgctt ctgacacaac tgtgttcacg tgatccacag tcgttcgcca agagctatca | 60 |
| gacagccacc | 70 |

```
<210> SEQ ID NO 84
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 84
acatttgctt ctgacacaac tgtgttcacg cctcaaggtg tcgtacgggc taatgccgca    60
tgttgctacc                                                          70

<210> SEQ ID NO 85
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 85
acatttgctt ctgacacaac tgtgttcact actcatagtg atgcatcatc cgataggtgc    60
ggacaccacc                                                          70

<210> SEQ ID NO 86
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 86
acatttgctt ctgacacaac tgtgttcact cacaaataag ctttgttatc gcattaaagg    60
ccttgccacc                                                          70

<210> SEQ ID NO 87
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 87
acatttgctt ctgacacaac tgtgttcacg cagcagtcgt cattccatcg gtttcgttct    60
gggtgtcact                                                          70

<210> SEQ ID NO 88
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 88
acatttgctt ctgacacaac tgtgttcact tcggcgtgga catctgtgag gccaagtata    60
acttgccacc                                                          70

<210> SEQ ID NO 89
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 89
```

```
acatttgctt ctgacacaac tgtgttcact tcttcgtgac ttggtctagg tgcggtaagg    60
gttagccacc                                                           70

<210> SEQ ID NO 90
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 90
acatttgctt ctgacacaac tgtgttcact gcacagcatg gtcaaggagt actgtgtacg    60
tcctgccact                                                           70

<210> SEQ ID NO 91
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 91
acatttgctt ctgacacaac tgtgttcact agtcttgaag aagccttctt gagacctcgt    60
tcttgccacc                                                           70

<210> SEQ ID NO 92
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 92
acatttgctt ctgacacaac tgtgttcact ggtccattgc cttggttgat ctgttggata    60
ggcagccacc                                                           70

<210> SEQ ID NO 93
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 93
acatttgctt ctgacacaac tgtgttcacc agtacagtct ctgaagccac tacctaaata    60
cgttgccacc                                                           70

<210> SEQ ID NO 94
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 94
acatttgctt ctgacacaac tgtgttcact ggttgttcgt ggtgtggcaa tggtcttgac    60
ttgtgccacc                                                           70

<210> SEQ ID NO 95
<211> LENGTH: 70
<212> TYPE: DNA
<213> ORGANISM: Artificial Sequence
```

```
<220> FEATURE:
<223> OTHER INFORMATION: Modified 5'UTR

<400> SEQUENCE: 95
acatttgctt ctgacacaac tgtgttcacc aggcttgtgt taggttcgag tcgtgtaatt    60
acacgccacc                                                           70

<210> SEQ ID NO 96
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 96
acatttgctt ctgacacaac tgtgttcact ctggcacaga ctgcacttcc gtatacgcta    60
cattgccacc                                                           70

<210> SEQ ID NO 97
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 97
acatttgctt ctgacacaac tgtgttcaca gtgggtcagt agcatgccgg ctaacgttct    60
gtatgccacc                                                           70

<210> SEQ ID NO 98
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 98
acatttgctt ctgacacaac tgtgttcact gacttggggg tggtctttga tgaggttgtg    60
ttctgccacc                                                           70

<210> SEQ ID NO 99
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 99
acatttgctt ctgacacaac tgtgttcacc aacagttttg gttttccttg tccgattctt    60
tcctgccacc                                                           70

<210> SEQ ID NO 100
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 100
acatttgctt ctgacacaac tgtgttcact ggtacgcagc accatgggag tgcattggtg    60
tgttgccagt                                                           70
```

```
<210> SEQ ID NO 101
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 101
acatttgctt ctgacacaac tgtgttcacc tgatcgtgta ggattgagac ttgtcgtaag    60
ttcagccacc                                                          70

<210> SEQ ID NO 102
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 102
acatttgctt ctgacacaac tgtgttcacg ggcatgtgag tggttaacat gtggctattg    60
ttccgccacc                                                          70

<210> SEQ ID NO 103
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 103
acatttgctt ctgacacaac tgtgttcact gtgtcattgg gcgaatagct ggaacttcgc    60
gccagccacc                                                          70

<210> SEQ ID NO 104
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 104
acatttgctt ctgacacaac tgtgttcact ggtgggctaa ggcgtcagaa atcaaagcgt    60
ttttgccacc                                                          70

<210> SEQ ID NO 105
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 105
acatttgctt ctgacacaac tgtgttcact ggttcgaatt tggacgtcgc ctgcatggtc    60
ttctgccacc                                                          70

<210> SEQ ID NO 106
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 106
```

```
acatttgctt ctgacacaac tgtgttcact gcgccctggc aggcacttgc aaagtcttgg    60
tagcaccacc                                                          70

<210> SEQ ID NO 107
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 107
acatttgctt ctgacacaac tgtgttcact tagtgagcac gtgagctggt ttcgagtttg    60
taaagccacc                                                          70

<210> SEQ ID NO 108
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 108
acatttgctt ctgacacaac tgtgttcacg agttgtgcac ttgggtgata tttggcctca    60
gaaagccacc                                                          70

<210> SEQ ID NO 109
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 109
acatttgctt ctgacacaac tgtgttcacg ctgcaactgc cattctcgct tggatggtca    60
gaatgccacc                                                          70

<210> SEQ ID NO 110
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 110
acatttgctt ctgacacaac tgtgttcacg ggcggttgtg tttgtgatgt catgttcgca    60
ttcagccacc                                                          70

<210> SEQ ID NO 111
<211> LENGTH: 70
<212> TYPE: DNA
<213> ORGANISM: Artificial Sequence
<220> FEATURE:
<223> OTHER INFORMATION: Modified 5'UTR

<400> SEQUENCE: 111
acatttgctt ctgacacaac tgtgttcact cgacacggtt ctgagtccag aacatgagag    60
taatgccacc                                                          70

<210> SEQ ID NO 112
<211> LENGTH: 621
<212> TYPE: DNA
```

<213> ORGANISM: Artificial Sequence
<220> FEATURE:
<223> OTHER INFORMATION: Nanoluciferase reporter gene

<400> SEQUENCE: 112

```
atggccgttt acccatacga tgttcctgac tatgcgggct atccctatga cgtcccggac    60
tatgcaggct cctatccata tgacgttcca gattacgctg atctggcgt cttcacactc   120
gaagatttcg ttggggactg gcgacagaca gccggctaca acctggacca agtccttgaa   180
cagggaggtg tgtccagttt gtttcagaat ctcggggtgt ccgtaactcc gatccaaagg   240
attgtcctga gcggtgaaaa tgggctgaag atcgacatcc atgtcatcat cccgtatgaa   300
ggtctgagcg cgaccaaat gggccagatc gaaaaattt ttaaggtggt gtaccctgtg   360
gatgatcatc actttaaggt gatcctgcac tatggcacac tggtaatcga cggggttacg   420
ccgaacatga tcgactattt cggacggccg tatgaaggca tcgccgtgtt cgacggcaaa   480
aagatcactg taacagggac cctgtggaac ggcaacaaaa ttatcgacga gcgcctgatc   540
aaccccgacg gctccctgct gttccgagta accatcaacg gagtgaccgg ctggcggctg   600
tgcgaacgca ttctggcgta a                                              621
```

<210> SEQ ID NO 113
<211> LENGTH: 855
<212> TYPE: DNA
<213> ORGANISM: Artificial Sequence
<220> FEATURE:
<223> OTHER INFORMATION: GFP reporter gene

<400> SEQUENCE: 113

```
atggtttcta agggagaaga actgttcact ggtgtagtac ctatcctggt agaactggat    60
ggagatgtta acgccataa gttcagtgtt tctggagaag gagaaggtga tgctacttac   120
ggtaagctga cactgaagtt catctgtaca actggaaagc tgccagttcc ttggcctaca   180
ctggtaacaa ctctgactta cggagtacaa tgtttctctc gatacccaga tcatatgaag   240
caacatgatt tcttcaagtc agcaatgcct gaaggttacg tacaagaaag aactatcttc   300
ttcaaggatg atggtaacta caagactaga gctgaagtaa agttcgaagg agatactctg   360
gttaacagaa tcgaactgaa gggtatcgat ttcaaggaag atggaaacat cctgggtcat   420
aagctggaat acaactacaa ctcacataac gtatacatca tggcagataa gcaaaagaac   480
ggaatcaagg taaacttcaa gatcagacat aacatcgaag atggttcagt acaactggca   540
gatcattacc aacaaaacac acctatcgga gatggacctg tactgctgcc agataaccat   600
tacctgtcaa ctcaatctgc actgtcaaag gatcctaacg aaaagagaga tcatatggta   660
ctgctggaat tcgtaacagc tgcaggaatc actctgggta tggatgaact gtacaagaga   720
agtagagata tctctcatgg tttcccacct gctgtagctg cacaagatga tggtacactg   780
cctatgagtt gtgctcaaga atctggaatg gatagacatc tgcagcttg tgcatcagca   840
agaatcaacg tataa                                                    855
```

<210> SEQ ID NO 114
<211> LENGTH: 144
<212> TYPE: DNA
<213> ORGANISM: Artificial Sequence
<220> FEATURE:
<223> OTHER INFORMATION: Multi-epitope vaccine

<400> SEQUENCE: 114

```
atgggggggct ccggtggttc ggggtaccag ccgtaccgcg tcgtggtgct gggcgggagc    60
```
ggcggcagcc cgtaccgggt tgtcgtgctc tcgttcgggg ggtctggggg atcccttagc    120 cccgctggt acttctacta ctaa    144

```
<210> SEQ ID NO 115
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 115 gcttag                                                               6

<210> SEQ ID NO 116
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 116 acgaac                                                               6

<210> SEQ ID NO 117
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 117 ttcgga                                                               6

<210> SEQ ID NO 118
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 118 cactgt                                                               6

<210> SEQ ID NO 119
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 119 attccg                                                               6

<210> SEQ ID NO 120
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 120 ttgcac                                                               6

<210> SEQ ID NO 121
```

```
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 121 agtacg                                                                      6

<210> SEQ ID NO 122
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 122 agaacc                                                                      6

<210> SEQ ID NO 123
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 123 catacg                                                                      6

<210> SEQ ID NO 124
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 124 tactgc                                                                      6

<210> SEQ ID NO 125
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 125 aggatc                                                                      6

<210> SEQ ID NO 126
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 126 acttgc                                                                      6

<210> SEQ ID NO 127
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 127
```

```
aacgtg                                                          6

<210> SEQ ID NO 128
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 128 cagaca                                                          6

<210> SEQ ID NO 129
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 129 atagcg                                                          6

<210> SEQ ID NO 130
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 130 gctaac                                                          6

<210> SEQ ID NO 131
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 131 ttcacg                                                          6

<210> SEQ ID NO 132
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 132 tgctga                                                          6

<210> SEQ ID NO 133
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 133 cgttag                                                          6

<210> SEQ ID NO 134
<211> LENGTH: 6
<212> TYPE: DNA
```

```
<213> ORGANISM: Artificial Sequence
<220> FEATURE:
<223> OTHER INFORMATION: Barcoding Sequence

<400> SEQUENCE: 134 cttgca                                                                    6

<210> SEQ ID NO 135
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 135 tgcagt                                                                    6

<210> SEQ ID NO 136
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 136 tcgtga                                                                    6

<210> SEQ ID NO 137
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 137 tgcatc                                                                    6

<210> SEQ ID NO 138
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 138 cggaagaaa                                                                 9

<210> SEQ ID NO 139
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 139 gcgaagaaa                                                                 9

<210> SEQ ID NO 140
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 140 ggcaagaaa                                                                 9
```

```
<210> SEQ ID NO 141
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 141 ggagagaaa                                                               9

<210> SEQ ID NO 142
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 142 ccagagaaa                                                               9

<210> SEQ ID NO 143
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 143 gaggagaaa                                                               9

<210> SEQ ID NO 144
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 144 acggagaaa                                                               9

<210> SEQ ID NO 145
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 145 ctggagaaa                                                               9

<210> SEQ ID NO 146
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 146 cacgagaaa                                                               9

<210> SEQ ID NO 147
<211> LENGTH: 9
<212> TYPE: DNA
<213> ORGANISM: Artificial Sequence
<220> FEATURE:
```

<223> OTHER INFORMATION: Barcoding Sequence

<400> SEQUENCE: 147 agcgagaaa                                                                 9

<210> SEQ ID NO 148
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 148 tccgagaaa                                                                 9

<210> SEQ ID NO 149
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 149 gtcgagaaa                                                                 9

<210> SEQ ID NO 150
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 150 cgtgagaaa                                                                 9

<210> SEQ ID NO 151
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 151 gctgagaaa                                                                 9

<210> SEQ ID NO 152
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 152 cgacagaaa                                                                 9

<210> SEQ ID NO 153
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 153 gcacagaaa                                                                 9

-continued

```
<210> SEQ ID NO 154
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 154 cagcagaaa                                                                  9

<210> SEQ ID NO 155
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 155 aggcagaaa                                                                  9

<210> SEQ ID NO 156
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 156 tcgcagaaa                                                                  9

<210> SEQ ID NO 157
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 157 gtgcagaaa                                                                  9

<210> SEQ ID NO 158
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 158 gaccagaaa                                                                  9

<210> SEQ ID NO 159
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 159 tgccagaaa                                                                  9

<210> SEQ ID NO 160
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 160 ctccagaaa                                                                9

<210> SEQ ID NO 161
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 161 ggtcagaaa                                                                9

<210> SEQ ID NO 162
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 162 cctcagaaa                                                                9

<210> SEQ ID NO 163
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 163 ccgtagaaa                                                                9

<210> SEQ ID NO 164
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 164 cgctagaaa                                                                9

<210> SEQ ID NO 165
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 165 gcctagaaa                                                                9

<210> SEQ ID NO 166
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 166 ggaaggaaa                                                                9

<210> SEQ ID NO 167
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 167 ccaaggaaa                                                                9

<210> SEQ ID NO 168
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 168 gagaggaaa                                                                9

<210> SEQ ID NO 169
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 169 aggaggaaa                                                                9

<210> SEQ ID NO 170
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 170 tcgaggaaa                                                                9

<210> SEQ ID NO 171
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 171 ctgaggaaa                                                                9

<210> SEQ ID NO 172
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 172 cacaggaaa                                                                9

<210> SEQ ID NO 173
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 173
``` tgcaggaaa                                                                        9

<210> SEQ ID NO 174
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 174 accaggaaa                                                                        9

<210> SEQ ID NO 175
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 175 gtcaggaaa                                                                        9

<210> SEQ ID NO 176
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 176 cgtaggaaa                                                                        9

<210> SEQ ID NO 177
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 177 gctaggaaa                                                                        9

<210> SEQ ID NO 178
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 178 gaacggaaa                                                                        9

<210> SEQ ID NO 179
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 179 agacggaaa                                                                        9

<210> SEQ ID NO 180
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 180 tcacggaaa                                                                       9

<210> SEQ ID NO 181
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 181 ctacggaaa                                                                       9

<210> SEQ ID NO 182
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 182 aagcggaaa                                                                       9

<210> SEQ ID NO 183
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 183 ttgcggaaa                                                                       9

<210> SEQ ID NO 184
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 184 taccggaaa                                                                       9

<210> SEQ ID NO 185
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 185 atccggaaa                                                                       9

<210> SEQ ID NO 186
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 186 catcggaaa                                                                       9

<210> SEQ ID NO 187
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 187 tgtcggaaa                                                                 9

<210> SEQ ID NO 188
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 188 actcggaaa                                                                 9

<210> SEQ ID NO 189
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 189 gttcggaaa                                                                 9

<210> SEQ ID NO 190
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 190 cgatggaaa                                                                 9

<210> SEQ ID NO 191
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 191 gcatggaaa                                                                 9

<210> SEQ ID NO 192
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 192 cagtggaaa                                                                 9

<210> SEQ ID NO 193
<211> LENGTH: 9
<212> TYPE: DNA
<213> ORGANISM: Artificial Sequence
<220> FEATURE:
<223> OTHER INFORMATION: Barcoding Sequence

```
<400> SEQUENCE: 193 tggtggaaa                                                                    9

<210> SEQ ID NO 194
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 194 acgtggaaa                                                                    9

<210> SEQ ID NO 195
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 195 gtgtggaaa                                                                    9

<210> SEQ ID NO 196
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 196 gactggaaa                                                                    9

<210> SEQ ID NO 197
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 197 agctggaaa                                                                    9

<210> SEQ ID NO 198
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 198 tcctggaaa                                                                    9

<210> SEQ ID NO 199
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 199 ctctggaaa                                                                    9

<210> SEQ ID NO 200
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 200 ggttggaaa                                                                  9

<210> SEQ ID NO 201
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 201 ccttggaaa                                                                  9

<210> SEQ ID NO 202
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 202 cgaacgaaa                                                                  9

<210> SEQ ID NO 203
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 203 gcaacgaaa                                                                  9

<210> SEQ ID NO 204
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 204 cagacgaaa                                                                  9

<210> SEQ ID NO 205
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 205 tggacgaaa                                                                  9

<210> SEQ ID NO 206
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 206
``` acgacgaaa                                                                    9

<210> SEQ ID NO 207
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 207 gtgacgaaa                                                                    9

<210> SEQ ID NO 208
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 208 gacacgaaa                                                                    9

<210> SEQ ID NO 209
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 209 agcacgaaa                                                                    9

<210> SEQ ID NO 210
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 210 tccacgaaa                                                                    9

<210> SEQ ID NO 211
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 211 ctcacgaaa                                                                    9

<210> SEQ ID NO 212
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 212 ggtacgaaa                                                                    9

<210> SEQ ID NO 213
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 213 cctacgaaa                                                                    9

<210> SEQ ID NO 214
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 214 gaagcgaaa                                                                    9

<210> SEQ ID NO 215
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 215 agagcgaaa                                                                    9

<210> SEQ ID NO 216
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 216 tcagcgaaa                                                                    9

<210> SEQ ID NO 217
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 217 ctagcgaaa                                                                    9

<210> SEQ ID NO 218
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 218 aaggcgaaa                                                                    9

<210> SEQ ID NO 219
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 219 ttggcgaaa                                                                    9
```

```
<210> SEQ ID NO 220
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 220 tacgcgaaa                                                                 9

<210> SEQ ID NO 221
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 221 atcgcgaaa                                                                 9

<210> SEQ ID NO 222
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 222 catgcgaaa                                                                 9

<210> SEQ ID NO 223
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 223 tgtgcgaaa                                                                 9

<210> SEQ ID NO 224
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 224 actgcgaaa                                                                 9

<210> SEQ ID NO 225
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 225 gttgcgaaa                                                                 9

<210> SEQ ID NO 226
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 226 caaccgaaa                                                                9

<210> SEQ ID NO 227
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 227 tgaccgaaa                                                                9

<210> SEQ ID NO 228
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 228 acaccgaaa                                                                9

<210> SEQ ID NO 229
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 229 gtaccgaaa                                                                9

<210> SEQ ID NO 230
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 230 tagccgaaa                                                                9

<210> SEQ ID NO 231
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 231 atgccgaaa                                                                9

<210> SEQ ID NO 232
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 232 gatccgaaa                                                                9
```

```
<210> SEQ ID NO 233
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 233 agtccgaaa                                                                  9

<210> SEQ ID NO 234
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 234 tctccgaaa                                                                  9

<210> SEQ ID NO 235
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 235 cttccgaaa                                                                  9

<210> SEQ ID NO 236
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 236 ggatcgaaa                                                                  9

<210> SEQ ID NO 237
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 237 ccatcgaaa                                                                  9

<210> SEQ ID NO 238
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 238 gagtcgaaa                                                                  9

<210> SEQ ID NO 239
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 239 aggtcgaaa                                                              9

<210> SEQ ID NO 240
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 240 tcgtcgaaa                                                              9

<210> SEQ ID NO 241
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 241 ctgtcgaaa                                                              9

<210> SEQ ID NO 242
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 242 cactcgaaa                                                              9

<210> SEQ ID NO 243
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 243 tgctcgaaa                                                              9

<210> SEQ ID NO 244
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 244 acctcgaaa                                                              9

<210> SEQ ID NO 245
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 245 gtctcgaaa                                                              9

<210> SEQ ID NO 246
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 246 cgttcgaaa                                                                9

<210> SEQ ID NO 247
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 247 gcttcgaaa                                                                9

<210> SEQ ID NO 248
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 248 ccgatgaaa                                                                9

<210> SEQ ID NO 249
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 249 cgcatgaaa                                                                9

<210> SEQ ID NO 250
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 250 gccatgaaa                                                                9

<210> SEQ ID NO 251
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 251 cgagtgaaa                                                                9

<210> SEQ ID NO 252
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 252
``` gcagtgaaa 9

<210> SEQ ID NO 253
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 253 caggtgaaa 9

<210> SEQ ID NO 254
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 254 tcggtgaaa 9

<210> SEQ ID NO 255
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 255 gtggtgaaa 9

<210> SEQ ID NO 256
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 256 gacgtgaaa 9

<210> SEQ ID NO 257
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 257 tgcgtgaaa 9

<210> SEQ ID NO 258
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 258 accgtgaaa 9

<210> SEQ ID NO 259
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 259 ctcgtgaaa                                                                  9

<210> SEQ ID NO 260
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 260 ggtgtgaaa                                                                  9

<210> SEQ ID NO 261
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 261 cctgtgaaa                                                                  9

<210> SEQ ID NO 262
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 262 ggactgaaa                                                                  9

<210> SEQ ID NO 263
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 263 ccactgaaa                                                                  9

<210> SEQ ID NO 264
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 264 gagctgaaa                                                                  9

<210> SEQ ID NO 265
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 265 tggctgaaa                                                                  9
```

```
<210> SEQ ID NO 266
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 266 acgctgaaa                                                                 9

<210> SEQ ID NO 267
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 267 ctgctgaaa                                                                 9

<210> SEQ ID NO 268
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 268 cacctgaaa                                                                 9

<210> SEQ ID NO 269
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 269 agcctgaaa                                                                 9

<210> SEQ ID NO 270
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 270 gtcctgaaa                                                                 9

<210> SEQ ID NO 271
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 271 cgtctgaaa                                                                 9

<210> SEQ ID NO 272
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 272 gctctgaaa                                                            9

<210> SEQ ID NO 273
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 273 cggttgaaa                                                            9

<210> SEQ ID NO 274
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 274 gcgttgaaa                                                            9

<210> SEQ ID NO 275
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 275 ggcttgaaa                                                            9

<210> SEQ ID NO 276
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 276 ccgaacaaa                                                            9

<210> SEQ ID NO 277
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 277 cgcaacaaa                                                            9

<210> SEQ ID NO 278
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 278 gccaacaaa                                                            9

<210> SEQ ID NO 279
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 279 cgagacaaa                                                                 9

<210> SEQ ID NO 280
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 280 gcagacaaa                                                                 9

<210> SEQ ID NO 281
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 281 caggacaaa                                                                 9

<210> SEQ ID NO 282
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 282 tcggacaaa                                                                 9

<210> SEQ ID NO 283
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 283 gtggacaaa                                                                 9

<210> SEQ ID NO 284
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 284 gacgacaaa                                                                 9

<210> SEQ ID NO 285
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 285
``` tgcgacaaa                                                                        9

<210> SEQ ID NO 286
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 286 accgacaaa                                                                        9

<210> SEQ ID NO 287
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 287 ctcgacaaa                                                                        9

<210> SEQ ID NO 288
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 288 ggtgacaaa                                                                        9

<210> SEQ ID NO 289
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 289 cctgacaaa                                                                        9

<210> SEQ ID NO 290
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 290 ggacacaaa                                                                        9

<210> SEQ ID NO 291
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 291 ccacacaaa                                                                        9

<210> SEQ ID NO 292
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 292 gagcacaaa                                                                    9

<210> SEQ ID NO 293
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 293 tggcacaaa                                                                    9

<210> SEQ ID NO 294
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 294 acgcacaaa                                                                    9

<210> SEQ ID NO 295
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 295 ctgcacaaa                                                                    9

<210> SEQ ID NO 296
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 296 caccacaaa                                                                    9

<210> SEQ ID NO 297
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 297 agccacaaa                                                                    9

<210> SEQ ID NO 298
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 298 gtccacaaa                                                                    9
```

<210> SEQ ID NO 299
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 299 cgtcacaaa                                                                 9

<210> SEQ ID NO 300
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 300 gctcacaaa                                                                 9

<210> SEQ ID NO 301
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 301 cggtacaaa                                                                 9

<210> SEQ ID NO 302
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 302 gcgtacaaa                                                                 9

<210> SEQ ID NO 303
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 303 ggctacaaa                                                                 9

<210> SEQ ID NO 304
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 304 cgaagcaaa                                                                 9

<210> SEQ ID NO 305
<211> LENGTH: 9
<212> TYPE: DNA
<213> ORGANISM: Artificial Sequence
<220> FEATURE:

<223> OTHER INFORMATION: Barcoding Sequence

<400> SEQUENCE: 305 gcaagcaaa                                                                              9

<210> SEQ ID NO 306
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 306 cagagcaaa                                                                              9

<210> SEQ ID NO 307
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 307 tggagcaaa                                                                              9

<210> SEQ ID NO 308
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 308 acgagcaaa                                                                              9

<210> SEQ ID NO 309
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 309 gtgagcaaa                                                                              9

<210> SEQ ID NO 310
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 310 gacagcaaa                                                                              9

<210> SEQ ID NO 311
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 311 agcagcaaa                                                                              9

```
<210> SEQ ID NO 312
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 312 tccagcaaa                                                                  9

<210> SEQ ID NO 313
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 313 ctcagcaaa                                                                  9

<210> SEQ ID NO 314
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 314 ggtagcaaa                                                                  9

<210> SEQ ID NO 315
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 315 cctagcaaa                                                                  9

<210> SEQ ID NO 316
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 316 gaaggcaaa                                                                  9

<210> SEQ ID NO 317
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 317 agaggcaaa                                                                  9

<210> SEQ ID NO 318
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 318 tcaggcaaa                                                              9

<210> SEQ ID NO 319
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 319 ctaggcaaa                                                              9

<210> SEQ ID NO 320
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 320 aacggcaaa                                                              9

<210> SEQ ID NO 321
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 321 ttcggcaaa                                                              9

<210> SEQ ID NO 322
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 322 catggcaaa                                                              9

<210> SEQ ID NO 323
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 323 tgtggcaaa                                                              9

<210> SEQ ID NO 324
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 324 actggcaaa                                                              9

<210> SEQ ID NO 325
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 325 gttggcaaa                                                                 9

<210> SEQ ID NO 326
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 326 caacgcaaa                                                                 9

<210> SEQ ID NO 327
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 327 tgacgcaaa                                                                 9

<210> SEQ ID NO 328
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 328 acacgcaaa                                                                 9

<210> SEQ ID NO 329
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 329 gtacgcaaa                                                                 9

<210> SEQ ID NO 330
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 330 tagcgcaaa                                                                 9

<210> SEQ ID NO 331
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 331
``` atgcgcaaa 9

<210> SEQ ID NO 332
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 332 gatcgcaaa 9

<210> SEQ ID NO 333
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 333 agtcgcaaa 9

<210> SEQ ID NO 334
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 334 tctcgcaaa 9

<210> SEQ ID NO 335
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 335 cttcgcaaa 9

<210> SEQ ID NO 336
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 336 ggatgcaaa 9

<210> SEQ ID NO 337
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 337 ccatgcaaa 9

<210> SEQ ID NO 338
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 338 gagtgcaaa                                                                 9

<210> SEQ ID NO 339
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 339 aggtgcaaa                                                                 9

<210> SEQ ID NO 340
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 340 tcgtgcaaa                                                                 9

<210> SEQ ID NO 341
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 341 ctgtgcaaa                                                                 9

<210> SEQ ID NO 342
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 342 cactgcaaa                                                                 9

<210> SEQ ID NO 343
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 343 tgctgcaaa                                                                 9

<210> SEQ ID NO 344
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 344 acctgcaaa                                                                 9

<210> SEQ ID NO 345
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 345 gtctgcaaa                                                                 9

<210> SEQ ID NO 346
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 346 cgttgcaaa                                                                 9

<210> SEQ ID NO 347
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 347 gcttgcaaa                                                                 9

<210> SEQ ID NO 348
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 348 ggaaccaaa                                                                 9

<210> SEQ ID NO 349
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 349 ccaaccaaa                                                                 9

<210> SEQ ID NO 350
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 350 gagaccaaa                                                                 9

<210> SEQ ID NO 351
<211> LENGTH: 9
<212> TYPE: DNA
<213> ORGANISM: Artificial Sequence
<220> FEATURE:
<223> OTHER INFORMATION: Barcoding Sequence

```
<400> SEQUENCE: 351 aggaccaaa                                                                9

<210> SEQ ID NO 352
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 352 tcgaccaaa                                                                9

<210> SEQ ID NO 353
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 353 ctgaccaaa                                                                9

<210> SEQ ID NO 354
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 354 cacaccaaa                                                                9

<210> SEQ ID NO 355
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 355 tgcaccaaa                                                                9

<210> SEQ ID NO 356
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 356 accaccaaa                                                                9

<210> SEQ ID NO 357
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 357 gtcaccaaa                                                                9

<210> SEQ ID NO 358
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 358 cgtaccaaa                                                                 9

<210> SEQ ID NO 359
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 359 gctaccaaa                                                                 9

<210> SEQ ID NO 360
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 360 caagccaaa                                                                 9

<210> SEQ ID NO 361
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 361 tgagccaaa                                                                 9

<210> SEQ ID NO 362
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 362 acagccaaa                                                                 9

<210> SEQ ID NO 363
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 363 gtagccaaa                                                                 9

<210> SEQ ID NO 364
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 364
```

```
taggccaaa                                                          9

<210> SEQ ID NO 365
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 365 atggccaaa                                                          9

<210> SEQ ID NO 366
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 366 gatgccaaa                                                          9

<210> SEQ ID NO 367
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 367 agtgccaaa                                                          9

<210> SEQ ID NO 368
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 368 tctgccaaa                                                          9

<210> SEQ ID NO 369
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 369 cttgccaaa                                                          9

<210> SEQ ID NO 370
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 370 cgatccaaa                                                          9

<210> SEQ ID NO 371
<211> LENGTH: 9
<212> TYPE: DNA
```

```
<213> ORGANISM: Artificial Sequence
<220> FEATURE:
<223> OTHER INFORMATION: Barcoding Sequence

<400> SEQUENCE: 371 gcatccaaa                                                                 9

<210> SEQ ID NO 372
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 372 cagtccaaa                                                                 9

<210> SEQ ID NO 373
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 373 tggtccaaa                                                                 9

<210> SEQ ID NO 374
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 374 acgtccaaa                                                                 9

<210> SEQ ID NO 375
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 375 gtgtccaaa                                                                 9

<210> SEQ ID NO 376
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 376 gactccaaa                                                                 9

<210> SEQ ID NO 377
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 377 agctccaaa                                                                 9
```

<210> SEQ ID NO 378
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 378 tcctccaaa                                                                 9

<210> SEQ ID NO 379
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 379 ctctccaaa                                                                 9

<210> SEQ ID NO 380
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 380 ggttccaaa                                                                 9

<210> SEQ ID NO 381
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 381 ccttccaaa                                                                 9

<210> SEQ ID NO 382
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 382 cggatcaaa                                                                 9

<210> SEQ ID NO 383
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 383 gcgatcaaa                                                                 9

<210> SEQ ID NO 384
<211> LENGTH: 9
<212> TYPE: DNA
<213> ORGANISM: Artificial Sequence
<220> FEATURE:

-continued

```
<223> OTHER INFORMATION: Barcoding Sequence

<400> SEQUENCE: 384 ggcatcaaa                                                              9

<210> SEQ ID NO 385
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 385 ggagtcaaa                                                              9

<210> SEQ ID NO 386
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 386 ccagtcaaa                                                              9

<210> SEQ ID NO 387
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 387 gaggtcaaa                                                              9

<210> SEQ ID NO 388
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 388 acggtcaaa                                                              9

<210> SEQ ID NO 389
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 389 ctggtcaaa                                                              9

<210> SEQ ID NO 390
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 390 cacgtcaaa                                                              9
```

```
<210> SEQ ID NO 391
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 391 agcgtcaaa                                                              9

<210> SEQ ID NO 392
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 392 tccgtcaaa                                                              9

<210> SEQ ID NO 393
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 393 gtcgtcaaa                                                              9

<210> SEQ ID NO 394
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 394 cgtgtcaaa                                                              9

<210> SEQ ID NO 395
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 395 gctgtcaaa                                                              9

<210> SEQ ID NO 396
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 396 cgactcaaa                                                              9

<210> SEQ ID NO 397
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 397 gcactcaaa                                                                9

<210> SEQ ID NO 398
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 398 cagctcaaa                                                                9

<210> SEQ ID NO 399
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 399 aggctcaaa                                                                9

<210> SEQ ID NO 400
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 400 tcgctcaaa                                                                9

<210> SEQ ID NO 401
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 401 gtgctcaaa                                                                9

<210> SEQ ID NO 402
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 402 gacctcaaa                                                                9

<210> SEQ ID NO 403
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 403 tgcctcaaa                                                                9

<210> SEQ ID NO 404
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 404 ctcctcaaa                                                                              9

<210> SEQ ID NO 405
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 405 ggtctcaaa                                                                              9

<210> SEQ ID NO 406
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 406 cctctcaaa                                                                              9

<210> SEQ ID NO 407
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 407 ccgttcaaa                                                                              9

<210> SEQ ID NO 408
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 408 cgcttcaaa                                                                              9

<210> SEQ ID NO 409
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 409 gccttcaaa                                                                              9

<210> SEQ ID NO 410
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 410
```

```
gcggataaa                                                          9

<210> SEQ ID NO 411
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 411 ggcgataaa                                                          9

<210> SEQ ID NO 412
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 412 cggcataaa                                                          9

<210> SEQ ID NO 413
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 413 cggagtaaa                                                          9

<210> SEQ ID NO 414
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 414 gcgagtaaa                                                          9

<210> SEQ ID NO 415
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 415 ggcagtaaa                                                          9

<210> SEQ ID NO 416
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 416 ggaggtaaa                                                          9

<210> SEQ ID NO 417
<211> LENGTH: 9
<212> TYPE: DNA
<213> ORGANISM: Artificial Sequence
```

```
<220> FEATURE:
<223> OTHER INFORMATION: Barcoding Sequence

<400> SEQUENCE: 417 ccaggtaaa                                                                 9

<210> SEQ ID NO 418
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 418 gacggtaaa                                                                 9

<210> SEQ ID NO 419
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 419 agcggtaaa                                                                 9

<210> SEQ ID NO 420
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 420 tccggtaaa                                                                 9

<210> SEQ ID NO 421
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 421 ctcggtaaa                                                                 9

<210> SEQ ID NO 422
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 422 cgtggtaaa                                                                 9

<210> SEQ ID NO 423
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 423 gctggtaaa                                                                 9
```

```
<210> SEQ ID NO 424
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 424 cgacgtaaa                                                                 9

<210> SEQ ID NO 425
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 425 gcacgtaaa                                                                 9

<210> SEQ ID NO 426
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 426 gagcgtaaa                                                                 9

<210> SEQ ID NO 427
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 427 aggcgtaaa                                                                 9

<210> SEQ ID NO 428
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 428 tcgcgtaaa                                                                 9

<210> SEQ ID NO 429
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 429 ctgcgtaaa                                                                 9

<210> SEQ ID NO 430
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 430 caccgtaaa                                                                9

<210> SEQ ID NO 431
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 431 tgccgtaaa                                                                9

<210> SEQ ID NO 432
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 432 gtccgtaaa                                                                9

<210> SEQ ID NO 433
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 433 ggtcgtaaa                                                                9

<210> SEQ ID NO 434
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 434 cctcgtaaa                                                                9

<210> SEQ ID NO 435
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 435 ccgtgtaaa                                                                9

<210> SEQ ID NO 436
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 436 cgctgtaaa                                                                9

<210> SEQ ID NO 437
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 437 gcctgtaaa                                                                  9

<210> SEQ ID NO 438
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 438 ccgactaaa                                                                  9

<210> SEQ ID NO 439
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 439 cgcactaaa                                                                  9

<210> SEQ ID NO 440
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 440 gccactaaa                                                                  9

<210> SEQ ID NO 441
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 441 cgagctaaa                                                                  9

<210> SEQ ID NO 442
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 442 gcagctaaa                                                                  9

<210> SEQ ID NO 443
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 443
``` gaggctaaa                                                                                   9

<210> SEQ ID NO 444
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 444 acggctaaa                                                                                   9

<210> SEQ ID NO 445
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 445 ctggctaaa                                                                                   9

<210> SEQ ID NO 446
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 446 cacgctaaa                                                                                   9

<210> SEQ ID NO 447
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 447 tgcgctaaa                                                                                   9

<210> SEQ ID NO 448
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 448 gtcgctaaa                                                                                   9

<210> SEQ ID NO 449
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 449 ggtgctaaa                                                                                   9

<210> SEQ ID NO 450
<211> LENGTH: 9
<212> TYPE: DNA

-continued

```
<213> ORGANISM: Artificial Sequence
<220> FEATURE:
<223> OTHER INFORMATION: Barcoding Sequence

<400> SEQUENCE: 450 cctgctaaa                                                                 9

<210> SEQ ID NO 451
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 451 ggacctaaa                                                                 9

<210> SEQ ID NO 452
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 452 ccacctaaa                                                                 9

<210> SEQ ID NO 453
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 453 cagcctaaa                                                                 9

<210> SEQ ID NO 454
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 454 tggcctaaa                                                                 9

<210> SEQ ID NO 455
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 455 gtgcctaaa                                                                 9

<210> SEQ ID NO 456
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 456 cgtcctaaa                                                                 9
```

```
<210> SEQ ID NO 457
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 457 gctcctaaa                                                               9

<210> SEQ ID NO 458
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 458 cggtctaaa                                                               9

<210> SEQ ID NO 459
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 459 gcgtctaaa                                                               9

<210> SEQ ID NO 460
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 460 ggctctaaa                                                               9

<210> SEQ ID NO 461
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 461 ccggttaaa                                                               9

<210> SEQ ID NO 462
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 462 cgcgttaaa                                                               9

<210> SEQ ID NO 463
<211> LENGTH: 9
<212> TYPE: DNA
<213> ORGANISM: Artificial Sequence
<220> FEATURE:
```

<223> OTHER INFORMATION: Barcoding Sequence

<400> SEQUENCE: 463 gccgttaaa                                                              9

<210> SEQ ID NO 464
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 464 gcgcttaaa                                                              9

<210> SEQ ID NO 465
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 465 ggcctttaaa                                                             9

<210> SEQ ID NO 466
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 466 ggagaagaa                                                              9

<210> SEQ ID NO 467
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 467 ccagaagaa                                                              9

<210> SEQ ID NO 468
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 468 gaggaagaa                                                              9

<210> SEQ ID NO 469
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 469 acggaagaa                                                              9

```
<210> SEQ ID NO 470
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 470 ctggaagaa                                                                9

<210> SEQ ID NO 471
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 471 cacgaagaa                                                                9

<210> SEQ ID NO 472
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 472 agcgaagaa                                                                9

<210> SEQ ID NO 473
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 473 tccgaagaa                                                                9

<210> SEQ ID NO 474
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 474 gtcgaagaa                                                                9

<210> SEQ ID NO 475
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 475 cgtgaagaa                                                                9

<210> SEQ ID NO 476
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 476 gctgaagaa                                                                    9

<210> SEQ ID NO 477
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 477 cgacaagaa                                                                    9

<210> SEQ ID NO 478
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 478 gcacaagaa                                                                    9

<210> SEQ ID NO 479
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 479 cagcaagaa                                                                    9

<210> SEQ ID NO 480
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 480 aggcaagaa                                                                    9

<210> SEQ ID NO 481
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 481 tcgcaagaa                                                                    9

<210> SEQ ID NO 482
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 482 gtgcaagaa                                                                    9

<210> SEQ ID NO 483
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 483 gaccaagaa                                                                 9

<210> SEQ ID NO 484
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 484 tgccaagaa                                                                 9

<210> SEQ ID NO 485
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 485 ctccaagaa                                                                 9

<210> SEQ ID NO 486
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 486 ggtcaagaa                                                                 9

<210> SEQ ID NO 487
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 487 cctcaagaa                                                                 9

<210> SEQ ID NO 488
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 488 cggtaagaa                                                                 9

<210> SEQ ID NO 489
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 489
```

-continued gcgtaagaa  9

<210> SEQ ID NO 490
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 490 ggctaagaa  9

<210> SEQ ID NO 491
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 491 ggaagagaa  9

<210> SEQ ID NO 492
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 492 ccaagagaa  9

<210> SEQ ID NO 493
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 493 gagagagaa  9

<210> SEQ ID NO 494
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 494 aggagagaa  9

<210> SEQ ID NO 495
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 495 tcgagagaa  9

<210> SEQ ID NO 496
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 496 ctgagagaa                                                                9

<210> SEQ ID NO 497
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 497 cacagagaa                                                                9

<210> SEQ ID NO 498
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 498 tgcagagaa                                                                9

<210> SEQ ID NO 499
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 499 accagagaa                                                                9

<210> SEQ ID NO 500
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 500 gtcagagaa                                                                9

<210> SEQ ID NO 501
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 501 cgtagagaa                                                                9

<210> SEQ ID NO 502
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 502 gctagagaa                                                                9
```

<210> SEQ ID NO 503
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 503 gaaggagaa                                                                  9

<210> SEQ ID NO 504
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 504 agaggagaa                                                                  9

<210> SEQ ID NO 505
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 505 tcaggagaa                                                                  9

<210> SEQ ID NO 506
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 506 ctaggagaa                                                                  9

<210> SEQ ID NO 507
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 507 aacggagaa                                                                  9

<210> SEQ ID NO 508
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 508 ttcggagaa                                                                  9

<210> SEQ ID NO 509
<211> LENGTH: 9
<212> TYPE: DNA
<213> ORGANISM: Artificial Sequence
<220> FEATURE:
<223> OTHER INFORMATION: Barcoding Sequence -continued

<400> SEQUENCE: 509 catggagaa                                                                   9

<210> SEQ ID NO 510
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 510 tgtggagaa                                                                   9

<210> SEQ ID NO 511
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 511 actggagaa                                                                   9

<210> SEQ ID NO 512
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 512 gttggagaa                                                                   9

<210> SEQ ID NO 513
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 513 caacgagaa                                                                   9

<210> SEQ ID NO 514
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 514 tgacgagaa                                                                   9

<210> SEQ ID NO 515
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 515 acacgagaa                                                                   9

<210> SEQ ID NO 516

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 516 gtacgagaa                                                                  9

<210> SEQ ID NO 517
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 517 aagcgagaa                                                                  9

<210> SEQ ID NO 518
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 518 ttgcgagaa                                                                  9

<210> SEQ ID NO 519
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 519 taccgagaa                                                                  9

<210> SEQ ID NO 520
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 520 atccgagaa                                                                  9

<210> SEQ ID NO 521
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 521 gatcgagaa                                                                  9

<210> SEQ ID NO 522
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 522
``` agtcgagaa                                                                        9

<210> SEQ ID NO 523
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 523 cttcgagaa                                                                        9

<210> SEQ ID NO 524
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 524 cgatgagaa                                                                        9

<210> SEQ ID NO 525
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 525 gcatgagaa                                                                        9

<210> SEQ ID NO 526
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 526 cagtgagaa                                                                        9

<210> SEQ ID NO 527
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 527 tggtgagaa                                                                        9

<210> SEQ ID NO 528
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 528 acgtgagaa                                                                        9

<210> SEQ ID NO 529
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 529 gtgtgagaa                                                                9

<210> SEQ ID NO 530
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 530 gactgagaa                                                                9

<210> SEQ ID NO 531
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 531 agctgagaa                                                                9

<210> SEQ ID NO 532
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 532 tcctgagaa                                                                9

<210> SEQ ID NO 533
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 533 ctctgagaa                                                                9

<210> SEQ ID NO 534
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 534 ggttgagaa                                                                9

<210> SEQ ID NO 535
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 535 ccttgagaa                                                                9
```

```
<210> SEQ ID NO 536
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 536 cgaacagaa                                                              9

<210> SEQ ID NO 537
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 537 gcaacagaa                                                              9

<210> SEQ ID NO 538
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 538 cagacagaa                                                              9

<210> SEQ ID NO 539
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 539 tggacagaa                                                              9

<210> SEQ ID NO 540
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 540 acgacagaa                                                              9

<210> SEQ ID NO 541
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 541 gtgacagaa                                                              9

<210> SEQ ID NO 542
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 542 gacacagaa                                                              9

<210> SEQ ID NO 543
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 543 agcacagaa                                                              9

<210> SEQ ID NO 544
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 544 tccacagaa                                                              9

<210> SEQ ID NO 545
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 545 ctcacagaa                                                              9

<210> SEQ ID NO 546
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 546 ggtacagaa                                                              9

<210> SEQ ID NO 547
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 547 cctacagaa                                                              9

<210> SEQ ID NO 548
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 548 caagcagaa                                                              9
```

```
<210> SEQ ID NO 549
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 549 tgagcagaa                                                                 9

<210> SEQ ID NO 550
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 550 acagcagaa                                                                 9

<210> SEQ ID NO 551
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 551 gtagcagaa                                                                 9

<210> SEQ ID NO 552
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 552 aaggcagaa                                                                 9

<210> SEQ ID NO 553
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 553 ttggcagaa                                                                 9

<210> SEQ ID NO 554
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 554 tacgcagaa                                                                 9

<210> SEQ ID NO 555
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 555 atcgcagaa                                                            9

<210> SEQ ID NO 556
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 556 gatgcagaa                                                            9

<210> SEQ ID NO 557
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 557 agtgcagaa                                                            9

<210> SEQ ID NO 558
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 558 cttgcagaa                                                            9

<210> SEQ ID NO 559
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 559 gaaccagaa                                                            9

<210> SEQ ID NO 560
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 560 agaccagaa                                                            9

<210> SEQ ID NO 561
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 561 tcaccagaa                                                            9

<210> SEQ ID NO 562
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 562 ctaccagaa                                                                  9

<210> SEQ ID NO 563
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 563 tagccagaa                                                                  9

<210> SEQ ID NO 564
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 564 atgccagaa                                                                  9

<210> SEQ ID NO 565
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 565 catccagaa                                                                  9

<210> SEQ ID NO 566
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 566 tgtccagaa                                                                  9

<210> SEQ ID NO 567
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 567 actccagaa                                                                  9

<210> SEQ ID NO 568
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 568
``` gttccagaa                                                                              9

<210> SEQ ID NO 569
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 569 ggatcagaa                                                                              9

<210> SEQ ID NO 570
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 570 ccatcagaa                                                                              9

<210> SEQ ID NO 571
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 571 gagtcagaa                                                                              9

<210> SEQ ID NO 572
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 572 aggtcagaa                                                                              9

<210> SEQ ID NO 573
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 573 tcgtcagaa                                                                              9

<210> SEQ ID NO 574
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 574 ctgtcagaa                                                                              9

<210> SEQ ID NO 575
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 575 cactcagaa                                                                9

<210> SEQ ID NO 576
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 576 tgctcagaa                                                                9

<210> SEQ ID NO 577
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 577 acctcagaa                                                                9

<210> SEQ ID NO 578
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 578 gtctcagaa                                                                9

<210> SEQ ID NO 579
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 579 cgttcagaa                                                                9

<210> SEQ ID NO 580
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 580 gcttcagaa                                                                9

<210> SEQ ID NO 581
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 581 cggatagaa                                                                9
```

```
<210> SEQ ID NO 582
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 582 gcgatagaa                                                                  9

<210> SEQ ID NO 583
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 583 ggcatagaa                                                                  9

<210> SEQ ID NO 584
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 584 cgagtagaa                                                                  9

<210> SEQ ID NO 585
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 585 gcagtagaa                                                                  9

<210> SEQ ID NO 586
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 586 caggtagaa                                                                  9

<210> SEQ ID NO 587
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 587 tcggtagaa                                                                  9

<210> SEQ ID NO 588
<211> LENGTH: 9
<212> TYPE: DNA
<213> ORGANISM: Artificial Sequence
<220> FEATURE:
<223> OTHER INFORMATION: Barcoding Sequence
```

-continued

<400> SEQUENCE: 588 gtggtagaa                                                                9

<210> SEQ ID NO 589
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 589 gacgtagaa                                                                9

<210> SEQ ID NO 590
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 590 tgcgtagaa                                                                9

<210> SEQ ID NO 591
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 591 accgtagaa                                                                9

<210> SEQ ID NO 592
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 592 ctcgtagaa                                                                9

<210> SEQ ID NO 593
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 593 ggtgtagaa                                                                9

<210> SEQ ID NO 594
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 594 cctgtagaa                                                                9

<210> SEQ ID NO 595

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 595 ggactagaa                                                                9

<210> SEQ ID NO 596
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 596 ccactagaa                                                                9

<210> SEQ ID NO 597
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 597 gagctagaa                                                                9

<210> SEQ ID NO 598
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 598 tggctagaa                                                                9

<210> SEQ ID NO 599
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 599 acgctagaa                                                                9

<210> SEQ ID NO 600
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 600 ctgctagaa                                                                9

<210> SEQ ID NO 601
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 601
```

```
cacctagaa                                                            9

<210> SEQ ID NO 602
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 602 agcctagaa                                                            9

<210> SEQ ID NO 603
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 603 gtcctagaa                                                            9

<210> SEQ ID NO 604
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 604 cgtctagaa                                                            9

<210> SEQ ID NO 605
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 605 gctctagaa                                                            9

<210> SEQ ID NO 606
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 606 ccgttagaa                                                            9

<210> SEQ ID NO 607
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 607 cgcttagaa                                                            9

<210> SEQ ID NO 608
<211> LENGTH: 9
<212> TYPE: DNA
```

```
<213> ORGANISM: Artificial Sequence
<220> FEATURE:
<223> OTHER INFORMATION: Barcoding Sequence

<400> SEQUENCE: 608 gccttagaa                                                                 9

<210> SEQ ID NO 609
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 609 gagaaggaa                                                                 9

<210> SEQ ID NO 610
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 610 aggaaggaa                                                                 9

<210> SEQ ID NO 611
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 611 tcgaaggaa                                                                 9

<210> SEQ ID NO 612
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 612 ctgaaggaa                                                                 9

<210> SEQ ID NO 613
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 613 cacaaggaa                                                                 9

<210> SEQ ID NO 614
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 614 tgcaaggaa                                                                 9
```

```
<210> SEQ ID NO 615
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 615 accaaggaa                                                                 9

<210> SEQ ID NO 616
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 616 gtcaaggaa                                                                 9

<210> SEQ ID NO 617
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 617 ggtaaggaa                                                                 9

<210> SEQ ID NO 618
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 618 cctaaggaa                                                                 9

<210> SEQ ID NO 619
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 619 gaagaggaa                                                                 9

<210> SEQ ID NO 620
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 620 agagaggaa                                                                 9

<210> SEQ ID NO 621
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 621 tcagaggaa                                                                        9

<210> SEQ ID NO 622
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 622 ctagaggaa                                                                        9

<210> SEQ ID NO 623
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 623 aaggaggaa                                                                        9

<210> SEQ ID NO 624
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 624 ttggaggaa                                                                        9

<210> SEQ ID NO 625
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 625 tacgaggaa                                                                        9

<210> SEQ ID NO 626
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 626 atcgaggaa                                                                        9

<210> SEQ ID NO 627
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 627 catgaggaa                                                                        9
```

```
<210> SEQ ID NO 628
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 628 tgtgaggaa                                                                9

<210> SEQ ID NO 629
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 629 actgaggaa                                                                9

<210> SEQ ID NO 630
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 630 gttgaggaa                                                                9

<210> SEQ ID NO 631
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 631 caacaggaa                                                                9

<210> SEQ ID NO 632
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 632 tgacaggaa                                                                9

<210> SEQ ID NO 633
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 633 acacaggaa                                                                9

<210> SEQ ID NO 634
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 634 gtacaggaa                                                              9

<210> SEQ ID NO 635
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 635 tagcaggaa                                                              9

<210> SEQ ID NO 636
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 636 atgcaggaa                                                              9

<210> SEQ ID NO 637
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 637 aaccaggaa                                                              9

<210> SEQ ID NO 638
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 638 ttccaggaa                                                              9

<210> SEQ ID NO 639
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 639 gatcaggaa                                                              9

<210> SEQ ID NO 640
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 640 agtcaggaa                                                              9

<210> SEQ ID NO 641
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 641 tctcaggaa                                                          9

<210> SEQ ID NO 642
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 642 cttcaggaa                                                          9

<210> SEQ ID NO 643
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 643 ggataggaa                                                          9

<210> SEQ ID NO 644
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 644 ccataggaa                                                          9

<210> SEQ ID NO 645
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 645 cagtaggaa                                                          9

<210> SEQ ID NO 646
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 646 tggtaggaa                                                          9

<210> SEQ ID NO 647
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 647
```

-continued acgtaggaa                                                           9

<210> SEQ ID NO 648
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 648 gtgtaggaa                                                           9

<210> SEQ ID NO 649
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 649 gactaggaa                                                           9

<210> SEQ ID NO 650
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 650 agctaggaa                                                           9

<210> SEQ ID NO 651
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 651 ctctaggaa                                                           9

<210> SEQ ID NO 652
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 652 cgttaggaa                                                           9

<210> SEQ ID NO 653
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 653 gcttaggaa                                                           9

<210> SEQ ID NO 654
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 654 agaacggaa                                                                 9

<210> SEQ ID NO 655
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 655 tcaacggaa                                                                 9

<210> SEQ ID NO 656
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 656 gtaacggaa                                                                 9

<210> SEQ ID NO 657
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 657 aagacggaa                                                                 9

<210> SEQ ID NO 658
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 658 ttgacggaa                                                                 9

<210> SEQ ID NO 659
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 659 tacacggaa                                                                 9

<210> SEQ ID NO 660
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 660 atcacggaa                                                                 9
```

```
<210> SEQ ID NO 661
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 661 gatacggaa                                                                 9

<210> SEQ ID NO 662
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 662 tgtacggaa                                                                 9

<210> SEQ ID NO 663
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 663 actacggaa                                                                 9

<210> SEQ ID NO 664
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 664 cttacggaa                                                                 9

<210> SEQ ID NO 665
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 665 taagcggaa                                                                 9

<210> SEQ ID NO 666
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 666 atagcggaa                                                                 9

<210> SEQ ID NO 667
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 667 aatgcggaa                                                                    9

<210> SEQ ID NO 668
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 668 ttaccggaa                                                                    9

<210> SEQ ID NO 669
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 669 tatccggaa                                                                    9

<210> SEQ ID NO 670
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 670 attccggaa                                                                    9

<210> SEQ ID NO 671
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 671 gaatcggaa                                                                    9

<210> SEQ ID NO 672
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 672 tgatcggaa                                                                    9

<210> SEQ ID NO 673
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 673 acatcggaa                                                                    9

<210> SEQ ID NO 674
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 674 ctatcggaa                                                                 9

<210> SEQ ID NO 675
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 675 tagtcggaa                                                                 9

<210> SEQ ID NO 676
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 676 atgtcggaa                                                                 9

<210> SEQ ID NO 677
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 677 aactcggaa                                                                 9

<210> SEQ ID NO 678
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 678 ttctcggaa                                                                 9

<210> SEQ ID NO 679
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 679 cattcggaa                                                                 9

<210> SEQ ID NO 680
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 680
``` agttcggaa 9

<210> SEQ ID NO 681
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 681 tcttcggaa 9

<210> SEQ ID NO 682
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 682 ggaatggaa 9

<210> SEQ ID NO 683
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 683 ccaatggaa 9

<210> SEQ ID NO 684
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 684 cagatggaa 9

<210> SEQ ID NO 685
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 685 tggatggaa 9

<210> SEQ ID NO 686
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 686 acgatggaa 9

<210> SEQ ID NO 687
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 687 gtgatggaa                                                              9

<210> SEQ ID NO 688
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 688 gacatggaa                                                              9

<210> SEQ ID NO 689
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 689 agcatggaa                                                              9

<210> SEQ ID NO 690
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 690 ctcatggaa                                                              9

<210> SEQ ID NO 691
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 691 cgtatggaa                                                              9

<210> SEQ ID NO 692
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 692 gctatggaa                                                              9

<210> SEQ ID NO 693
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 693 caagtggaa                                                              9
```

```
<210> SEQ ID NO 694
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 694 tgagtggaa                                                                 9

<210> SEQ ID NO 695
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 695 acagtggaa                                                                 9

<210> SEQ ID NO 696
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 696 gtagtggaa                                                                 9

<210> SEQ ID NO 697
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 697 taggtggaa                                                                 9

<210> SEQ ID NO 698
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 698 atggtggaa                                                                 9

<210> SEQ ID NO 699
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 699 aacgtggaa                                                                 9

<210> SEQ ID NO 700
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 700 ttcgtggaa                                                                                       9

<210> SEQ ID NO 701
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 701 gatgtggaa                                                                                       9

<210> SEQ ID NO 702
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 702 agtgtggaa                                                                                       9

<210> SEQ ID NO 703
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 703 tctgtggaa                                                                                       9

<210> SEQ ID NO 704
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 704 cttgtggaa                                                                                       9

<210> SEQ ID NO 705
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 705 gaactggaa                                                                                       9

<210> SEQ ID NO 706
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 706 agactggaa                                                                                       9
```

```
<210> SEQ ID NO 707
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 707 tcactggaa                                                                  9

<210> SEQ ID NO 708
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 708 ctactggaa                                                                  9

<210> SEQ ID NO 709
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 709 aagctggaa                                                                  9

<210> SEQ ID NO 710
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 710 ttgctggaa                                                                  9

<210> SEQ ID NO 711
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 711 tacctggaa                                                                  9

<210> SEQ ID NO 712
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 712 atcctggaa                                                                  9

<210> SEQ ID NO 713
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 713 catctggaa                                                             9

<210> SEQ ID NO 714
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 714 tgtctggaa                                                             9

<210> SEQ ID NO 715
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 715 actctggaa                                                             9

<210> SEQ ID NO 716
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 716 gttctggaa                                                             9

<210> SEQ ID NO 717
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 717 cgattggaa                                                             9

<210> SEQ ID NO 718
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 718 gcattggaa                                                             9

<210> SEQ ID NO 719
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 719 gagttggaa                                                             9

<210> SEQ ID NO 720
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 720 aggttggaa                                                                9

<210> SEQ ID NO 721
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 721 tcgttggaa                                                                9

<210> SEQ ID NO 722
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 722 ctgttggaa                                                                9

<210> SEQ ID NO 723
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 723 cacttggaa                                                                9

<210> SEQ ID NO 724
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 724 tgcttggaa                                                                9

<210> SEQ ID NO 725
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 725 accttggaa                                                                9

<210> SEQ ID NO 726
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 726
```

```
gtcttggaa                                                           9
```

<210> SEQ ID NO 727
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 727

```
cagaacgaa                                                           9
```

<210> SEQ ID NO 728
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 728

```
tggaacgaa                                                           9
```

<210> SEQ ID NO 729
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 729

```
acgaacgaa                                                           9
```

<210> SEQ ID NO 730
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 730

```
gtgaacgaa                                                           9
```

<210> SEQ ID NO 731
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 731

```
gacaacgaa                                                           9
```

<210> SEQ ID NO 732
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 732

```
agcaacgaa                                                           9
```

<210> SEQ ID NO 733
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 733 tccaacgaa                                                                    9

<210> SEQ ID NO 734
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 734 ctcaacgaa                                                                    9

<210> SEQ ID NO 735
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 735 cgtaacgaa                                                                    9

<210> SEQ ID NO 736
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 736 gctaacgaa                                                                    9

<210> SEQ ID NO 737
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 737 caagacgaa                                                                    9

<210> SEQ ID NO 738
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 738 tgagacgaa                                                                    9

<210> SEQ ID NO 739
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 739 acagacgaa                                                                    9
```

```
<210> SEQ ID NO 740
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 740 gtagacgaa                                                                 9

<210> SEQ ID NO 741
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 741 taggacgaa                                                                 9

<210> SEQ ID NO 742
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 742 atggacgaa                                                                 9

<210> SEQ ID NO 743
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 743 aacgacgaa                                                                 9

<210> SEQ ID NO 744
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 744 ttcgacgaa                                                                 9

<210> SEQ ID NO 745
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 745 gatgacgaa                                                                 9

<210> SEQ ID NO 746
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 746 agtgacgaa                                                              9

<210> SEQ ID NO 747
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 747 tctgacgaa                                                              9

<210> SEQ ID NO 748
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 748 cttgacgaa                                                              9

<210> SEQ ID NO 749
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 749 gaacacgaa                                                              9

<210> SEQ ID NO 750
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 750 agacacgaa                                                              9

<210> SEQ ID NO 751
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 751 tcacacgaa                                                              9

<210> SEQ ID NO 752
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 752 ctacacgaa                                                              9

<210> SEQ ID NO 753
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 753 aagcacgaa                                                                  9

<210> SEQ ID NO 754
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 754 ttgcacgaa                                                                  9

<210> SEQ ID NO 755
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 755 taccacgaa                                                                  9

<210> SEQ ID NO 756
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 756 atccacgaa                                                                  9

<210> SEQ ID NO 757
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 757 catcacgaa                                                                  9

<210> SEQ ID NO 758
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 758 tgtcacgaa                                                                  9

<210> SEQ ID NO 759
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 759
``` actcacgaa                                                                    9

<210> SEQ ID NO 760
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 760 gttcacgaa                                                                    9

<210> SEQ ID NO 761
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 761 cgatacgaa                                                                    9

<210> SEQ ID NO 762
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 762 gcatacgaa                                                                    9

<210> SEQ ID NO 763
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 763 gagtacgaa                                                                    9

<210> SEQ ID NO 764
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 764 aggtacgaa                                                                    9

<210> SEQ ID NO 765
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 765 ctgtacgaa                                                                    9

<210> SEQ ID NO 766
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 766 cactacgaa                                                                  9

<210> SEQ ID NO 767
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 767 tgctacgaa                                                                  9

<210> SEQ ID NO 768
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 768 acctacgaa                                                                  9

<210> SEQ ID NO 769
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 769 gtctacgaa                                                                  9

<210> SEQ ID NO 770
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 770 ggttacgaa                                                                  9

<210> SEQ ID NO 771
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 771 ccttacgaa                                                                  9

<210> SEQ ID NO 772
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 772 agaagcgaa                                                                  9
```

<210> SEQ ID NO 773
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 773 tcaagcgaa                                                                  9

<210> SEQ ID NO 774
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 774 gtaagcgaa                                                                  9

<210> SEQ ID NO 775
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 775 aagagcgaa                                                                  9

<210> SEQ ID NO 776
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 776 ttgagcgaa                                                                  9

<210> SEQ ID NO 777
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 777 tacagcgaa                                                                  9

<210> SEQ ID NO 778
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 778 atcagcgaa                                                                  9

<210> SEQ ID NO 779
<211> LENGTH: 9
<212> TYPE: DNA
<213> ORGANISM: Artificial Sequence
<220> FEATURE:

<223> OTHER INFORMATION: Barcoding Sequence

<400> SEQUENCE: 779 gatagcgaa                                                                                9

<210> SEQ ID NO 780
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 780 tgtagcgaa                                                                                9

<210> SEQ ID NO 781
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 781 actagcgaa                                                                                9

<210> SEQ ID NO 782
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 782 cttagcgaa                                                                                9

<210> SEQ ID NO 783
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 783 taaggcgaa                                                                                9

<210> SEQ ID NO 784
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 784 ataggcgaa                                                                                9

<210> SEQ ID NO 785
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 785 aatggcgaa                                                                                9

-continued

<210> SEQ ID NO 786
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 786 ttacgcgaa                                                                9

<210> SEQ ID NO 787
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 787 tatcgcgaa                                                                9

<210> SEQ ID NO 788
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 788 attcgcgaa                                                                9

<210> SEQ ID NO 789
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 789 gaatgcgaa                                                                9

<210> SEQ ID NO 790
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 790 tgatgcgaa                                                                9

<210> SEQ ID NO 791
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 791 acatgcgaa                                                                9

<210> SEQ ID NO 792
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 792 ctatgcgaa                                                                                          9

<210> SEQ ID NO 793
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 793 tagtgcgaa                                                                                          9

<210> SEQ ID NO 794
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 794 atgtgcgaa                                                                                          9

<210> SEQ ID NO 795
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 795 aactgcgaa                                                                                          9

<210> SEQ ID NO 796
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 796 ttctgcgaa                                                                                          9

<210> SEQ ID NO 797
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 797 cattgcgaa                                                                                          9

<210> SEQ ID NO 798
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 798 agttgcgaa                                                                                          9

<210> SEQ ID NO 799
<211> LENGTH: 9

```
<212> TYPE: DNA
<213> ORGANISM: Artificial Sequence
<220> FEATURE:
<223> OTHER INFORMATION: Barcoding Sequence

<400> SEQUENCE: 799 tcttgcgaa                                                                  9

<210> SEQ ID NO 800
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 800 tgaaccgaa                                                                  9

<210> SEQ ID NO 801
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 801 acaaccgaa                                                                  9

<210> SEQ ID NO 802
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 802 ctaaccgaa                                                                  9

<210> SEQ ID NO 803
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 803 tagaccgaa                                                                  9

<210> SEQ ID NO 804
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 804 atgaccgaa                                                                  9

<210> SEQ ID NO 805
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 805
``` aacaccgaa                                                                    9

<210> SEQ ID NO 806
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 806 ttcaccgaa                                                                    9

<210> SEQ ID NO 807
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 807 cataccgaa                                                                    9

<210> SEQ ID NO 808
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 808 agtaccgaa                                                                    9

<210> SEQ ID NO 809
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 809 tctaccgaa                                                                    9

<210> SEQ ID NO 810
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 810 gttaccgaa                                                                    9

<210> SEQ ID NO 811
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 811 ttagccgaa                                                                    9

<210> SEQ ID NO 812
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 812 tatgccgaa                                                                                      9

<210> SEQ ID NO 813
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 813 attgccgaa                                                                                      9

<210> SEQ ID NO 814
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 814 caatccgaa                                                                                      9

<210> SEQ ID NO 815
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 815 agatccgaa                                                                                      9

<210> SEQ ID NO 816
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 816 tcatccgaa                                                                                      9

<210> SEQ ID NO 817
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 817 gtatccgaa                                                                                      9

<210> SEQ ID NO 818
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 818 aagtccgaa                                                                                      9

```
<210> SEQ ID NO 819
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 819 ttgtccgaa                                                                  9

<210> SEQ ID NO 820
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 820 tactccgaa                                                                  9

<210> SEQ ID NO 821
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 821 atctccgaa                                                                  9

<210> SEQ ID NO 822
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 822 gattccgaa                                                                  9

<210> SEQ ID NO 823
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 823 tgttccgaa                                                                  9

<210> SEQ ID NO 824
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 824 acttccgaa                                                                  9

<210> SEQ ID NO 825
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 825 cgaatcgaa                                                              9

<210> SEQ ID NO 826
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 826 gcaatcgaa                                                              9

<210> SEQ ID NO 827
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 827 gagatcgaa                                                              9

<210> SEQ ID NO 828
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 828 aggatcgaa                                                              9

<210> SEQ ID NO 829
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 829 ctgatcgaa                                                              9

<210> SEQ ID NO 830
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 830 cacatcgaa                                                              9

<210> SEQ ID NO 831
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 831 tgcatcgaa                                                              9

<210> SEQ ID NO 832
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 832 accatcgaa                                                                  9

<210> SEQ ID NO 833
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 833 gtcatcgaa                                                                  9

<210> SEQ ID NO 834
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 834 ggtatcgaa                                                                  9

<210> SEQ ID NO 835
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 835 cctatcgaa                                                                  9

<210> SEQ ID NO 836
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 836 gaagtcgaa                                                                  9

<210> SEQ ID NO 837
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 837 agagtcgaa                                                                  9

<210> SEQ ID NO 838
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 838
``` tcagtcgaa                                                                    9

<210> SEQ ID NO 839
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 839 ctagtcgaa                                                                    9

<210> SEQ ID NO 840
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 840 aaggtcgaa                                                                    9

<210> SEQ ID NO 841
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 841 ttggtcgaa                                                                    9

<210> SEQ ID NO 842
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 842 tacgtcgaa                                                                    9

<210> SEQ ID NO 843
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 843 atcgtcgaa                                                                    9

<210> SEQ ID NO 844
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 844 catgtcgaa                                                                    9

<210> SEQ ID NO 845
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 845 tgtgtcgaa                                                                9

<210> SEQ ID NO 846
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 846 actgtcgaa                                                                9

<210> SEQ ID NO 847
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 847 gttgtcgaa                                                                9

<210> SEQ ID NO 848
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 848 caactcgaa                                                                9

<210> SEQ ID NO 849
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 849 tgactcgaa                                                                9

<210> SEQ ID NO 850
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 850 acactcgaa                                                                9

<210> SEQ ID NO 851
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 851 gtactcgaa                                                                9
```

<210> SEQ ID NO 852
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 852 cggaagaac                                                                 9

<210> SEQ ID NO 853
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 853 gcgaagaac                                                                 9

<210> SEQ ID NO 854
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 854 ggcaagaac                                                                 9

<210> SEQ ID NO 855
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 855 ggagagaac                                                                 9

<210> SEQ ID NO 856
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 856 ccagagaac                                                                 9

<210> SEQ ID NO 857
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 857 gaggagaac                                                                 9

<210> SEQ ID NO 858
<211> LENGTH: 9
<212> TYPE: DNA
<213> ORGANISM: Artificial Sequence
<220> FEATURE:

<223> OTHER INFORMATION: Barcoding Sequence

<400> SEQUENCE: 858 acggagaac                                                                                      9

<210> SEQ ID NO 859
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 859 ctggagaac                                                                                      9

<210> SEQ ID NO 860
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 860 cacgagaac                                                                                      9

<210> SEQ ID NO 861
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 861 agcgagaac                                                                                      9

<210> SEQ ID NO 862
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 862 tccgagaac                                                                                      9

<210> SEQ ID NO 863
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 863 gtcgagaac                                                                                      9

<210> SEQ ID NO 864
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 864 cgtgagaac                                                                                      9

```
<210> SEQ ID NO 865
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 865 gctgagaac                                                                 9

<210> SEQ ID NO 866
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 866 cgacagaac                                                                 9

<210> SEQ ID NO 867
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 867 gcacagaac                                                                 9

<210> SEQ ID NO 868
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 868 cagcagaac                                                                 9

<210> SEQ ID NO 869
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 869 aggcagaac                                                                 9

<210> SEQ ID NO 870
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 870 tcgcagaac                                                                 9

<210> SEQ ID NO 871
<211> LENGTH: 9
<212> TYPE: DNA
<213> ORGANISM: Artificial Sequence
<220> FEATURE:
<223> OTHER INFORMATION: Barcoding Sequence
```

<400> SEQUENCE: 871 gtgcagaac  9

<210> SEQ ID NO 872
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 872 gaccagaac  9

<210> SEQ ID NO 873
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 873 tgccagaac  9

<210> SEQ ID NO 874
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 874 ctccagaac  9

<210> SEQ ID NO 875
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 875 ggtcagaac  9

<210> SEQ ID NO 876
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 876 cctcagaac  9

<210> SEQ ID NO 877
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 877 ccgtagaac  9

<210> SEQ ID NO 878
<211> LENGTH: 9

```
<212> TYPE: DNA
<213> ORGANISM: Artificial Sequence
<220> FEATURE:
<223> OTHER INFORMATION: Barcoding Sequence

<400> SEQUENCE: 878 cgctagaac                                                                9

<210> SEQ ID NO 879
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 879 gcctagaac                                                                9

<210> SEQ ID NO 880
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 880 ggaaggaac                                                                9

<210> SEQ ID NO 881
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 881 ccaaggaac                                                                9

<210> SEQ ID NO 882
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 882 gagaggaac                                                                9

<210> SEQ ID NO 883
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 883 aggaggaac                                                                9

<210> SEQ ID NO 884
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 884
``` tcgaggaac 9

<210> SEQ ID NO 885
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 885 ctgaggaac 9

<210> SEQ ID NO 886
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 886 cacaggaac 9

<210> SEQ ID NO 887
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 887 tgcaggaac 9

<210> SEQ ID NO 888
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 888 accaggaac 9

<210> SEQ ID NO 889
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 889 gtcaggaac 9

<210> SEQ ID NO 890
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 890 cgtaggaac 9

<210> SEQ ID NO 891
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 891 gctaggaac                                                                    9

<210> SEQ ID NO 892
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 892 gaacggaac                                                                    9

<210> SEQ ID NO 893
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 893 agacggaac                                                                    9

<210> SEQ ID NO 894
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 894 tcacggaac                                                                    9

<210> SEQ ID NO 895
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 895 ctacggaac                                                                    9

<210> SEQ ID NO 896
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 896 aagcggaac                                                                    9

<210> SEQ ID NO 897
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 897 ttgcggaac                                                                    9

```
<210> SEQ ID NO 898
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 898 taccggaac                                                            9

<210> SEQ ID NO 899
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 899 atccggaac                                                            9

<210> SEQ ID NO 900
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 900 catcggaac                                                            9

<210> SEQ ID NO 901
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 901 tgtcggaac                                                            9

<210> SEQ ID NO 902
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 902 actcggaac                                                            9

<210> SEQ ID NO 903
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 903 gttcggaac                                                            9

<210> SEQ ID NO 904
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 904 cgatggaac                                                              9

<210> SEQ ID NO 905
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 905 gcatggaac                                                              9

<210> SEQ ID NO 906
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 906 cagtggaac                                                              9

<210> SEQ ID NO 907
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 907 tggtggaac                                                              9

<210> SEQ ID NO 908
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 908 acgtggaac                                                              9

<210> SEQ ID NO 909
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 909 gtgtggaac                                                              9

<210> SEQ ID NO 910
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 910 gactggaac                                                              9

<210> SEQ ID NO 911
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 911 agctggaac                                                                9

<210> SEQ ID NO 912
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 912 tcctggaac                                                                9

<210> SEQ ID NO 913
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 913 ctctggaac                                                                9

<210> SEQ ID NO 914
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 914 ggttggaac                                                                9

<210> SEQ ID NO 915
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 915 ccttggaac                                                                9

<210> SEQ ID NO 916
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 916 cgaacgaac                                                                9

<210> SEQ ID NO 917
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 917
``` gcaacgaac				9

<210> SEQ ID NO 918
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 918 cagacgaac				9

<210> SEQ ID NO 919
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 919 tggacgaac				9

<210> SEQ ID NO 920
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 920 acgacgaac				9

<210> SEQ ID NO 921
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 921 gtgacgaac				9

<210> SEQ ID NO 922
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 922 gacacgaac				9

<210> SEQ ID NO 923
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 923 agcacgaac				9

<210> SEQ ID NO 924
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 924 tccacgaac                                                                9

<210> SEQ ID NO 925
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 925 ctcacgaac                                                                9

<210> SEQ ID NO 926
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 926 ggtacgaac                                                                9

<210> SEQ ID NO 927
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 927 cctacgaac                                                                9

<210> SEQ ID NO 928
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 928 gaagcgaac                                                                9

<210> SEQ ID NO 929
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 929 agagcgaac                                                                9

<210> SEQ ID NO 930
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 930 tcagcgaac                                                                9
```

```
<210> SEQ ID NO 931
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 931 ctagcgaac                                                          9

<210> SEQ ID NO 932
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 932 aaggcgaac                                                          9

<210> SEQ ID NO 933
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 933 ttggcgaac                                                          9

<210> SEQ ID NO 934
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 934 tacgcgaac                                                          9

<210> SEQ ID NO 935
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 935 atcgcgaac                                                          9

<210> SEQ ID NO 936
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 936 catgcgaac                                                          9

<210> SEQ ID NO 937
<211> LENGTH: 9
<212> TYPE: DNA
<213> ORGANISM: Artificial Sequence
<220> FEATURE:
```

<223> OTHER INFORMATION: Barcoding Sequence

<400> SEQUENCE: 937 tgtgcgaac                                                                      9

<210> SEQ ID NO 938
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 938 actgcgaac                                                                      9

<210> SEQ ID NO 939
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 939 gttgcgaac                                                                      9

<210> SEQ ID NO 940
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 940 caaccgaac                                                                      9

<210> SEQ ID NO 941
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 941 tgaccgaac                                                                      9

<210> SEQ ID NO 942
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 942 acaccgaac                                                                      9

<210> SEQ ID NO 943
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 943 gtaccgaac                                                                      9

```
<210> SEQ ID NO 944
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 944 tagccgaac                                                                  9

<210> SEQ ID NO 945
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 945 atgccgaac                                                                  9

<210> SEQ ID NO 946
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 946 gatccgaac                                                                  9

<210> SEQ ID NO 947
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 947 agtccgaac                                                                  9

<210> SEQ ID NO 948
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 948 tctccgaac                                                                  9

<210> SEQ ID NO 949
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 949 cttccgaac                                                                  9

<210> SEQ ID NO 950
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 950 ggatcgaac                                                              9

<210> SEQ ID NO 951
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 951 ccatcgaac                                                              9

<210> SEQ ID NO 952
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 952 gagtcgaac                                                              9

<210> SEQ ID NO 953
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 953 aggtcgaac                                                              9

<210> SEQ ID NO 954
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 954 tcgtcgaac                                                              9

<210> SEQ ID NO 955
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 955 ctgtcgaac                                                              9

<210> SEQ ID NO 956
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 956 cactcgaac                                                              9

<210> SEQ ID NO 957
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 957 tgctcgaac                                                                    9

<210> SEQ ID NO 958
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 958 acctcgaac                                                                    9

<210> SEQ ID NO 959
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 959 gtctcgaac                                                                    9

<210> SEQ ID NO 960
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 960 cgttcgaac                                                                    9

<210> SEQ ID NO 961
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 961 gcttcgaac                                                                    9

<210> SEQ ID NO 962
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 962 ccgatgaac                                                                    9

<210> SEQ ID NO 963
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 963
``` cgcatgaac                                                                  9

<210> SEQ ID NO 964
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 964 gccatgaac                                                                  9

<210> SEQ ID NO 965
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 965 cgagtgaac                                                                  9

<210> SEQ ID NO 966
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 966 gcagtgaac                                                                  9

<210> SEQ ID NO 967
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 967 caggtgaac                                                                  9

<210> SEQ ID NO 968
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 968 tcggtgaac                                                                  9

<210> SEQ ID NO 969
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 969 gtggtgaac                                                                  9

<210> SEQ ID NO 970
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 970 gacgtgaac                                                                    9

<210> SEQ ID NO 971
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 971 tgcgtgaac                                                                    9

<210> SEQ ID NO 972
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 972 accgtgaac                                                                    9

<210> SEQ ID NO 973
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 973 ctcgtgaac                                                                    9

<210> SEQ ID NO 974
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 974 ggtgtgaac                                                                    9

<210> SEQ ID NO 975
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 975 cctgtgaac                                                                    9

<210> SEQ ID NO 976
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 976 ggactgaac                                                                    9
```

<210> SEQ ID NO 977
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 977 ccactgaac                                                               9

<210> SEQ ID NO 978
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 978 gagctgaac                                                               9

<210> SEQ ID NO 979
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 979 tggctgaac                                                               9

<210> SEQ ID NO 980
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 980 acgctgaac                                                               9

<210> SEQ ID NO 981
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 981 ctgctgaac                                                               9

<210> SEQ ID NO 982
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 982 cacctgaac                                                               9

<210> SEQ ID NO 983
<211> LENGTH: 9
<212> TYPE: DNA
<213> ORGANISM: Artificial Sequence
<220> FEATURE:
<223> OTHER INFORMATION: Barcoding Sequence

```
<400> SEQUENCE: 983 agcctgaac                                                                9

<210> SEQ ID NO 984
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 984 gtcctgaac                                                                9

<210> SEQ ID NO 985
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 985 cgtctgaac                                                                9

<210> SEQ ID NO 986
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 986 gctctgaac                                                                9

<210> SEQ ID NO 987
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 987 cggttgaac                                                                9

<210> SEQ ID NO 988
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 988 gcgttgaac                                                                9

<210> SEQ ID NO 989
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 989 ggcttgaac                                                                9

<210> SEQ ID NO 990
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 990 ccgaacaac                                                                 9

<210> SEQ ID NO 991
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 991 cgcaacaac                                                                 9

<210> SEQ ID NO 992
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 992 gccaacaac                                                                 9

<210> SEQ ID NO 993
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 993 cgagacaac                                                                 9

<210> SEQ ID NO 994
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 994 gcagacaac                                                                 9

<210> SEQ ID NO 995
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 995 caggacaac                                                                 9

<210> SEQ ID NO 996
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 996
``` tcggacaac 9

<210> SEQ ID NO 997
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 997 gtggacaac 9

<210> SEQ ID NO 998
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 998 gacgacaac 9

<210> SEQ ID NO 999
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 999 tgcgacaac 9

<210> SEQ ID NO 1000
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1000 accgacaac 9

<210> SEQ ID NO 1001
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1001 ctcgacaac 9

<210> SEQ ID NO 1002
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1002 ggtgacaac 9

<210> SEQ ID NO 1003
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 1003 cctgacaac                                                                  9

<210> SEQ ID NO 1004
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1004 ggacacaac                                                                  9

<210> SEQ ID NO 1005
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1005 ccacacaac                                                                  9

<210> SEQ ID NO 1006
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1006 gagcacaac                                                                  9

<210> SEQ ID NO 1007
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1007 tggcacaac                                                                  9

<210> SEQ ID NO 1008
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1008 acgcacaac                                                                  9

<210> SEQ ID NO 1009
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1009 ctgcacaac                                                                  9
```

```
<210> SEQ ID NO 1010
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1010 caccacaac                                                                9

<210> SEQ ID NO 1011
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1011 agccacaac                                                                9

<210> SEQ ID NO 1012
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1012 gtccacaac                                                                9

<210> SEQ ID NO 1013
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1013 cgtcacaac                                                                9

<210> SEQ ID NO 1014
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1014 gctcacaac                                                                9

<210> SEQ ID NO 1015
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1015 cggtacaac                                                                9

<210> SEQ ID NO 1016
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 1016 gcgtacaac                                                                 9

<210> SEQ ID NO 1017
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1017 ggctacaac                                                                 9

<210> SEQ ID NO 1018
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1018 cgaagcaac                                                                 9

<210> SEQ ID NO 1019
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1019 gcaagcaac                                                                 9

<210> SEQ ID NO 1020
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1020 cagagcaac                                                                 9

<210> SEQ ID NO 1021
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1021 tggagcaac                                                                 9

<210> SEQ ID NO 1022
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1022 acgagcaac                                                                 9
```

```
<210> SEQ ID NO 1023
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1023 gtgagcaac                                                                  9

<210> SEQ ID NO 1024
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1024 gacagcaac                                                                  9

<210> SEQ ID NO 1025
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1025 agcagcaac                                                                  9

<210> SEQ ID NO 1026
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1026 tccagcaac                                                                  9

<210> SEQ ID NO 1027
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1027 ctcagcaac                                                                  9

<210> SEQ ID NO 1028
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1028 ggtagcaac                                                                  9

<210> SEQ ID NO 1029
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 1029 cctagcaac                                                              9

<210> SEQ ID NO 1030
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1030 gaaggcaac                                                              9

<210> SEQ ID NO 1031
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1031 agaggcaac                                                              9

<210> SEQ ID NO 1032
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1032 tcaggcaac                                                              9

<210> SEQ ID NO 1033
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1033 ctaggcaac                                                              9

<210> SEQ ID NO 1034
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1034 aacggcaac                                                              9

<210> SEQ ID NO 1035
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1035 ttcggcaac                                                              9

<210> SEQ ID NO 1036
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 1036 catggcaac                                                              9

<210> SEQ ID NO 1037
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1037 tgtggcaac                                                              9

<210> SEQ ID NO 1038
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1038 actggcaac                                                              9

<210> SEQ ID NO 1039
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1039 gttggcaac                                                              9

<210> SEQ ID NO 1040
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1040 caacgcaac                                                              9

<210> SEQ ID NO 1041
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1041 tgacgcaac                                                              9

<210> SEQ ID NO 1042
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1042
``` acacgcaac 9

<210> SEQ ID NO 1043
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1043 gtacgcaac 9

<210> SEQ ID NO 1044
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1044 tagcgcaac 9

<210> SEQ ID NO 1045
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1045 atgcgcaac 9

<210> SEQ ID NO 1046
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1046 gatcgcaac 9

<210> SEQ ID NO 1047
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1047 agtcgcaac 9

<210> SEQ ID NO 1048
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1048 tctcgcaac 9

<210> SEQ ID NO 1049
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 1049 cttcgcaac                                                                    9

<210> SEQ ID NO 1050
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1050 ggatgcaac                                                                    9

<210> SEQ ID NO 1051
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1051 ccatgcaac                                                                    9

<210> SEQ ID NO 1052
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1052 gagtgcaac                                                                    9

<210> SEQ ID NO 1053
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1053 aggtgcaac                                                                    9

<210> SEQ ID NO 1054
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1054 tcgtgcaac                                                                    9

<210> SEQ ID NO 1055
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1055 ctgtgcaac                                                                    9
```

```
<210> SEQ ID NO 1056
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1056 cactgcaac                                                                  9

<210> SEQ ID NO 1057
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1057 tgctgcaac                                                                  9

<210> SEQ ID NO 1058
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1058 acctgcaac                                                                  9

<210> SEQ ID NO 1059
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1059 gtctgcaac                                                                  9

<210> SEQ ID NO 1060
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1060 cgttgcaac                                                                  9

<210> SEQ ID NO 1061
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1061 gcttgcaac                                                                  9

<210> SEQ ID NO 1062
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 1062 ggaaccaac                                                            9

<210> SEQ ID NO 1063
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1063 ccaaccaac                                                            9

<210> SEQ ID NO 1064
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1064 gagaccaac                                                            9

<210> SEQ ID NO 1065
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1065 aggaccaac                                                            9

<210> SEQ ID NO 1066
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1066 tcgaccaac                                                            9

<210> SEQ ID NO 1067
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1067 ctgaccaac                                                            9

<210> SEQ ID NO 1068
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1068 cacaccaac                                                            9

<210> SEQ ID NO 1069
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1069 tgcaccaac                                                                 9

<210> SEQ ID NO 1070
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1070 accaccaac                                                                 9

<210> SEQ ID NO 1071
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1071 gtcaccaac                                                                 9

<210> SEQ ID NO 1072
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1072 cgtaccaac                                                                 9

<210> SEQ ID NO 1073
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1073 gctaccaac                                                                 9

<210> SEQ ID NO 1074
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1074 caagccaac                                                                 9

<210> SEQ ID NO 1075
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1075
``` tgagccaac                                                                      9

<210> SEQ ID NO 1076
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1076 acagccaac                                                                      9

<210> SEQ ID NO 1077
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1077 gtagccaac                                                                      9

<210> SEQ ID NO 1078
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1078 taggccaac                                                                      9

<210> SEQ ID NO 1079
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1079 atggccaac                                                                      9

<210> SEQ ID NO 1080
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1080 gatgccaac                                                                      9

<210> SEQ ID NO 1081
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1081 agtgccaac                                                                      9

<210> SEQ ID NO 1082
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 1082 tctgccaac                                                            9

<210> SEQ ID NO 1083
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1083 cttgccaac                                                            9

<210> SEQ ID NO 1084
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1084 cgatccaac                                                            9

<210> SEQ ID NO 1085
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1085 gcatccaac                                                            9

<210> SEQ ID NO 1086
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1086 cagtccaac                                                            9

<210> SEQ ID NO 1087
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1087 tggtccaac                                                            9

<210> SEQ ID NO 1088
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1088 acgtccaac                                                            9
```

```
<210> SEQ ID NO 1089
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1089 gtgtccaac                                                                 9

<210> SEQ ID NO 1090
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1090 gactccaac                                                                 9

<210> SEQ ID NO 1091
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1091 agctccaac                                                                 9

<210> SEQ ID NO 1092
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1092 tcctccaac                                                                 9

<210> SEQ ID NO 1093
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1093 ctctccaac                                                                 9

<210> SEQ ID NO 1094
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1094 ggttccaac                                                                 9

<210> SEQ ID NO 1095
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 1095 ccttccaac                                                              9

<210> SEQ ID NO 1096
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1096 cggatcaac                                                              9

<210> SEQ ID NO 1097
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1097 gcgatcaac                                                              9

<210> SEQ ID NO 1098
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1098 ggcatcaac                                                              9

<210> SEQ ID NO 1099
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1099 ggagtcaac                                                              9

<210> SEQ ID NO 1100
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1100 ccagtcaac                                                              9

<210> SEQ ID NO 1101
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1101 gaggtcaac                                                              9
```

<210> SEQ ID NO 1102
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1102 acggtcaac                                                                 9

<210> SEQ ID NO 1103
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1103 ctggtcaac                                                                 9

<210> SEQ ID NO 1104
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1104 cacgtcaac                                                                 9

<210> SEQ ID NO 1105
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1105 agcgtcaac                                                                 9

<210> SEQ ID NO 1106
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1106 tccgtcaac                                                                 9

<210> SEQ ID NO 1107
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1107 gtcgtcaac                                                                 9

<210> SEQ ID NO 1108
<211> LENGTH: 9
<212> TYPE: DNA
<213> ORGANISM: Artificial Sequence
<220> FEATURE:
<223> OTHER INFORMATION: Barcoding Sequence

```
<400> SEQUENCE: 1108 cgtgtcaac                                                                        9

<210> SEQ ID NO 1109
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1109 gctgtcaac                                                                        9

<210> SEQ ID NO 1110
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1110 cgactcaac                                                                        9

<210> SEQ ID NO 1111
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1111 gcactcaac                                                                        9

<210> SEQ ID NO 1112
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1112 cagctcaac                                                                        9

<210> SEQ ID NO 1113
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1113 aggctcaac                                                                        9

<210> SEQ ID NO 1114
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1114 tcgctcaac                                                                        9

<210> SEQ ID NO 1115
<211> LENGTH: 9
```

```
<212> TYPE: DNA
<213> ORGANISM: Artificial Sequence
<220> FEATURE:
<223> OTHER INFORMATION: Barcoding Sequence

<400> SEQUENCE: 1115 gtgctcaac                                                                9

<210> SEQ ID NO 1116
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1116 gacctcaac                                                                9

<210> SEQ ID NO 1117
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1117 tgcctcaac                                                                9

<210> SEQ ID NO 1118
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1118 ctcctcaac                                                                9

<210> SEQ ID NO 1119
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1119 ggtctcaac                                                                9

<210> SEQ ID NO 1120
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1120 cctctcaac                                                                9

<210> SEQ ID NO 1121
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1121
``` ccgttcaac                                                                9

<210> SEQ ID NO 1122
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1122 cgcttcaac                                                                9

<210> SEQ ID NO 1123
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1123 gccttcaac                                                                9

<210> SEQ ID NO 1124
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1124 gcggataac                                                                9

<210> SEQ ID NO 1125
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1125 ggcgataac                                                                9

<210> SEQ ID NO 1126
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1126 cggcataac                                                                9

<210> SEQ ID NO 1127
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1127 cggagtaac                                                                9

<210> SEQ ID NO 1128
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 1128 gcgagtaac                                                                         9

<210> SEQ ID NO 1129
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1129 ggcagtaac                                                                         9

<210> SEQ ID NO 1130
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1130 ggaggtaac                                                                         9

<210> SEQ ID NO 1131
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1131 ccaggtaac                                                                         9

<210> SEQ ID NO 1132
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1132 gacggtaac                                                                         9

<210> SEQ ID NO 1133
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1133 agcggtaac                                                                         9

<210> SEQ ID NO 1134
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1134 tccggtaac                                                                         9
```

<210> SEQ ID NO 1135
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1135 ctcggtaac                                                                 9

<210> SEQ ID NO 1136
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1136 cgtggtaac                                                                 9

<210> SEQ ID NO 1137
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1137 gctggtaac                                                                 9

<210> SEQ ID NO 1138
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1138 cgacgtaac                                                                 9

<210> SEQ ID NO 1139
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1139 gcacgtaac                                                                 9

<210> SEQ ID NO 1140
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1140 gagcgtaac                                                                 9

<210> SEQ ID NO 1141
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1141 aggcgtaac                                                                9

<210> SEQ ID NO 1142
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1142 tcgcgtaac                                                                9

<210> SEQ ID NO 1143
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1143 ctgcgtaac                                                                9

<210> SEQ ID NO 1144
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1144 caccgtaac                                                                9

<210> SEQ ID NO 1145
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1145 tgccgtaac                                                                9

<210> SEQ ID NO 1146
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1146 gtccgtaac                                                                9

<210> SEQ ID NO 1147
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1147 ggtcgtaac                                                                9

<210> SEQ ID NO 1148

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1148 cctcgtaac                                                                  9

<210> SEQ ID NO 1149
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1149 ccgtgtaac                                                                  9

<210> SEQ ID NO 1150
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1150 cgctgtaac                                                                  9

<210> SEQ ID NO 1151
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1151 gcctgtaac                                                                  9

<210> SEQ ID NO 1152
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1152 ccgactaac                                                                  9

<210> SEQ ID NO 1153
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1153 cgcactaac                                                                  9

<210> SEQ ID NO 1154
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1154
```

```
gccactaac                                                              9

<210> SEQ ID NO 1155
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1155 cgagctaac                                                              9

<210> SEQ ID NO 1156
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1156 gcagctaac                                                              9

<210> SEQ ID NO 1157
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1157 gaggctaac                                                              9

<210> SEQ ID NO 1158
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1158 acggctaac                                                              9

<210> SEQ ID NO 1159
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1159 ctggctaac                                                              9

<210> SEQ ID NO 1160
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1160 cacgctaac                                                              9

<210> SEQ ID NO 1161
<211> LENGTH: 9
<212> TYPE: DNA
```

```
<213> ORGANISM: Artificial Sequence
<220> FEATURE:
<223> OTHER INFORMATION: Barcoding Sequence

<400> SEQUENCE: 1161 tgcgctaac                                                                9

<210> SEQ ID NO 1162
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1162 gtcgctaac                                                                9

<210> SEQ ID NO 1163
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1163 ggtgctaac                                                                9

<210> SEQ ID NO 1164
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1164 cctgctaac                                                                9

<210> SEQ ID NO 1165
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1165 ggacctaac                                                                9

<210> SEQ ID NO 1166
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1166 ccacctaac                                                                9

<210> SEQ ID NO 1167
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1167 cagcctaac                                                                9
```

```
<210> SEQ ID NO 1168
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1168 tggcctaac                                                              9

<210> SEQ ID NO 1169
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1169 gtgcctaac                                                              9

<210> SEQ ID NO 1170
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1170 cgtcctaac                                                              9

<210> SEQ ID NO 1171
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1171 gctcctaac                                                              9

<210> SEQ ID NO 1172
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1172 cggtctaac                                                              9

<210> SEQ ID NO 1173
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1173 gcgtctaac                                                              9

<210> SEQ ID NO 1174
<211> LENGTH: 9
<212> TYPE: DNA
<213> ORGANISM: Artificial Sequence
<220> FEATURE:
```

```
<223> OTHER INFORMATION: Barcoding Sequence

<400> SEQUENCE: 1174 ggctctaac                                                                 9

<210> SEQ ID NO 1175
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1175 ccggttaac                                                                 9

<210> SEQ ID NO 1176
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1176 cgcgttaac                                                                 9

<210> SEQ ID NO 1177
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1177 gccgttaac                                                                 9

<210> SEQ ID NO 1178
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1178 gcgcttaac                                                                 9

<210> SEQ ID NO 1179
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1179 ggccttaac                                                                 9

<210> SEQ ID NO 1180
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1180 ggagaagac                                                                 9
```

```
<210> SEQ ID NO 1181
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1181 ccagaagac                                                                  9

<210> SEQ ID NO 1182
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1182 gaggaagac                                                                  9

<210> SEQ ID NO 1183
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1183 acggaagac                                                                  9

<210> SEQ ID NO 1184
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1184 ctggaagac                                                                  9

<210> SEQ ID NO 1185
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1185 cacgaagac                                                                  9

<210> SEQ ID NO 1186
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1186 agcgaagac                                                                  9

<210> SEQ ID NO 1187
<211> LENGTH: 9
<212> TYPE: DNA
<213> ORGANISM: Artificial Sequence
<220> FEATURE:
<223> OTHER INFORMATION: Barcoding Sequence
```

<400> SEQUENCE: 1187 tccgaagac                                                                       9

<210> SEQ ID NO 1188
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1188 gtcgaagac                                                                       9

<210> SEQ ID NO 1189
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1189 cgtgaagac                                                                       9

<210> SEQ ID NO 1190
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1190 gctgaagac                                                                       9

<210> SEQ ID NO 1191
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1191 cgacaagac                                                                       9

<210> SEQ ID NO 1192
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1192 gcacaagac                                                                       9

<210> SEQ ID NO 1193
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1193 cagcaagac                                                                       9

<210> SEQ ID NO 1194
<211> LENGTH: 9

```
<212> TYPE: DNA
<213> ORGANISM: Artificial Sequence
<220> FEATURE:
<223> OTHER INFORMATION: Barcoding Sequence

<400> SEQUENCE: 1194 aggcaagac                                                                 9

<210> SEQ ID NO 1195
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1195 tcgcaagac                                                                 9

<210> SEQ ID NO 1196
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1196 gtgcaagac                                                                 9

<210> SEQ ID NO 1197
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1197 gaccaagac                                                                 9

<210> SEQ ID NO 1198
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1198 tgccaagac                                                                 9

<210> SEQ ID NO 1199
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1199 ctccaagac                                                                 9

<210> SEQ ID NO 1200
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1200
``` ggtcaagac 9

<210> SEQ ID NO 1201
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1201 cctcaagac 9

<210> SEQ ID NO 1202
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1202 cggtaagac 9

<210> SEQ ID NO 1203
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1203 gcgtaagac 9

<210> SEQ ID NO 1204
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1204 ggctaagac 9

<210> SEQ ID NO 1205
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1205 ggaagagac 9

<210> SEQ ID NO 1206
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1206 ccaagagac 9

<210> SEQ ID NO 1207
<211> LENGTH: 9
<212> TYPE: DNA
<213> ORGANISM: Artificial Sequence

```
<220> FEATURE:
<223> OTHER INFORMATION: Barcoding Sequence

<400> SEQUENCE: 1207 gagagagac                                                                9

<210> SEQ ID NO 1208
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1208 aggagagac                                                                9

<210> SEQ ID NO 1209
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1209 tcgagagac                                                                9

<210> SEQ ID NO 1210
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1210 ctgagagac                                                                9

<210> SEQ ID NO 1211
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1211 cacagagac                                                                9

<210> SEQ ID NO 1212
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1212 tgcagagac                                                                9

<210> SEQ ID NO 1213
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1213 accagagac                                                                9
```

<210> SEQ ID NO 1214
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1214 gtcagagac                                                                  9

<210> SEQ ID NO 1215
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1215 cgtagagac                                                                  9

<210> SEQ ID NO 1216
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1216 gctagagac                                                                  9

<210> SEQ ID NO 1217
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1217 gaaggagac                                                                  9

<210> SEQ ID NO 1218
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1218 agaggagac                                                                  9

<210> SEQ ID NO 1219
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1219 tcaggagac                                                                  9

<210> SEQ ID NO 1220
<211> LENGTH: 9
<212> TYPE: DNA
<213> ORGANISM: Artificial Sequence
<220> FEATURE:
<223> OTHER INFORMATION: Barcoding Sequence

```
<400> SEQUENCE: 1220 ctaggagac                                                                9

<210> SEQ ID NO 1221
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1221 aacggagac                                                                9

<210> SEQ ID NO 1222
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1222 ttcggagac                                                                9

<210> SEQ ID NO 1223
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1223 catggagac                                                                9

<210> SEQ ID NO 1224
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1224 tgtggagac                                                                9

<210> SEQ ID NO 1225
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1225 actggagac                                                                9

<210> SEQ ID NO 1226
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1226 gttggagac                                                                9

<210> SEQ ID NO 1227
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1227 caacgagac                                                                9

<210> SEQ ID NO 1228
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1228 tgacgagac                                                                9

<210> SEQ ID NO 1229
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1229 acacgagac                                                                9

<210> SEQ ID NO 1230
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1230 gtacgagac                                                                9

<210> SEQ ID NO 1231
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1231 aagcgagac                                                                9

<210> SEQ ID NO 1232
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1232 ttgcgagac                                                                9

<210> SEQ ID NO 1233
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1233
``` taccgagac 9

<210> SEQ ID NO 1234
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1234 atccgagac 9

<210> SEQ ID NO 1235
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1235 gatcgagac 9

<210> SEQ ID NO 1236
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1236 agtcgagac 9

<210> SEQ ID NO 1237
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1237 cttcgagac 9

<210> SEQ ID NO 1238
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1238 cgatgagac 9

<210> SEQ ID NO 1239
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1239 gcatgagac 9

<210> SEQ ID NO 1240
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 1240 cagtgagac                                                                9

<210> SEQ ID NO 1241
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1241 tggtgagac                                                                9

<210> SEQ ID NO 1242
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1242 acgtgagac                                                                9

<210> SEQ ID NO 1243
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1243 gtgtgagac                                                                9

<210> SEQ ID NO 1244
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1244 gactgagac                                                                9

<210> SEQ ID NO 1245
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1245 agctgagac                                                                9

<210> SEQ ID NO 1246
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1246 tcctgagac                                                                9
```

<210> SEQ ID NO 1247
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1247 ctctgagac                                                                 9

<210> SEQ ID NO 1248
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1248 ggttgagac                                                                 9

<210> SEQ ID NO 1249
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1249 ccttgagac                                                                 9

<210> SEQ ID NO 1250
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1250 cgaacagac                                                                 9

<210> SEQ ID NO 1251
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1251 gcaacagac                                                                 9

<210> SEQ ID NO 1252
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1252 cagacagac                                                                 9

<210> SEQ ID NO 1253
<211> LENGTH: 9
<212> TYPE: DNA
<213> ORGANISM: Artificial Sequence
<220> FEATURE:

-continued

<223> OTHER INFORMATION: Barcoding Sequence

<400> SEQUENCE: 1253 tggacagac                                                                9

<210> SEQ ID NO 1254
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1254 acgacagac                                                                9

<210> SEQ ID NO 1255
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1255 gtgacagac                                                                9

<210> SEQ ID NO 1256
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1256 gacacagac                                                                9

<210> SEQ ID NO 1257
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1257 agcacagac                                                                9

<210> SEQ ID NO 1258
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1258 tccacagac                                                                9

<210> SEQ ID NO 1259
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1259 ctcacagac                                                                9

```
<210> SEQ ID NO 1260
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1260 ggtacagac                                                                 9

<210> SEQ ID NO 1261
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1261 cctacagac                                                                 9

<210> SEQ ID NO 1262
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1262 cacgaa                                                                    6

<210> SEQ ID NO 1263
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1263 taaggc                                                                    6

<210> SEQ ID NO 1264
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1264 tgatgg                                                                    6

<210> SEQ ID NO 1265
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1265 tggcat                                                                    6

<210> SEQ ID NO 1266
<211> LENGTH: 6
<212> TYPE: DNA
<213> ORGANISM: Artificial Sequence
<220> FEATURE:
<223> OTHER INFORMATION: Barcoding Sequence
```

```
<400> SEQUENCE: 1266 ccagaa                                                                      6

<210> SEQ ID NO 1267
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1267 atccga                                                                      6

<210> SEQ ID NO 1268
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1268 cgaaca                                                                      6

<210> SEQ ID NO 1269
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1269 catgag                                                                      6

<210> SEQ ID NO 1270
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1270 taggtg                                                                      6

<210> SEQ ID NO 1271
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1271 catagc                                                                      6

<210> SEQ ID NO 1272
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1272 ccacat                                                                      6

<210> SEQ ID NO 1273
<211> LENGTH: 6
```

```
<212> TYPE: DNA
<213> ORGANISM: Artificial Sequence
<220> FEATURE:
<223> OTHER INFORMATION: Barcoding Sequence

<400> SEQUENCE: 1273 accaca                                                                  6

<210> SEQ ID NO 1274
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1274 gatacc                                                                  6

<210> SEQ ID NO 1275
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1275 cagaac                                                                  6

<210> SEQ ID NO 1276
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1276 ccacta                                                                  6

<210> SEQ ID NO 1277
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1277 cagtag                                                                  6

<210> SEQ ID NO 1278
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1278 acaagc                                                                  6

<210> SEQ ID NO 1279
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1279
```

```
tcatgc                                                        6

<210> SEQ ID NO 1280
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1280 atcacc                                                        6

<210> SEQ ID NO 1281
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1281 gactag                                                        6

<210> SEQ ID NO 1282
<211> LENGTH: 6
<212> TYPE: DNA
<213> ORGANISM: Artificial Sequence
<220> FEATURE:
<223> OTHER INFORMATION: Barcoding Sequence

<400> SEQUENCE: 1282 cttcga                                                        6

<210> SEQ ID NO 1283
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1283 cggaagaat                                                     9

<210> SEQ ID NO 1284
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1284 gcgaagaat                                                     9

<210> SEQ ID NO 1285
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1285 ggcaagaat                                                     9

<210> SEQ ID NO 1286
<211> LENGTH: 9
<212> TYPE: DNA
<213> ORGANISM: Artificial Sequence
```

<220> FEATURE:
<223> OTHER INFORMATION: Barcoding Sequence

<400> SEQUENCE: 1286 ggagagaat                                                                      9

<210> SEQ ID NO 1287
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1287 ccagagaat                                                                      9

<210> SEQ ID NO 1288
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1288 gaggagaat                                                                      9

<210> SEQ ID NO 1289
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1289 acggagaat                                                                      9

<210> SEQ ID NO 1290
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1290 ctggagaat                                                                      9

<210> SEQ ID NO 1291
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1291 cacgagaat                                                                      9

<210> SEQ ID NO 1292
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1292 agcgagaat                                                                      9

```
<210> SEQ ID NO 1293
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1293 tccgagaat                                                                 9

<210> SEQ ID NO 1294
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1294 gtcgagaat                                                                 9

<210> SEQ ID NO 1295
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1295 cgtgagaat                                                                 9

<210> SEQ ID NO 1296
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1296 gctgagaat                                                                 9

<210> SEQ ID NO 1297
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1297 cgacagaat                                                                 9

<210> SEQ ID NO 1298
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1298 gcacagaat                                                                 9

<210> SEQ ID NO 1299
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 1299 cagcagaat                                                                9

<210> SEQ ID NO 1300
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1300 aggcagaat                                                                9

<210> SEQ ID NO 1301
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1301 tcgcagaat                                                                9

<210> SEQ ID NO 1302
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1302 gtgcagaat                                                                9

<210> SEQ ID NO 1303
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1303 gaccagaat                                                                9

<210> SEQ ID NO 1304
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1304 tgccagaat                                                                9

<210> SEQ ID NO 1305
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1305 ctccagaat                                                                9

<210> SEQ ID NO 1306
```

```
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1306 ggtcagaat                                                                 9

<210> SEQ ID NO 1307
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1307 cctcagaat                                                                 9

<210> SEQ ID NO 1308
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1308 ccgtagaat                                                                 9

<210> SEQ ID NO 1309
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1309 cgctagaat                                                                 9

<210> SEQ ID NO 1310
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1310 gcctagaat                                                                 9

<210> SEQ ID NO 1311
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1311 ggaaggaat                                                                 9

<210> SEQ ID NO 1312
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1312
``` ccaaggaat                                                              9

<210> SEQ ID NO 1313
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1313 gagaggaat                                                              9

<210> SEQ ID NO 1314
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1314 aggaggaat                                                              9

<210> SEQ ID NO 1315
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1315 tcgaggaat                                                              9

<210> SEQ ID NO 1316
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1316 ctgaggaat                                                              9

<210> SEQ ID NO 1317
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1317 cacaggaat                                                              9

<210> SEQ ID NO 1318
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1318 tgcaggaat                                                              9

<210> SEQ ID NO 1319
<211> LENGTH: 9
<212> TYPE: DNA

```
<213> ORGANISM: Artificial Sequence
<220> FEATURE:
<223> OTHER INFORMATION: Barcoding Sequence

<400> SEQUENCE: 1319 accaggaat                                                            9

<210> SEQ ID NO 1320
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1320 gtcaggaat                                                            9

<210> SEQ ID NO 1321
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1321 cgtaggaat                                                            9

<210> SEQ ID NO 1322
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1322 gctaggaat                                                            9

<210> SEQ ID NO 1323
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1323 gaacggaat                                                            9

<210> SEQ ID NO 1324
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1324 agacggaat                                                            9

<210> SEQ ID NO 1325
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1325 tcacggaat                                                            9
```

```
<210> SEQ ID NO 1326
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1326 ctacggaat                                                                  9

<210> SEQ ID NO 1327
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1327 aagcggaat                                                                  9

<210> SEQ ID NO 1328
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1328 ttgcggaat                                                                  9

<210> SEQ ID NO 1329
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1329 taccggaat                                                                  9

<210> SEQ ID NO 1330
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1330 atccggaat                                                                  9

<210> SEQ ID NO 1331
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1331 catcggaat                                                                  9

<210> SEQ ID NO 1332
<211> LENGTH: 9
<212> TYPE: DNA
<213> ORGANISM: Artificial Sequence
<220> FEATURE:
```

-continued

<223> OTHER INFORMATION: Barcoding Sequence

<400> SEQUENCE: 1332 tgtcggaat                                                                 9

<210> SEQ ID NO 1333
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1333 actcggaat                                                                 9

<210> SEQ ID NO 1334
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1334 gttcggaat                                                                 9

<210> SEQ ID NO 1335
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1335 cgatggaat                                                                 9

<210> SEQ ID NO 1336
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1336 gcatggaat                                                                 9

<210> SEQ ID NO 1337
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1337 cagtggaat                                                                 9

<210> SEQ ID NO 1338
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1338 tggtggaat                                                                 9

```
<210> SEQ ID NO 1339
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1339 acgtggaat                                                                  9

<210> SEQ ID NO 1340
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1340 gtgtggaat                                                                  9

<210> SEQ ID NO 1341
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1341 gactggaat                                                                  9

<210> SEQ ID NO 1342
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1342 agctggaat                                                                  9

<210> SEQ ID NO 1343
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1343 tcctggaat                                                                  9

<210> SEQ ID NO 1344
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1344 ctctggaat                                                                  9

<210> SEQ ID NO 1345
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 1345 ggttggaat                                                              9

<210> SEQ ID NO 1346
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1346 ccttggaat                                                              9

<210> SEQ ID NO 1347
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1347 cgaacgaat                                                              9

<210> SEQ ID NO 1348
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1348 gcaacgaat                                                              9

<210> SEQ ID NO 1349
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1349 cagacgaat                                                              9

<210> SEQ ID NO 1350
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1350 tggacgaat                                                              9

<210> SEQ ID NO 1351
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1351 acgacgaat                                                              9

<210> SEQ ID NO 1352
<211> LENGTH: 9
```

```
-continued

<212> TYPE: DNA
<213> ORGANISM: Artificial Sequence
<220> FEATURE:
<223> OTHER INFORMATION: Barcoding Sequence

<400> SEQUENCE: 1352 gtgacgaat                                                             9

<210> SEQ ID NO 1353
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1353 gacacgaat                                                             9

<210> SEQ ID NO 1354
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1354 agcacgaat                                                             9

<210> SEQ ID NO 1355
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1355 tccacgaat                                                             9

<210> SEQ ID NO 1356
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1356 ctcacgaat                                                             9

<210> SEQ ID NO 1357
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1357 tagctcgaa                                                             9

<210> SEQ ID NO 1358
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1358
```

```
atgctcgaa                                                        9

<210> SEQ ID NO 1359
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1359 aacctcgaa                                                        9

<210> SEQ ID NO 1360
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1360 ttcctcgaa                                                        9

<210> SEQ ID NO 1361
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1361 gatctcgaa                                                        9

<210> SEQ ID NO 1362
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1362 agtctcgaa                                                        9

<210> SEQ ID NO 1363
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1363 tctctcgaa                                                        9

<210> SEQ ID NO 1364
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1364 cttctcgaa                                                        9

<210> SEQ ID NO 1365
<211> LENGTH: 9
<212> TYPE: DNA
<213> ORGANISM: Artificial Sequence
```

```
<220> FEATURE:
<223> OTHER INFORMATION: Barcoding Sequence

<400> SEQUENCE: 1365 ggattcgaa                                                                9

<210> SEQ ID NO 1366
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1366 ccattcgaa                                                                9

<210> SEQ ID NO 1367
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1367 cagttcgaa                                                                9

<210> SEQ ID NO 1368
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1368 tggttcgaa                                                                9

<210> SEQ ID NO 1369
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1369 acgttcgaa                                                                9

<210> SEQ ID NO 1370
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1370 gtgttcgaa                                                                9

<210> SEQ ID NO 1371
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1371 gacttcgaa                                                                9
```

```
<210> SEQ ID NO 1372
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1372 agcttcgaa                                                                 9

<210> SEQ ID NO 1373
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1373 caagcagac                                                                 9

<210> SEQ ID NO 1374
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1374 tgagcagac                                                                 9

<210> SEQ ID NO 1375
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1375 acagcagac                                                                 9

<210> SEQ ID NO 1376
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1376 gtagcagac                                                                 9

<210> SEQ ID NO 1377
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1377 aaggcagac                                                                 9

<210> SEQ ID NO 1378
<211> LENGTH: 9
<212> TYPE: DNA
<213> ORGANISM: Artificial Sequence
<220> FEATURE:
<223> OTHER INFORMATION: Barcoding Sequence
```

```
<400> SEQUENCE: 1378 ttggcagac                                                                    9

<210> SEQ ID NO 1379
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1379 tacgcagac                                                                    9

<210> SEQ ID NO 1380
<211> LENGTH: 9
<212> TYPE: DNA
<213> ORGANISM: Artificial Sequence
<220> FEATURE:
<223> OTHER INFORMATION: Barcoding Sequence

<400> SEQUENCE: 1380 atcgcagac                                                                    9

<210> SEQ ID NO 1381
<211> LENGTH: 22
<212> TYPE: DNA
<213> ORGANISM: Artificial Sequence
<220> FEATURE:
<223> OTHER INFORMATION: Profiling Sequence 1

<400> SEQUENCE: 1381
ttctagagcg gccgcttcga gc                                                    22

<210> SEQ ID NO 1382
<211> LENGTH: 22
<212> TYPE: DNA
<213> ORGANISM: Artificial Sequence
<220> FEATURE:
<223> OTHER INFORMATION: Profiling Sequence 2

<400> SEQUENCE: 1382
cgctgatctc acgccgtggt ga                                                    22

<210> SEQ ID NO 1383
<211> LENGTH: 22
<212> TYPE: DNA
<213> ORGANISM: Artificial Sequence
<220> FEATURE:
<223> OTHER INFORMATION: Poly A Tailing Sequence

<400> SEQUENCE: 1383
agttccgcgt acgtacggcg tc                                                    22

<210> SEQ ID NO 1384
<211> LENGTH: 63
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (30)..(41)
<223> OTHER INFORMATION: n is a, c, g, or t

<400> SEQUENCE: 1384
```

```
tctttcccta cacgacgctc ttccgatctn nnnnnnnnnn ntcaccacgg cgtgagatca    60
gcg                                                                  63
```

<210> SEQ ID NO 1385
<211> LENGTH: 22
<212> TYPE: DNA
<213> ORGANISM: Artificial Sequence
<220> FEATURE:
<223> OTHER INFORMATION: PCR Primer

<400> SEQUENCE: 1385

```
gacgccgtac gtacgcggaa ct                                             22
```

<210> SEQ ID NO 1386
<211> LENGTH: 29
<212> TYPE: DNA
<213> ORGANISM: Artificial Sequence
<220> FEATURE:
<223> OTHER INFORMATION: PCR Primer

<400> SEQUENCE: 1386

```
acatttgctt ctgacacaac tgtgttcac                                      29
```

<210> SEQ ID NO 1387
<211> LENGTH: 30
<212> TYPE: DNA
<213> ORGANISM: Artificial Sequence
<220> FEATURE:
<223> OTHER INFORMATION: PCR Primer

<400> SEQUENCE: 1387

```
atggccgttt acccatacga tgttcctgac                                     30
```

<210> SEQ ID NO 1388
<211> LENGTH: 29
<212> TYPE: DNA
<213> ORGANISM: Artificial Sequence
<220> FEATURE:
<223> OTHER INFORMATION: PCR Primer

<400> SEQUENCE: 1388

```
tctttcccta cacgacgctc ttccgatct                                      29
```

<210> SEQ ID NO 1389
<211> LENGTH: 50
<212> TYPE: DNA
<213> ORGANISM: Artificial Sequence
<220> FEATURE:
<223> OTHER INFORMATION: PCR Primer

<400> SEQUENCE: 1389

```
ggagttcaga cgtgtgctct tccgatcttt ctagagcggc cgcttcgagc               50
```

<210> SEQ ID NO 1390
<211> LENGTH: 28
<212> TYPE: DNA
<213> ORGANISM: Artificial Sequence
<220> FEATURE:
<223> OTHER INFORMATION: PCR Primer

<400> SEQUENCE: 1390

```
gggcaaccta atacgactca ctataggg                                       28
```